(12) United States Patent
O'Neil et al.

(10) Patent No.: US 7,138,395 B2
(45) Date of Patent: Nov. 21, 2006

(54) INTERLEUKIN-1β CONVERTING ENZYME INHIBITORS

(75) Inventors: Steven Victor O'Neil, Morrow, OH (US); Michael Christopher Laufersweiler, Maineville, OH (US); Yili Wang, Mason, OH (US); Kofi Abeka Oppong, Fairfield, OH (US); David Lindsey Soper, Mason, OH (US); John August Wos, Maineville, OH (US); Biswanath De, Cincinnati, OH (US); Thomas Prosser Demuth, Jr., Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 165 days.

(21) Appl. No.: 10/457,188

(22) Filed: Jun. 9, 2003

(65) Prior Publication Data
US 2004/0014753 A1 Jan. 22, 2004

Related U.S. Application Data

(60) Provisional application No. 60/389,335, filed on Jun. 17, 2002, provisional application No. 60/387,500, filed on Jun. 10, 2002.

(51) Int. Cl.
| | |
|---|---|
| *C07D 471/04* | (2006.01) |
| *C07D 498/04* | (2006.01) |
| *A61K 31/4995* | (2006.01) |
| *A61K 31/537* | (2006.01) |
| *A61P 29/00* | (2006.01) |

(52) U.S. Cl. .................. 514/230.5; 514/249; 514/299; 540/461

(58) Field of Classification Search ............... 540/461; 514/230.5, 249, 299
See application file for complete search history.

(56) References Cited

U.S. PATENT DOCUMENTS

| 5,716,929 A | 2/1998 | Bemis et al. |
| 5,973,111 A | 10/1999 | Bemis et al. |
| 6,025,147 A | 2/2000 | Bemis et al. |
| 6,103,711 A | 8/2000 | Bemis et al. |

FOREIGN PATENT DOCUMENTS

| WO | WO 98/32766 A1 | 7/1998 |
| WO | WO 98/50032 A1 | 11/1998 |
| WO | WO 02/081420 A1 | 10/2002 |

*Primary Examiner*—Bruck Kifle
(74) *Attorney, Agent, or Firm*—Richard S. Echler, Sr.

(57) ABSTRACT

The present invention relates to novel compounds, compositions comprising said compounds, and uses thereof, said compounds having the formula:

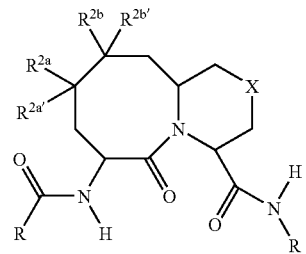

X is —$CH_2$—, —O— or —$NR^9$—;
R is a carbocyclic or heterocyclic ring;
$R^1$ is a cysteine trap;
$R^{2a}$, $R^{2a'}$, $R^{2b}$, and $R^{2b'}$ are each independently hydrogen, $C_1$–$C_4$ alkyl, $C_1$–$C_4$ alkoxy, and mixtures thereof; or $R^{2a'}$ and $R^{2b'}$ can taken together to form a double bond; $R^9$ is hydrogen or a unit having the formula -$L^2$-$R^{10}$; L is the same as defined herein above; $R^{10}$ is hydrogen; substituted or unsubstituted $C_1$–$C_6$ linear; branched, or cyclic hydrocarbyl; substituted or unsubstituted aryl; substituted or unsubstituted $C_1$–$C_9$ heterocyclic; and substituted or unsubstituted heteroaryl.

69 Claims, No Drawings

INTERLEUKIN-1β CONVERTING ENZYME INHIBITORS

CROSS REFERENCE TO RELATED APPLICATIONS

This application claims priority under Title 35, United States Code 119(e) from Provisional Application Ser. No. 60/387,500, filed Jun. 10, 2002 and Provisional Application Ser. No. 60/389,335, filed Jun. 17, 2002.

FIELD OF THE INVENTION

The present invention relates to novel 8,6-fused ring heterocycles that are Interleukin-β converting enzyme (ICE) inhibitors. The present invention also relates to pharmaceutical compositions comprising said inhibitors. The present invention further relates to methods for controlling one or more disease processes related to Interleukin-β activity.

BACKGROUND OF THE INVENTION

Cytokines, in general, are important signaling molecules that are essential to immune and inflammatory responses in mammals. Interleukin-1β and IL-18 are key components of the cytokine network. IL-1β stimulates the production of Tumor Necrosis Factor-α (TNF-α), and the combined action of IL-1β, IL-18 and TNF-α induces further cytokine production, chemokine production, expression of cellular adhesion molecules, and increased vascular permeability. In addition, IL-1β stimulates fibroblast differentiation and proliferation, the production of prostaglandins, collagenase and phospholipase by synovial cell and chondrocytes, basophil and eosinophil degranulation, and neutrophil activation. These mediators contribute to autoimmune and inflammatory disorders in many organ systems.

IL-1β possesses diverse biological effects contributing to the pathogenesis of acute and chronic inflammatory and autoimmune diseases (C A Dinarello, *Blood*, (1996) 87, 2095). For example, Il-1β contributes to disease progression in rheumatoid arthritis and osteoarthritis, where it mediates inflammatory symptoms, contributes to the destruction of cartilage proteoglycan, and also contributes to bone loss in afflicted joints. IL-1β overexpression also contributes to disease progression in atherosclerosis by regulating the expression and activation of matrix metalloproteases. Other conditions where IL-1β plays a major role in pathogenesis include sepsis syndrome, inflammatory bowel syndrome, acute and chronic myelogenous leukemia, insulin-dependent diabetes mellitus, osteoporosis, and periodontal disease.

The caspases are a family of structurally similar, intracellular cysteine proteases that play an important role in cytokine maturation and apoptosis. Caspase-1 (interleukin-1β converting enzyme, ICE) is primarily responsible for key steps in immunity and the inflammatory response since it catalyzes the proteolytic cleavage of the pro-inflammatory cytokines pro-IL-1β and pro-IL-18 to the bioactive forms IL-1β and IL-18. Since IL-1β triggers a multitude of biological responses and is implicated in the pathogenesis of many inflammatory diseases, as outlined above, the inhibition of ICE is a recognized target for therapeutic intervention. Therefore, ICE inhibitors have utility for the treatment of inflammatory diseases and autoimmune diseases, such as RA and OA. In addition, other caspases and related homologs of ICE appear to be involved regulating biological processes such as apoptosis. Therefore, inhibition of caspases also provides a recognized therapeutic approach for treating additional pathological conditions. Diseases where caspase inhibitors can provide theraputic utility include neurodegenerative diseases (such as Alzheimer's, Huntington's, and Parkinson's diseases), ischemia, stroke, and trauma.

There is therefore a long felt need in the art for pharmaceutical compositions which comprise novel active ingredients for reversibly or irreversibly inhibiting Caspase enzymes resulting in the treatment of pathological conditions and diseases described further herein, inter alia, inflammation of joints and other forms of synovial tissue associated with osteoarthritis and rheumatoid arthritis, Huntington's Disease, Alzheimer's disease, neuronal death, brain, intestinal or mycardial ischemia, repurfusion injury, endotoxic shock, amyotrophic lateral sclerosis, multiple sclerosis, atherosclerosis, hepatitis, inflammatory bowel syndrome, shigellosis, meningitis, sepsis, acute and chronic myelogenous leukemia, insulin-dependent diabetes mellitus, osteoporosis, and periodontal disease. Each of these disease states involves cytokine activity, which can be abated, controlled or otherwise mediated by the limiting or stopping the activity of one or more Caspase enzymes.

SUMMARY OF THE INVENTION

The present invention meets the aforementioned needs in that it has been surprisingly found that certain 8,6-fused ring heterocycles are effective for inhibiting Interleukin-1β Converting Enzyme and thereby preventing, abating, or otherwise controlling the extracellular release of the 17 kD IL-1β enzyme which is proposed to be the active component responsible for the herein described disease states.

The first aspect of the present invention relates to novel compounds that inhibit Caspase enzymes, inter alia, Interleukin-1β (IL-1β) Converting Enzyme (ICE, Caspase-1), said compounds having the formula:

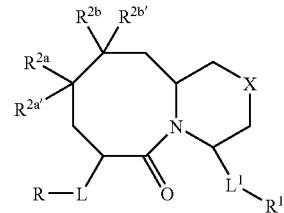

wherein R is a carbocyclic or heterocyclic ring;

$R^1$ is a cysteine trap;

$R^{2a}$, $R^{2a'}$, $R^{2b}$, and $R^{2b'}$ are each independently hydrogen, hydroxyl, —N$(R^6)_2$, halogen, $C_1$–$C_4$ alkyl, $C_1$–$C_4$ alkoxy, and mixtures thereof; or $R^{2a'}$ and $R^{2b'}$ can be taken together to form a double bond;

X is —CH$_2$—, —O— or —NR$^9$—;

$R^9$ is hydrogen or a unit having the formula -L$^2$-R$^{10}$; R$^{10}$ is hydrogen; substituted or unsubstituted $C_1$–$C_6$ linear; branched, or cyclic hydrocarbyl; substituted or unsubstituted aryl; substituted or unsubstituted $C_1$–$C_9$ heterocyclic; and substituted or unsubstituted heteroaryl;

L, L¹, and L² are linking units each independently having the formula:

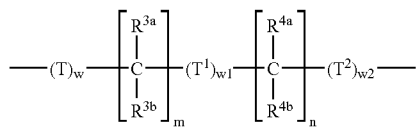

T, T¹, and T² are each independently selected from the group consisting of:
   i) —NR⁶—;
   ii) —O—;
   iii) —S(O)₂—;
   iv) —NR⁶S(O)₂—;
   v) —S(O)₂NR⁶—; and
   vi) mixtures thereof;

R⁶ is hydrogen, substituted or unsubstituted $C_1$–$C_{10}$ linear, branched, or cyclic alkyl, $C_6$–$C_{10}$ aryl, $C_7$–$C_{12}$ alkylenearyl, and mixtures thereof; the indices w, w¹, and W² are each independently 0 or 1;

$R^{3a}$, $R^{3b}$, $R^{4a}$, and $R^{4b}$ are each independently:
   i) hydrogen;
   ii) $C_1$–$C_4$ linear, branched, and cyclic alkyl;
   iii) $R^{3a}$ and $R^{3b}$ or $R^{4a}$, and $R^{4b}$ can be taken together to form a carbonyl unit;
   iv) two $R^{3a}$ or two $R^{3b}$ units from adjacent carbon atoms or two $R^{4a}$ or two $R^{4b}$ units from adjacent carbon atoms can be taken together to form a double bond; and
   v) mixtures thereof;

the index m is from 0 to 5; the index n is from 0 to 5.

Another aspect of the present invention relates to pharmaceutical compositions. The compounds of the present invention have improved oral bioavailability and this advantage is made use of by the second aspect of the present invention wherein the formulator can deliver the compounds of the present invention to a human or higher mammal by administering a composition comprising:

a) an effective amount of one or more interleukin-1β converting enzyme inhibitors according to the present invention; and
b) one or more pharmaceutically acceptable excipients.

As described herein below, the compositions of the present invention are effective in controlling one or more interleukin-1β converting enzyme inhibitor mediated or interleukin-1β converting enzyme inhibitor modulated mammalian diseases or conditions.

A further aspect of the present invention relates to methods for controlling diseases or disease states which are related to or caused by the increased activity of one or more Caspase enzymes, inter alia, Interleukin-1β Converting Enzyme (Caspase-1). The unmediated or uncontrolled activity of said enzymes can cause the release of higher levels of cytokines which exacerbate the disease state. The methods of the present invention control the amplification of IL-1β and other cytokines which are capable of being released by controlling the initial release of IL-1β.

Further, this invention relates to methods for treating diseases mediated by Caspase enzymes, including for example, acute and chronic inflammatory-mediated diseases, autoimmune diseases, destructive bone diseases, proliferative disorders, infectious diseases, and degenerative diseases.

In addition, this invention also relates to methods of treating diseases mediated by IL-1β. Specifically, the subject invention relates to methods for treating pathological conditions and diseases, such as neuronal death, brain, intestinal or mycardial ischemia, repurfusion injury, endotoxic shock, amyotrophic lateral sclerosis, multiple sclerosis, Parkinson's disease, Huntington's disease, Alzheimer's disease, atherosclerosis, hepatitis, inflammatory bowel syndrome, shigellosis, meningitis, sepsis, acute and chronic myelogenous leukemia, insulin-dependent diabetes mellitus, osteoporosis, periodontal disease, rheumatoid arthritis (RA) and osteoarthritis (OA).

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention relates to compounds which are interleukin-1β converting enzyme inhibitors, said compounds comprising an 8,6-fused ring system. Interleukin-1β is a cyctokine released by a chemical reaction catalyzed by the enzyme Caspase-1 (ICE) and the present invention specifically targets the inhibition of Caspase-1. The compounds of the present invention are surprisingly specific for inhibiting Caspase-1 enzyme, as well as being modifiable for to have enhanced specificity for other Caspase enzymes.

The compounds of the present invention comprise three elements:
   i) novel 8,6-fused ring scaffolds;
   ii) R units which are carbocyclic or heterocyclic rings attached by way of a linking unit to said scaffolds; and
   iii) R¹ units which are cysteine traps attached by way of a linking unit to said scaffolds.

The novel ICE inhibitors of the present invention have been surprisingly found to satisfy the specific size, shape, and binding requirement of the Caspase-1 active site and therefore are capable of reversibly or irreversibly inactivating the enzyme Caspase-1. However, the compounds of the present invention can also be modified within the metes and bounds of the present invention to provide activity against other cysteine and serine protease enzymes as well.

The novel scaffolds of the present invention surprisingly position the selected R unit, encompassed within the description herein below, in a manner allowing for a propitious interaction between the novel compounds of the present invention and Caspase I.

The cysteine traps of the present invention can be chosen by the formulator to interact reversibly or irreversibly with the target Caspase enzyme. In general, these traps comprise a first reactive moiety and a second reactive moiety. The first reactive moiety is a carboxyl unit (or carboxyl unit precursor) which is believed to fit into a specific carboxylate docking site along the enzyme active site and in doing so bring the second reactive moiety into proximity with a cysteine amino acid residue which reacts reversibly or irreversibly with the second reactive moiety rendering the enzyme inactive. The formulator, as described herein below, may select to reversibly or irreversibly (suicide inhibitor)

inhibit the activity of the Caspase enzyme depending upon the type of cytokine related disease, treatment type, or regiment of therapy.

In addition, the formulator may use either the "bio-active" or "bio-equivalent" form of a cysteine trap depending upon the pharmaceutical composition, mode of delivery, and the like. For the purposes of the present invention, the term "bio-active" is defined herein as "the chemical form of a group, unit or moiety which interacts with the target enzyme." For the purposes of the present invention, the term "bio-equivalent" is defined herein as "a precursor form of the bio-active form of a group, unit or moiety which is readily converted to the bio-active form upon delivery into the host species being treated. The bio-equivalent form is also converted to the bio-active form prior to interaction with the targeted enzymes during in vitro testing."

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include methyl, ethyl, propyl, pentyl, 1-butenyl, 2,2-dimethypentyl, 3-ethyl-3-methylpent-1-ynyl, 8,8-dimethylnon-3-enyl, and the like.

Included within the definition of "hydrocarbyl" are the aromatic (aryl) and non-aromatic carbocyclic rings. Non-limiting examples of substituted or unsubstituted aromatic and non-aromatic carbocyclic rings include cyclopentyl, cyclohexyl, 1-ethyl-2-methylcyclohexyl, cyclohexenyl, cycloheptanyl, cyclooctyl, octahydro-indenyl, 3,5-dimethyl-2,3,3a,4,5,6,9,9a-octahydro-1H-cyclopentacyclooctenyl, 4,6-dimethyl-1,2,3,4,4a,5,6,7,10,10a-decahydro-benzocyclooctenyl, phenyl, benzyl, 1-ethyl-2-methyl-benzyl, naphthyl, 3-methyl-1-propyl-naphthyl, indanyl, phenanthryl, 1,2,3,4-tetrahydronaphthalenyl, and the like.

The term "heterocycle" is included within the term hydrocarbyl and is described herein as a hydrocarbyl that contains one or more heteroatoms in the ring system. Heterocycle includes both aromatic (heteroaryl) and non-aromatic heterocyclic rings. Non-limiting substituted or unsubstituted examples include: pyrrolyl, 2H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, 2H-1,3-oxazinyl, 1,4-oxazinyl, morpholinyl, azepinyl, oxepinyl, 4H-1,2-diazepinyl, benzofuranyl, indolyl, 1H-indolyl, benzoxazolyl, quinolinyl, isoquinolinyl, 2H-1,4-benzoxazinyl, pyrrolidinyl, pyrrolinyl, furanyl, thiophenyl, benzimidazolyl, 6-amino-5-oxo-3,4,4a,5,6,7,10,10a-octahydro-1H-cycloocta[c]pyran-4-carboxylic acid, 6-amino-5-oxo-1,2,3,4,4a,5,6,7,10,10a-decahydro-cycloocta[c]pyridine-4-carboxylic acid, (2-Ethoxy-5-oxo-tetrahydro-furan-3-yl)-carbamic acid allyl ester and the like.

The terms "arylene" and "heteroarylene" relate to aryl and heteroaryl units which can serve as part of a linking group, for example, units having the formula:

 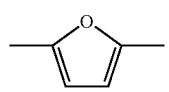

which represent an arylene and heteroarylene unit respectively.

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit." The following are non-limiting examples of units which can serve as a replacement for hydrogen atoms when a hydrocarbyl unit is described as "substituted."

i) —$[C(R^6)_2]_p(CH=CH)_qR^6$; wherein p is from 0 to 12; q is from 0 to 12;
ii) —$C(Z)R^6$;
iii) —$C(O)OR^6$
iv) —$C(Z)CH=CH_2$;
v) —$C(Z)N(R^6)_2$;
vi) —$C(Z)NR^6N(R^6)_2$;
vii) —CN;
viii) —C(O)OM
ix) —$CF_3$, —$CCl_3$, —$CBr_3$;
x) —$N(R^6)_2$;
xi) -halo
xii) —$NR^6C(Z)R^6$;
xiii) —$NR^6C(Z)N(R^6)_2$;
xiv) —$NR^6N(R^6)_2$;
xv) —$NHOR^6$;
xvi) —$OCF_3$, —$OCCl_3$, —$OCBr_3$;
xvii) —$NO_2$;
xviii) —$OR^6$;
xix) —$NR^6S(O)_2R^6$
xx) —$NR^6S(O)_2NR^6$
xxi) —$SO_2N(R^6)_2$
xxii) —$SO_2R^6$
xxiii) —$SO_3M$;
xxiv) —$OSO_3M$;
xxv) —$OP(O)(OM)_2$;
xxvi) —$P(O)(OR^6)_2$
xxvii) —$P(O)(OM)_2$
xxiii) —$OP(O)(OR^6)_2$
xxix) and mixtures thereof wherein $R^8$ is hydrogen, substituted or unsubstituted $C_1$–$C_{20}$ linear, branched, or cyclic alkyl, $C_6$–$C_{20}$ aryl, $C_7$–$C_{20}$ alkylenearyl, and mixtures thereof; M is hydrogen, or a salt forming cation; Z is =O, =S, =$NR^8$, and mixtures thereof. Suitable salt forming cations include, sodium, lithium, potassium, calcium, magnesium, ammonium, and the like. Non-limiting examples of an alkylenearyl unit include benzyl, 2-phenylethyl, 3-phenylpropyl, 2-phenylpropyl.

The compounds of the present invention include all enantiomeric and diasteriomeric forms and pharmaceutically acceptable salts of compounds having the core scaffold represented by the formula:

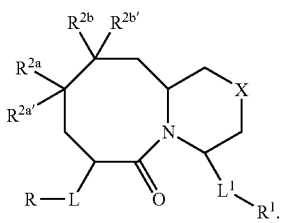

For the purposes of the present invention, when X is —O— or —NR⁹—, the following ring numbering system is used throughout the specification to identify the Interleukin-β converting enzyme (ICE) inhibitors of the present invention:

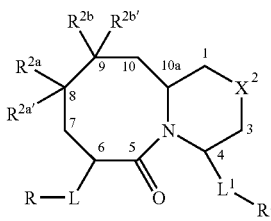

wherein $R^{2a'}$ and $R^{2b'}$ can also be taken together to form a double bond as described further herein below.

For the purposes of the present invention, when X is —CH$_2$—, the following ring numbering system is used throughout the specification to identify the lnterleukin-β converting enzyme (ICE) inhibitors of the present invention:

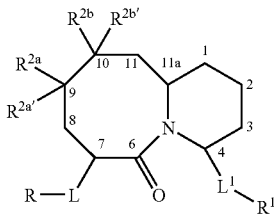

wherein $R^{2a'}$ and $R^{2b'}$ can also be taken together to form a double bond as described further herein below.

As it relates to the stereochemistry of the [8,6] fused ring systems of the present invention, when X is —O— or —NR⁹— the following stereochemical assignments are given for the ring positions utilizing the ring numbering system described herein above.

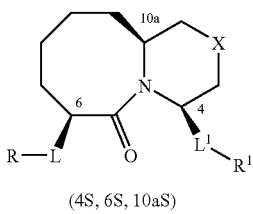

(4S, 6S, 10aS)

As it relates to the stereochemistry of the [8,6] fused ring systems of the present invention, when X is —CH$_2$— and an olefin is present in the 8-member ring, the priority of the carbon at 11a changes and therefore the following stereochemical assignments are given for the ring positions utilizing the ring numbering system described herein above.

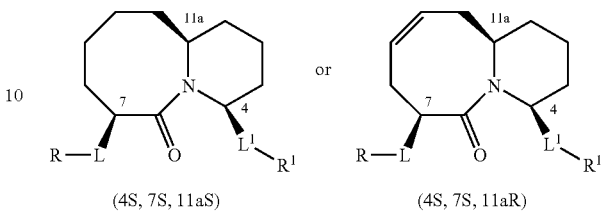

(4S, 7S, 11aS)   (4S, 7S, 11aR)

The analogs (compounds) of the present invention are arranged into several categories predicated on the form of the parent [8,6] fused ring system to assist the formulator in applying a rational synthetic strategy for the preparation of analogs which are not expressly exampled herein. The arrangement into categories does not imply increased or decreased efficacy for any of the compositions of matter described herein.

If necessary, the analogs (compounds) of the present invention are conveniently obtained in the salt form, for example, the trifluoroacetate salt. Also, the formulator, if convenient or practicable, can prepare a pro-drug which is capable of releasing the active compound (analog) upon uptake by the host. All of these variations are encompassed within the present invention.

As stated herein above, the form of the [8,6] fused ring scaffold indicates into which category the compounds of the present invention fall. Non-limiting examples of ring systems according to the present invention include:

i) 4,6-disubstituted 5-oxo-decahydro-2,4a-diaza-benzocyclooctene scaffold having the formula:

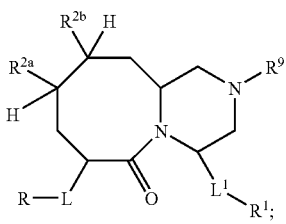

ii) 4,6-disubstituted 5-oxo-1,3,4,5,6,7,10,10a-octahydro-2H-2,4a-diaza-benzocyclooctene scaffold having the formula:

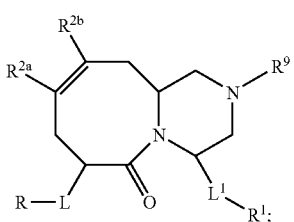

iii) 4,6-disubstituted 5-oxo-decahydro-2-oxa-4a-aza-benzo-cyclooctene scaffold having the formula:

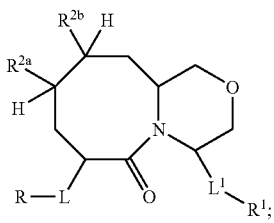

iv) 4,6-disubstituted 5-oxo-1,3,4,5,6,7,10,10a-octahydro-2-oxa-4a-aza-benzocyclooctene scaffold having the formula:

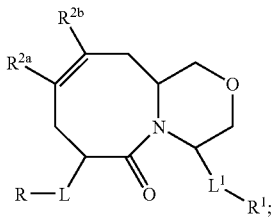

v) 4,7-disubstituted 6-oxo-decahydro-pyrido[1,2-a]azocine

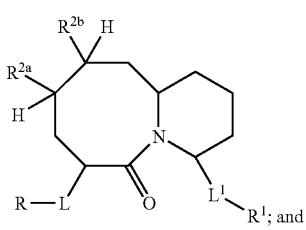

vi) 4,7-disubstituted-6-oxo-1,2,3,4,7,8,11,11a-octahydro-prido[1,2a]azocine scaffold having the formula

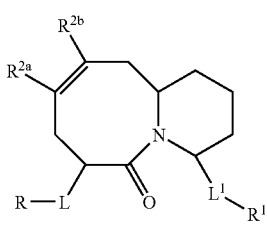

said scaffolds comprising the R, $R^1$ $R^{2a}$, $R^{2a'}$, $R^{2b}$, $R^{2b'}$, L, and $L^1$ units as described herein.

The compounds of the present invention include all enantiomeric and diasteriomeric forms and pharmaceutically acceptable salts of compounds having the core scaffold represented by the formula:

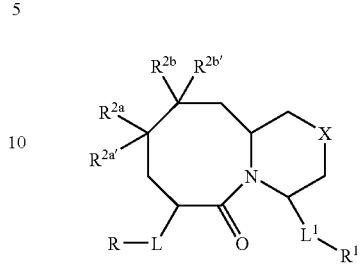

wherein X is —$CH_2$—, —O—, or —$NR^9$—.

R is a carbocyclic or heterocyclic ring.

The first aspect of R relates to substituted or unsubstituted carbocyclic rings.

The first embodiment of this aspect relates to substituted and unsubstituted aryl units, inter alia, phenyl and naphthyl rings. The first iteration of this embodiment relates to substituted aryl rings comprising at least one halogen atom, non-limiting examples of which includes 2-fluorophenyl, 3-fluorophenyl, 4-fluorophenyl, 3-fluoro-4-methylphenyl, 3-fluoro-4-methoxyphenyl, 3-chloro-2-methylphenyl, 3-chloro-6-methylphenyl, 3-chloro-4-methoxyphenyl, 3-chloro-4-hydroxyphenyl, 3,5-difluorophenyl, 2,6-dichlorophenyl, 2-chlorophenyl, 3-chlorophenyl, 4-chlorophenyl, 3,4-dichlorophenyl, 3,5-dichlorophenyl, 3-chloro-4-fluorophenyl, 2-bromophenyl, 3-bromophenyl, 4-bromophenyl, and the like.

A second iteration of this embodiment relates to $C_1$–$C_4$ alkyl substituted aryl units non-limiting examples of which include 2-methylphenyl, 3-methylphenyl, 4-methylphenyl, 3,5-dimethylphenyl, 2-ethylphenyl, 3-ethylphenyl, 4-ethylphenyl, 3-ethyl-4-methylphenyl 3-propylphenyl, 3-butylphenyl, and the like.

A third iteration of this embodiment relates to $C_1$–$C_4$ alkoxy substituted aryl units non-limiting examples of which include 2-methoxyphenyl, 3-methoxyphenyl, 4-methoxyphenyl, 2-ethoxyphenyl, 3-ethoxyphenyl, 4-ethoxyphenyl, 4-propoxyphenyl, 4-butoxyphenyl, 3,4,5-trimethoxyphenyl, and the like.

A fourth iteration of this embodiment relates to amino substituted aryl units non-limiting examples of which include 3-aminonaphth-2-yl, 4-dimethylaminonaphth-1-yl, 2-aminophenyl, 3-aminophenyl, 4-aminophenyl, 3,4-dimethylaminophenyl, 4-amino-3-chlorophenyl, 4-amino-3,5-dichlorophenyl, 4-dimethylaminophenyl, 2-acetylaminophenyl, 3-acetylaminophenyl, 4-acetylaminophenyl, 4-lsobutyrylaminophenyl, 4-propionylamino-phenyl, 4-butrylaminophenyl, 4-phenylacetylaminophenyl, 3,4-diacetylaminophenyl, 4-(N-acetyl-N-methylamino)-phenyl, 4-benzoylaminophenyl, and the like.

A fifth iteration of this embodiment relates to other substituted and unsubstituted aryl units non-limiting examples of which include 2-trifluoromethylphenyl, 3-trifluoromethylphenyl, 4-trifluoromethylphenyl, 4-hydroxymethyl-phenyl, naphth-1-yl, naphth-2-yl, 4-biphenyl, 4-phenoxyphenyl, 4-(3-methyl-ureido)-phenyl, 4-sulfamoylphenyl, 3-acetylphenyl, 4-acetylphenyl, 3-hydroxyphenyl, 4-hydroxyphenyl, 4-benzyloxyphenyl, 4-methanesulfonyl-phenyl, and the like.

Non-limiting examples of compounds according to the present invention which comprise the above identified R units include:

(4S,6S,10aS)-2-Benzenesulfonyl-6-[(isoquinoline-1-carbonyl)amino]-5-oxo-decahydro-2,4a-diaza-benzocyclooctene-4-carboxylic acid (2-hydroxy-5-oxo-tetrahydrofuran-3-yl)-amide;

(4S,6S,10aS)-2-Methanesulfonyl-6-[(naphthalene-2-carbonyl)amino]-5-oxo-decahydro-2,4a-diaza-benzocyclooctene-4-carboxylic acid (2-hydroxy-5-oxo-tetrahydrofuran-3-yl)-amide;

(4S,6S,10aS)-6-(3-Chlorobenzoylamino)-5-oxo-1,3,4,5,6,7,10,10a-octahydro-2-oxa-4a-diaza-benzocyclooctene-4-carboxylic acid (2-hydroxy-5-oxo-tetrahydrofuran-3-yl)-amide;

(4S,6S,10aS)-6-[(Benzo[b]thiophene-2-carbonyl)amino]-5-oxo-1,3,4,5,6,7,10,10a-octahydro-2-oxa-4a-diaza-benzocyclooctene-4-carboxylic acid (2-hydroxy-5-oxo-tetrahydrofuran-3-yl)-amide;

(4S,7S,11aR)-6-Oxo-7-(3-trifluoromethylbenzyolamino)-1,3,4,6,7,8,11,11a-octahydro-2H-pyrido[1,2-a]azocine-4-carboxylic acid (2-hydroxy-5-oxo-tetrahydrofuran-3-yl)-amide;

(4S,7S,11aR)-6-Oxo-7-benzyolamino-1,3,4,6,7,8,11,11a-octahydro-2H-pyrido[1,2-a]azocine-4-carboxylic acid (2-hydroxy-5-oxo-tetrahydrofuran-3-yl)-amide.

A second embodiment of this aspect relates to R units which are non-aryl carbocyclic units, inter alia, cyclopropyl, cyclobutyl, cyclohexyl, cyclopentyl, cyclohexenyl, cyclopentenyl, and the like.

The second aspect of R relates to substituted or unsubstituted heterocyclic rings. The second embodiment of this aspect relates to other substituted and unsubstituted monocyclic heteroaryl rings, inter alia, thiophene, furanyl and pyrimidine rings. The first iteration of this embodiment relates to substituted and unsubstituted monocyclic pyridinyl systems, non-limiting examples of which include, pyridin-2-yl, pyridin-3-yl, pyridin-4-yl, 3-chloropyridin-2-yl, 4-chloropyridin-2-yl, 5-chloropyridin-2-yl, 6-chloropyridin-2-yl, 3-methylpyridin-3-yl, 4-methylpyridin-3-yl, 5-methylpyridin-3-yl, vinyl pyridin-4-yl, vinyl pyridin-3-yl, and the like.

The second iteration of this embodiment relates to other substituted and unsubstituted monocyclic heteroaryl ring systems, non-limiting examples of which include, thiophen-3-yl, thiophen-2-yl, pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, 2-ethyl-5-methyl-2H-pyrazol-3-yl, 2,4-dimethyl-thiazol-5-yl, 5-methylisoxazol-3-yl, 1H-imidazol-2-yl, [1,2,3]thiadiazol-5-yl, furan-2-yl, furan-3-yl, 4,5-dimethyl-2-furanyl, 5-bromo-2-furanyl, 2-phenylamino-pyrimidin-4-yl, and the like The third iteration of this embodiment relates to substituted and unsubstituted heteroaryl fused ring systems, non-limiting examples of which include quinolin-2-yl, quinolin-3-yl, quinolin-4-yl, quinolin-5-yl, quinolin-8-yl, isoquinolin-1-yl, isoquinolin-3-yl, 1,2,3,4-tetrahydro-quinolin-2-yl, 1,2,3,4-tetrahydro-quinolin-3-yl, benzofuran-2-yl, benzofuran-3-yl, benzofuran-5-yl, 1H-indol-5-yl, benzo[b]thiophen-5-yl, benzo[b]thiophen-3-yl, benzo[b]thiophen-2-yl, 3H-benzotriazol-5-yl, 1-methyl-1H-indol-2-yl, 3H-benzimidazol-5-yl, 4-methoxy-quinolin-2-yl, thieno[2,3-b]thiophen-2-yl and the like.

A second embodiment of the heterocyclic ring aspect of R relates to substituted and unsubstituted non aromatic heterocyclic rings, non-limiting examples of which include pyrrolidin-1-yl, piperidin-1-yl, piperidin-4-yl, piperazin-1-yl, and the like.

$R^1$ is a cysteine trap. The cysteine traps of the present invention can be in either the bio-active or the bio-equivalent form.

Without wishing to be limited by theory, the compounds of the present invention are capable of selectively inhibiting the activity of certain cysteine protease enzymes, inter alia, Caspase-1 enzyme (ICE). Although similar, the active sights of the various cysteine proteases are different enough that although the mechanism of interaction between "cysteine traps" and the various cysteine protease enzymes may be roughly equivalent, the combination of a specific cysteine trap, scaffold, and R unit according to the present invention provides enhanced specificity for certain enzymes. Caspase-1, for example, is an enzyme which is capable of acting to release Interleukin-1β which then diffuses out of the cell. Caspase-1 is believed to comprise an active site which comprises the thio (—SH) of a cysteine amino acid associated with at amino acid position 285 of the Caspase-1 enzyme. It is the thio moiety of this cysteine which reacts reversibly or irreversibly with the second reactive moiety of the cysteine traps which comprise the compounds of the present invention. It is therefore believed it is the R unit and 8,6-fused ring scaffold portion of the molecule which aligns the trap in a manner which is favorable to reacting with Caspase-1 enzyme over other cysteine proteases.

As stated herein above, the cysteine traps of the present invention may be reversible or irreversible traps. The following is a non-limiting description of cysteine traps according to the present invention.

Reversible Cysteine Traps

The first category of $R^1$ units are reversible cysteine traps, the first aspect of which relates to cyclic iterations of these traps and the bio-active and bio-equivalent embodiments thereof. These traps are referred to collectively herein as "lactol" cysteine traps whether said traps are in the bio-active form which interacts reversibly with cysteine protease enzymes or in the bio-equivalent form. These lactols have the general formula:

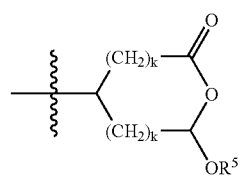

wherein $R^5$ is hydrogen (bioactive form), $C_1$–$C_4$ alkyl, substituted or unsubstituted $C_6$–$C_{10}$ aryl and alkylenearyl, inter alia, phenyl, benzyl (bio-equivalent forms) and the each index k is independently 0, 1, or 2. One iteration of this aspect relates to the aspartate traps, one of which has the following bio-active forms which exist in equilibrium depending upon the medium into which they are dissolved.

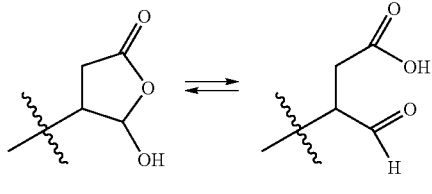

However, the bio-active form is the form which is present when enzyme inhibition occurs whether in vitro or in vivo.

An example of a bio-equivalent form of this trap has the formula:

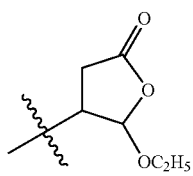

and which must be reverted to the above described bio-active form prior to interaction with the target enzyme.

Non-limiting examples of the bio-active and bio-equivalent forms of suitable cysteine traps which comprise the first aspect of $R^1$ units include:

a)

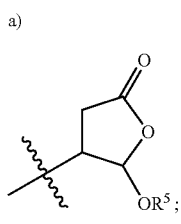

b)

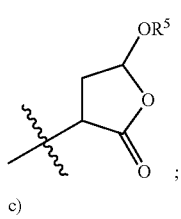

c)

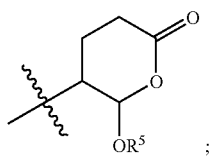

d)

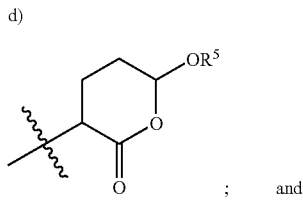

and

-continued e)

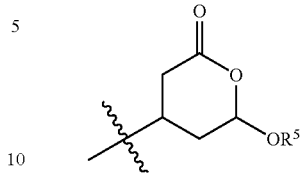

wherein $R^5$ is the same as defined herein above. As described herein below, the bio-equivalent forms of the aspartyl or glutamyl traps can be prepared according to Chapman, K. T. *Bioorganic Med. Chem. Lett.*, 2(6), 1992, pp. 613–618. included herein by reference.

A second aspect of $R^1$ units, which are reversible cysteine traps, relates to open form embodiments of said traps having the formula:

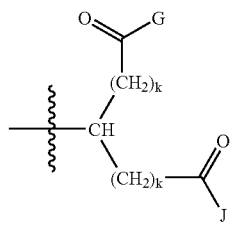

wherein G is —OH or a labile unit and J is a unit selected from the group:
  i) hydrogen;
  ii) substituted or unsubstituted aryl;
  iii) substituted or unsubstituted alkylenearyl;
  iv) substituted or unsubstituted heteroaryl;
  v) —CH$_2$N(R$^{21}$)$_2$;
  vi) —C(O)R$^{21}$;
  vii) —C(O)N(R$^{21}$)$_2$; and
  viii) —C(O)OR$^{21}$;

R$^{21}$ is hydrogen, substituted or unsubstituted aryl, substituted or unsubstituted alkylenearyl, and substituted or unsubstituted heteroaryl.

The first iteration of this second aspect encompasses reversible cysteine traps, wherein the first reactive moiety (carboxylate unit) comprises a unit having the formula:

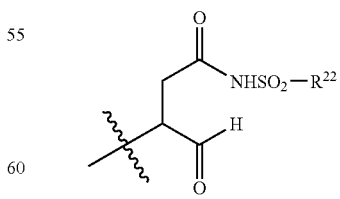

wherein R$^{22}$ is C$_1$–C$_4$ alkyl.

A second iteration of this aspect relates to cysteine traps wherein G is a —OH moiety, said traps having the general formula:

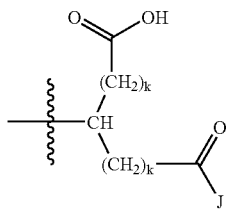

wherein J is an alkylenearyl unit having the formula —(CH$_2$)$_u$R$^{23}$; R$^{23}$ is a substituted or unsubstituted aryl unit, inter alia, phenyl, naphthyl, and the like; the index u is from 0 to 10. Non-limiting examples of suitable J units include alkylenearyl units wherein the index u is selected from the group consisting of 1, 2, 3, 4, and 5: benzyl, 2-phenylethyl, 3-phenylpropyl, 4-phenylbutyl, and 5-phenylpentyl.

A further iteration of this aspect relates to cysteine traps wherein J is a unit having the formula —N(R$^{21}$)$_2$ and one R$^{21}$ is hydrogen and the other is an alkylenearyl unit. A non-limiting example of a generic Category II scaffold coupled to a cysteine trap encompassed by this embodiment has the formula:

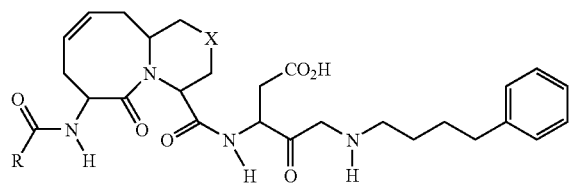

wherein R is the same as defined herein above and X is —NR$^9$ as defined herein above.

A third iteration of this aspect relates to cysteine traps wherein J is an alkylenearyl unit. A non-limiting example of a generic Category II scaffold coupled to a cysteine trap encompassed by this embodiment has the formula:

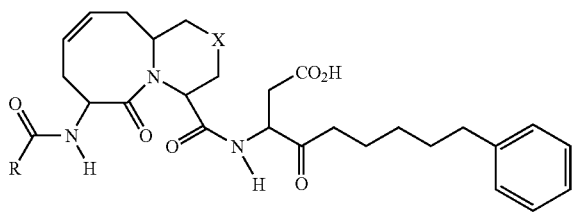

wherein R is the same as defined herein above and X is —NR$^9$ as defined herein above.

A third aspect of R$^1$ units which are reversible cysteine traps relates to α,α-difluoro ketones having the formula:

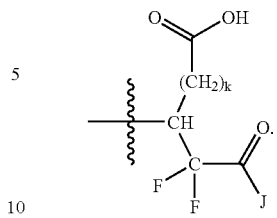

A non-limiting example of a generic Category II scaffold coupled to a α,α-difluoro ketone cysteine trap encompassed by this aspect has the formula:

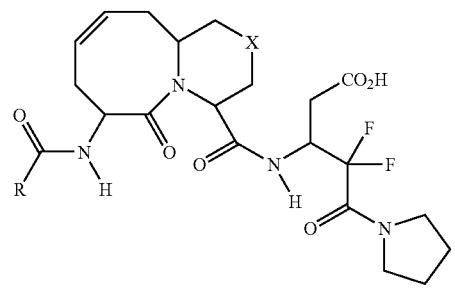

wherein R is the same as defined herein above and X is —NR$^9$ as defined herein above.

The second category of R$^1$ units encompasses irreversible binding cysteine traps. These traps act in a manner described in and known throughout the prior art as "suicide" binding units because of their irreversible effect in stopping an enzyme from maintaining activity or maturing the release of cytokines. The first aspect of this category are carboxy methylene units having the formula:

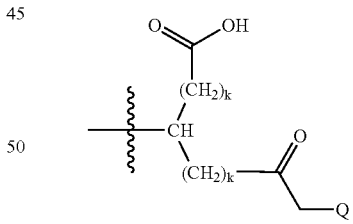

wherein Q is a leaving group selected from:
i) substituted or unsubstituted heterocyclic or heteroaryl;
ii) —OC(O)R$^{11}$;
iii) —NHSO$_2$R$^{12}$;
iv) —ONR$^{13}$C(O)R$^{13}$;
v) halogen;
vi) —NHC(O)OR$^{14}$;
vii) —NHC(O)NHR$^{15}$;
ix) —OR$^{16}$;
X) —SR$^{17}$;
xi) —SSR$^{18}$;
xii) —SSO$_3$R$^{19}$; and xiii) —OP(O)(R$^{20}$)$_2$;

wherein R$^{11}$ is C$_6$–C$_{10}$ aryl, for example, phenyl, naphtha-1-yl; C$_7$–C$_{20}$ alkylenearyl, for example, benzyl; —NHR$^{24}$; R$^{24}$ is C$_1$–C$_4$ alkyl; R$^{12}$ is C$_1$–C$_{12}$ linear, branched, or cyclic alkyl; R$^{13}$ is hydrogen, C$_1$–C$_4$ alkyl, substituted or unsubstituted C$_6$–C$_{10}$ aryl, substituted or unsubstituted C$_7$–C$_{20}$ alkylenearyl, or two R$^{13}$ units can be taken together to form a fused or no-fused ring having from 3 to 12 atoms; R$^{14}$ is substituted or unsubstituted C$_6$–C$_{10}$ aryl or substituted or unsubstituted C$_7$–C$_{20}$ alkylenearyl; R$^{15}$ is C$_1$–C$_4$ alkyl, substituted or unsubstituted C$_6$–C$_{10}$ aryl, and substituted or unsubstituted C$_7$–C$_{20}$ alkylenearyl; R$^{16}$ is C$_1$–C$_4$ alkyl; R$^{17}$ and R$^{18}$ are substituted or unsubstituted C$_6$–C$_{10}$ aryl, and substituted or unsubstituted C$_7$–C$_{20}$ alkylenearyl; R$^{19}$ is hydrogen, C$_1$–C$_4$ alkyl, substituted or unsubstituted C$_6$–C$_{10}$ aryl, and substituted or unsubstituted C$_7$–C$_{20}$ alkylenearyl; R$^{20}$ is substituted or unsubstituted C$_6$–C$_{10}$ aryl, and substituted or unsubstituted C$_7$–C$_{20}$ alkylenearyl.

The first aspect of this category of irreversible cysteine traps relates to acyloxy ketones having the formula:

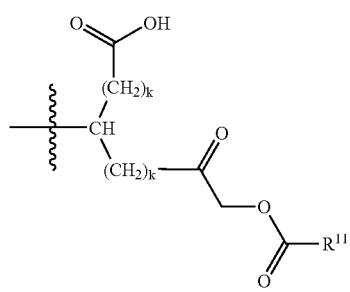

wherein R$^{11}$ is a substituted aryl unit, for example, 2,6-dimethylphenyl, 2,6-dichlorophenyl, and the like; the index k is the same as defined herein above. A non-limiting example of a generic Category II scaffold coupled to a cysteine trap encompassed by this aspect has the formula:

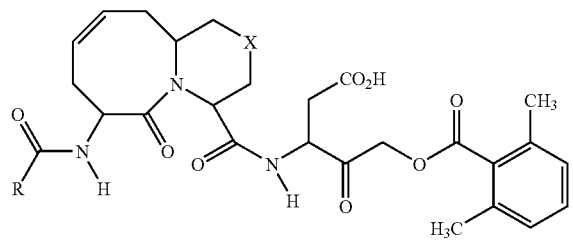

wherein R is the same as defined herein above and X is —NR$^9$ as defined herein above.

A further aspect relates to cysteine traps wherein J is a unit having the formula —ONR$^{13}$C(O)R$^{13}$ wherein two R$^{13}$ units can be taken together to form a fused. A non-limiting example of a generic Category II scaffold coupled to a cysteine trap encompassed by this embodiment has the formula:

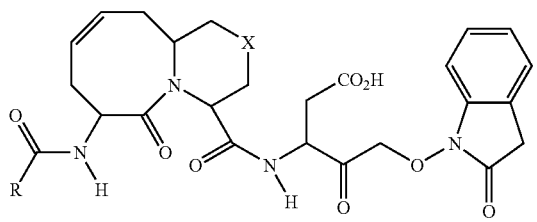

wherein R is the same as defined herein above and X is —NR$^9$ as defined herein above.

A third aspect of Category II cysteine traps relates to units wherein Q is a substituted or unsubstituted heterocyclic or heteroaryl unit. A non-limiting example of a generic Category II scaffold coupled to a cysteine trap encompassed by this embodiment has the formula:

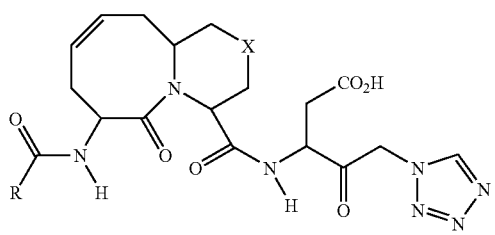

wherein R is the same as defined herein above and X is —NR$^9$ as defined herein above. Other heteroaryl units include substituted and unsubstituted isoxazoly, thiazolyl, imidazolyl, benzoxazolyl, and isoxazolinyl. Non-limiting examples include:

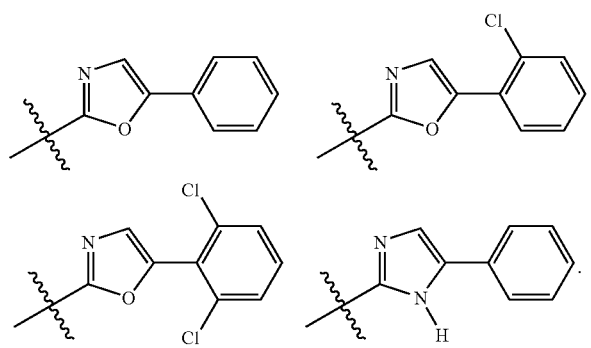

The second aspect of R$^1$ units encompassing irreversible binding cysteine traps are unsaturated compounds having the formula:

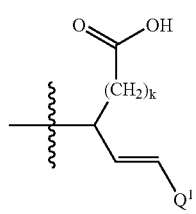

wherein $Q^1$ is a unit having the formula:
i) —C(O)$R^{24}$;
ii) —C(O)N($R^{24}$)$_2$; or
iii) —C(O)O$R^{24}$;

the first iteration of which has the formula:

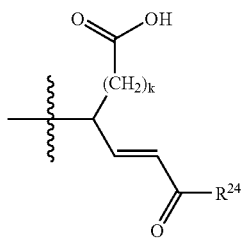

wherein $R^{24}$ is —O$R^{25}$ or —NH$R^{25}$ wherein $R^{25}$ is substituted or unsubstituted $C_6$–$C_{10}$ aryl or substituted or unsubstituted $C_7$–$C_{20}$ alkylenearyl. A non-limiting example of a generic Category II scaffold coupled to a cysteine trap encompassed by this iteration of the second aspect of $R^1$ units encompassing irreversible binding cysteine traps has the formula:

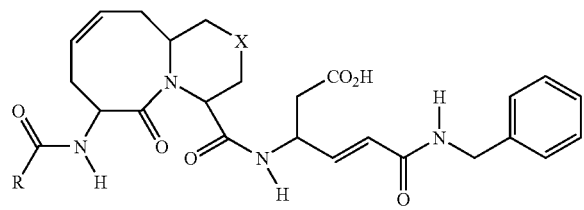

wherein R is the same as defined herein above and X is —N$R^9$ as defined herein above.

L, $L^1$, and $L^2$ are linking groups which serve to link the R, $R^1$, and $R^9$ units to the main [8,6] fused ring scaffold, said linking groups having the formula:

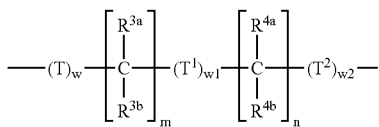

T, $T^1$, and $T^2$ are each independently selected from the group consisting of:
i) —N$R^6$—;
ii) —O—;
iii) —S(O)$_2$—;
iv) —N$R^6$S(O)$_2$—;
v) —S(O)$_2$N$R^6$—; and
vi) mixtures thereof;

w, $w^1$, and $w^2$ are each independently 0 or 1.

$R^{3a}$, $R^{3b}$, $R^{4a}$, and $R^{4b}$ are each independently
i) hydrogen;
ii) $C_1$–$C_4$ linear, branched, and cyclic alkyl;
iii) $R^{3a}$ and $R^{3b}$ or $R^{4a}$, and $R^{4b}$ can be taken together to form a carbonyl unit;

iv) two $R^{3a}$ or two $R^{3b}$ units from adjacent units or two $R^{4a}$ or two $R^{4b}$ units from adjacent units can be taken together to form a double bond; and
v) mixtures thereof;

$R^6$ is hydrogen, substituted or unsubstituted $C_1$–$C_{10}$ linear, branched, or cyclic alkyl, $C_6$–$C_{10}$ aryl, $C_7$–$C_{12}$ alkylenearyl, and mixtures thereof; the index m is from 0 to 5; the index n is from 0 to 5; the indices w, $w^1$, and $w^2$ are each independently 0 or 1. Each value of the indices m and n represent a distinct —C($R^{3a}R^{3b}$)— or —C($R^{4a}R^{4b}$)— unit. As described further herein below, a first —C($R^{3a}R^{3b}$)— may define a carbonyl unit in the linking unit while a second —C($R^{3a}R^{3b}$)— unit may be defined as a methylene unit: —CH$_2$—.

Examples of linking units according to the present invention include L units wherein:

i) the indices n, w, and $w^2$ are each equal to 0; $w^1$ is equal to 1, $T^1$ is —NH—, m is equal to 1, $R^{3a}$ and $R^{3b}$ are taken together to form a carbonyl unit, said L unit having the formula:

—C(O)NH—;

ii) the indices m, n, and w are each equal to 0; $w^1$ and $w^2$ are equal to 1, $T^1$ is —SO$_2$— and $T^2$ is equal to —NH—, said L unit having the formula:

—SO$_2$NH—;

iii) the indices w and $w^1$ are each equal to 0; $w^2$ is equal to 1, $T^2$ is —NH—, m and n are each equal to 1, $R^{3a}$ and $R^{3b}$ are taken together to form a carbonyl unit; and $R^{4a}$ and $R^{4b}$ are taken together to form a carbonyl unit, said L unit having the formula:

—C(O)C(O)NH—;

iv) the indices m, n, w and $w^2$ are each equal to 0; $w^1$ is equal to 1, $T^1$ is —NH—, said L unit having the formula:

—NH—;

v) the indices m and w are each equal to 0; $w^1$ and $w^2$ are each equal to 1, $T^1$ and $T^2$ are each —NH—, n is equal to 1, $R^{4a}$ and $R^{4b}$ are taken together to form a carbonyl unit, said L unit having the formula:

—NHC(O)NH—;

vi) the indices m and w are each equal to 0; $w^1$ and $w^2$ are each equal to 1, $T^1$ is equal to —O—; $T^2$ is equal to —NH—, n is equal to 1, $R^{4a}$ and $R^{4b}$ are taken together to form a carbonyl unit, said L unit having the formula:

—OC(O)NH—;

vii) the indices w and $w^1$ are each equal to 0; the index $w^2$ is equal to 1; $T^2$ is equal to —NH—; m is equal to 2, each $R^{3a}$ and $R^{3b}$ unit is hydrogen; n is equal to 1, $R^{4a}$ and $R^{4b}$ are taken together to form a carbonyl unit, said L unit having the formula:

—CH$_2$CH$_2$C(O)NH—;

viii) the indices w and $w^1$ are each equal to 0; the index $w^2$ is equal to 1; $T^2$ is equal to —NH—; m is equal to 2, each $R^{3a}$ unit is hydrogen, $R^{3b}$ from the first unit and $R^{3b}$ from the second unit are taken together to form a double bond; n is equal to 1, $R^{4a}$ and $R^{4b}$ are taken together to form a carbonyl unit, said L unit having the formula:

—CH=CHC(O)NH—.

$L^1$ units are formed in the same manner and can comprise the same or different units than L. For example, when L is —C(O)NH—, the unit $L^1$ can also be —C(O)NH—; $L^1$ can be any compatible unit.

$L^2$ units are formed in the same manner and can comprise the same or different units than L and $L^1$. $L^2$ units are present when X is —N-$L^2$-$R^{10}$, further described herein below.

The first aspect of linking units relates to the groups selected from the group consisting of:
i) —C(O)NH—;
ii) —NHC(O)—;
iii) —NHC(O)NH—;
iv) —C(O)C(O)—;
v) —C(O)—;
vi) —C(O)O—;
vii) —OC(O)—;
viii) —NH—;
ix) —NHS(O)$_2$—;
x) —S(O)$_2$NH—;
xi) —S(O)$_2$—;
xii) and mixtures thereof.

The first iteration of the linking units which comprise the first aspect of linking units, relates to compounds having the following scaffolds comprising L, $L^1$, and $L^2$ units, wherein L and $L^1$ each are equal to —C(O)NH—; for example, compounds having the formula:

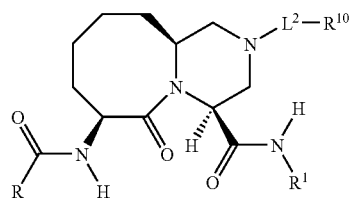

and $L^2$ can be any unit of the first aspect.

The second iteration of the linking units which comprise the first aspect of linking units, relates to compounds having the following scaffold comprising L, $L^1$, and $L^2$ units, wherein L and $L^1$ each are equal to —C(O)NH—; for example, compounds having the formula:

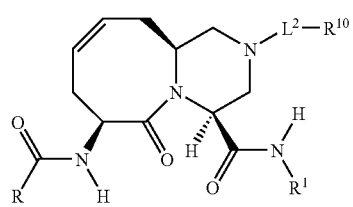

and $L^2$ can be any unit of the first aspect.

The third iteration of the linking units which comprise the first aspect of linking units, relates to compounds having the following scaffold comprising L and $L^1$ units, wherein L and $L^1$ each are equal to —C(O)NH—; for example, compounds having the formula:

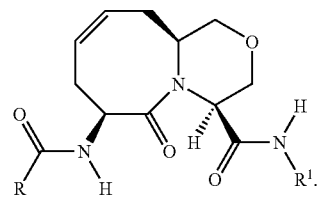

The fourth iteration of the linking units which comprise the first aspect of linking units, relates to compounds having the following scaffold comprising L and $L^1$ units, wherein L and $L^1$ each are equal to —C(O)NH—; for example, compounds having the formula:

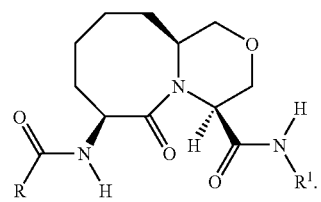

The fifth iteration of the linking units which comprise the first aspect of linking units, relates to compounds having the following scaffold comprising L and $L^1$ units, wherein L and $L^1$ each are equal to —C(O)NH—; for example, compounds having the formula:

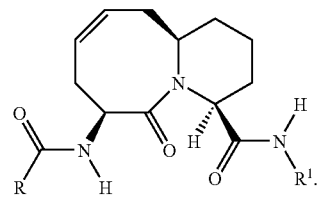

The sixth iteration of the linking units which comprise the first aspect of linking units, relates to compounds having the following scaffold comprising L and $L^1$ units, wherein L and $L^1$ each are equal to —C(O)NH—; for example, compounds having the formula:

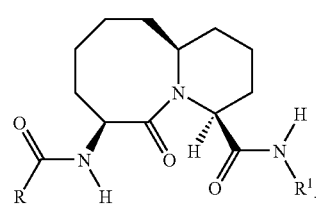

The following are examples of compounds which comprise iterations 1–6 of the first aspect of linking units disclosed in the general figures herein above:

I) 2-Acetyl-6-[(isoquinoline-1-carbonyl)amino]-5-oxo-decahydro-2,4a-diaza-benzocyclooctene-4-carboxylic acid (2-hydroxy-5-oxo-tetrahydro-furan-3-yl)-amide;

II) 2-Acetyl-6-[(isoquinoline-1-carbonyl)amino]-5-oxo-1,3,4,5,6,7,10,10,a-octahydro-2H-2,4a-diaza-benzocyclooctene-4-carboxylic acid (2-hydroxy-5-oxo-tetrahydro-furan-3-yl)-amide;
III) 6-[(3-Isoquinoline-1-carbonyl)amino]-5-oxo-1,3,4,5,6,7,10,10a-octahydro-2-oxa-4a-aza-benzocyclooctene-4-carboxylic acid (2-hydroxy-5-oxo-tetrahydro-furan-3-yl)-amide;
IV) 6-[(Isoquinoline-1-carbonyl)amino]-5-oxo-decahydro-2-oxa-4a-aza-benzocyclooctene-4-carboxylic acid (2-hydroxy-5-oxo-tetrahydro-furan-3-yl)-amide;
V) 7-[(Isoquinoline-1-carbonyl)amino]-6-oxo-1,3,4,6,7,8,11,11a-octahydro-2H-pyrido[1,2-a]azocine-4-carboxylic acid (2-hydroxy-5-oxo-tetrahydro-furan-3-yl)-amide;
VI) 7-[(Isoquinoline-1-carbonyl)amino]-6-oxo-decahydro-pyrido[1,2-a]azocine-4-carboxylic acid (2-hydroxy-5-oxo-tetrahydro-furan-3-yl)-amide.

The second aspect of linking groups relates to the modification of L while $L^1$ and $L^2$, when present, remain the same, for example, the first iteration of the first aspect of linking units relates to scaffolds having the formula:

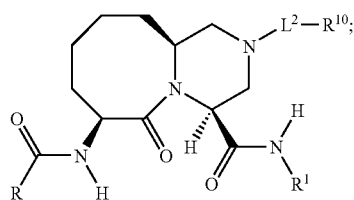

wherein L is —C(O)NH—. The second aspect of linking units relates to fixing the scaffold above as it relates to $L^1$ (in this example also —C(O)NH—) and $L^2$.

The first iteration of modifying L under the second aspect of linking units relates to scaffolds having the formula:

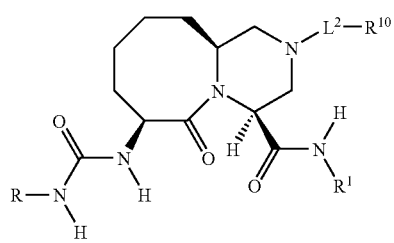

wherein L is equal to —NHC(O)—.

The second iteration of modifying L under the second aspect of linking units relates to scaffolds having the formula:

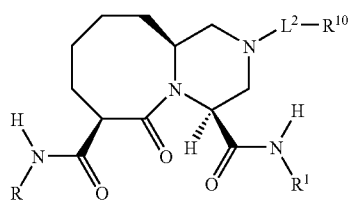

wherein L is equal to —NHC(O)NH—.

The third iteration of modifying L under the second aspect of linking units relates to scaffolds having the formula:

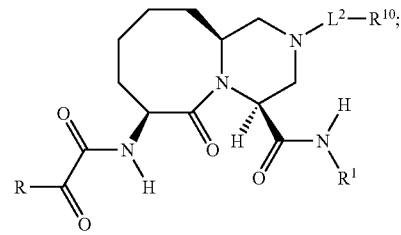

wherein L is equal to —C(O)C(O)NH—.

The fourth iteration of modifying L under the second aspect of linking units relates to scaffolds having the formula:

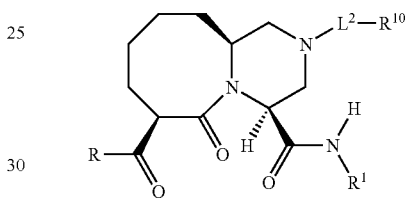

wherein L is equal to —C(O)—.

The fifth iteration of modifying L under the second aspect of linking units relates to scaffolds having the formula:

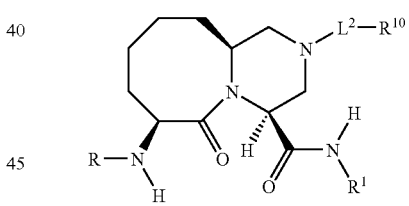

wherein L is equal to —NH—.

The sixth iteration of modifying L under the second aspect of linking units relates to scaffolds having the formula:

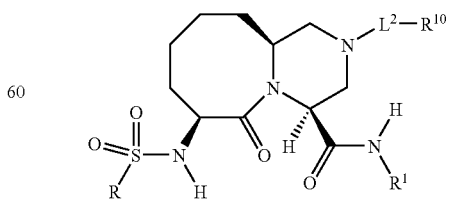

wherein L is equal to —$SO_2$NH—.

The seventh iteration of modifying L under the second aspect of linking units relates to scaffolds having the formula:

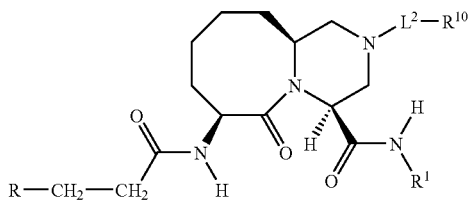

wherein L is equal to —CH$_2$CH$_2$C(O)NH—.

The eighth iteration of modifying L under the second aspect of linking units relates to scaffolds having the formula:

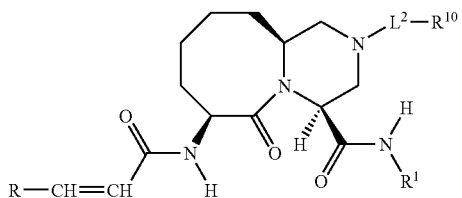

wherein L is equal to —CH=CHC(O)NH—.

The following are examples of compounds which comprise iterations 1–8 of the second aspect of linking units as disclosed in the general figures herein above.

I) 2-Acetyl-6-[(isoquinoline-1-carbonyl)amino]-5-oxo-decahydro-2,4a-diazabenzocycloocten-4-carboxylic acid (2-hydroxy-5-oxo-tetrahydro-furan-3-yl)-amide]-amide;

II) 2-Acetyl-6-(3-isoquinolin-1-yl-ureido)-5-oxo-decahydro-2,4a-diazabenzocycloocten-4-carboxylic acid (2-hydroxy-5-oxo-tetrahydro-furan-3-yl)-amide;

III) 2-Acetyl-7-(2-isoquinolin-1-yl-2-oxoacetylamino)-5-oxo-decahydro-2,4a-diazabenzocycloocten-4-carboxylic acid (2-hydroxy-5-oxo-tetrahydro-furan-3-yl)-amide;

IV) 2-Acetyl-7-(isoquinoline-1-carbonyl)-5-oxo-decahydro-2,4a-diazabenzocycloocten-4-carboxylic acid (2-hydroxy-5-oxo-tetrahydro-furan-3-yl)-amide;

V) 2-Acetyl-7-(isoquinolin-1-ylamino)-5-oxo-decahydro-2,4a-diazabenzocycloocten-4-carboxylic acid (2-hydroxy-5-oxo-tetrahydro-furan-3-yl)-amide;

VI) 2-Acetyl-7-(isoquinoline-1-sulfonylamino)-5-oxo-decahydro-2,4a-diazabenzo-cycloocten-4-carboxylic acid (2-hydroxy-5-oxo-tetrahydro-furan-3-yl)-amide;

VII) 2-Acetyl-7-(3-isoquinolin-1-ylpropionylamino)-5-oxo-decahydro-2,4a-diazabenzocycloocten-4-carboxylic acid (2-hydroxy-5-oxo-tetrahydro-furan-3-yl)-amide; and VII) 2-Acetyl-7-(3-isoquinolin-1-yl-acryloylamino)-5-oxo-decahydro-2,4a-diazabenzocycloocten-4-carboxylic acid (2-hydroxy-5-oxo-tetrahydro-furan-3-yl)-amide.

Another aspect of the linking units relates to [8,6]-fused ring systems wherein X is —NR$^9$—; R$^9$ is hydrogen or a unit having the formula -L$^2$-R$^{10}$; wherein L$^2$ is the same as defined herein above; R$^{10}$ is hydrogen; substituted or unsubstituted C$_1$–C$_6$ linear; branched, or cyclic hydrocarbyl; substituted or unsubstituted aryl; substituted or unsubstituted C$_1$–C$_9$ heterocyclic; and substituted or unsubstituted heteroaryl.

Category I and Category II compounds of the present invention comprise scaffolds wherein X is equal to —NR$^9$— units wherein R$^9$ is -L$^2$R$^{10}$ Category III and Category IV compounds of the present invention comprise scaffolds wherein X is —O—.

Category V and Category VI compounds of the present invention comprise scaffolds wherein X is —CH$_2$—.

Category I interleukin-1β converting enzyme inhibitors according to the present invention are compounds comprising a 2,4,6-substituted decahydro 2,4a-diazabenzocycloocten-5-one scaffold having the formula:

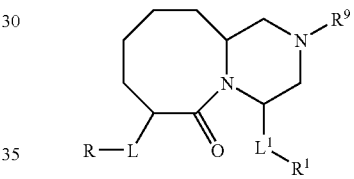

the first aspect of which comprises compounds having the scaffold with the formula and indicated stereochemistry:

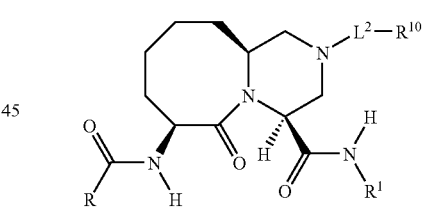

wherein R, R$^1$ and -L$^2$-R$^{10}$ are defined in Table I herein below.

TABLE I

| No. | R | R$^1$ | —L$^2$—R$^{10}$ |
|---|---|---|---|
| 1 | phenyl | 2-ethoxy-5-oxo-tetrahydrofuran-3-yl | —CH$_3$ |
| 2 | phenyl | 2-ethoxy-5-oxo-tetrahydrofuran-3-yl | —CH$_2$CH$_3$ |
| 3 | phenyl | 2-ethoxy-5-oxo-tetrahydrofuran-3-yl | —C(O)OCH$_2$C$_6$H$_5$ |
| 4 | phenyl | 2-ethoxy-5-oxo-tetrahydrofuran-3-yl | —C(O)CH$_3$ |
| 5 | phenyl | 2-ethoxy-5-oxo-tetrahydrofuran-3-yl | —SO$_2$CH$_3$ |
| 6 | phenyl | 2-ethoxy-5-oxo-tetrahydrofuran-3-yl | —SO$_2$CH$_2$CH$_3$ |
| 7 | phenyl | 2-ethoxy-5-oxo-tetrahydrofuran-3-yl | —SO$_2$CH(CH$_3$)$_2$ |
| 8 | phenyl | 2-ethoxy-5-oxo-tetrahydrofuran-3-yl | —SO$_2$C$_6$H$_5$ |
| 9 | phenyl | 2-ethoxy-5-oxo-tetrahydrofuran-3-yl | —C(O)C$_6$H$_5$ |
| 10 | phenyl | 2-ethoxy-5-oxo-tetrahydrofuran-3-yl | —C(O)NHC$_6$H$_5$ |

TABLE I-continued

| No. | R | R¹ | —L²—R¹⁰ |
|---|---|---|---|
| 11 | naphth-1-yl | 2-ethoxy-5-oxo-tetrahydrofuran-3-yl | —CH₃ |
| 12 | naphth-1-yl | 2-ethoxy-5-oxo-tetrahydrofuran-3-yl | —CH₂CH₃ |
| 13 | naphth-1-yl | 2-ethoxy-5-oxo-tetrahydrofuran-3-yl | —C(O)OCH₂C₆H₅ |
| 14 | naphth-1-yl | 2-ethoxy-5-oxo-tetrahydrofuran-3-yl | —C(O)CH₃ |
| 15 | naphth-1-yl | 2-ethoxy-5-oxo-tetrahydrofuran-3-yl | —SO₂CH₃ |
| 16 | naphth-1-yl | 2-ethoxy-5-oxo-tetrahydrofuran-3-yl | —SO₂CH₂CH₃ |
| 17 | naphth-1-yl | 2-ethoxy-5-oxo-tetrahydrofuran-3-yl | —SO₂CH(CH₃)₂ |
| 18 | naphth-1-yl | 2-ethoxy-5-oxo-tetrahydrofuran-3-yl | —SO₂C₆H₅ |
| 19 | naphth-1-yl | 2-ethoxy-5-oxo-tetrahydrofuran-3-yl | —C(O)C₆H₅ |
| 20 | naphth-1-yl | 2-ethoxy-5-oxo-tetrahydrofuran-3-yl | —C(O)NHC₆H₅ |
| 21 | naphth-2-yl | 2-ethoxy-5-oxo-tetrahydrofuran-3-yl | —CH₃ |
| 22 | naphth-2-yl | 2-ethoxy-5-oxo-tetrahydrofuran-3-yl | —CH₂CH₃ |
| 23 | naphth-2-yl | 2-ethoxy-5-oxo-tetrahydrofuran-3-yl | —C(O)OCH₂C₆H₅ |
| 24 | naphth-2-yl | 2-ethoxy-5-oxo-tetrahydrofuran-3-yl | —C(O)CH₃ |
| 25 | naphth-2-yl | 2-ethoxy-5-oxo-tetrahydrofuran-3-yl | —SO₂CH₃ |
| 26 | naphth-2-yl | 2-ethoxy-5-oxo-tetrahydrofuran-3-yl | —SO₂CH₂CH₃ |
| 27 | naphth-2-yl | 2-ethoxy-5-oxo-tetrahydrofuran-3-yl | —SO₂CH(CH₃)₂ |
| 28 | naphth-2-yl | 2-ethoxy-5-oxo-tetrahydrofuran-3-yl | —SO₂C₆H₅ |
| 29 | naphth-2-yl | 2-ethoxy-5-oxo-tetrahydrofuran-3-yl | —C(O)C₆H₅ |
| 30 | naphth-2-yl | 2-ethoxy-5-oxo-tetrahydrofuran-3-yl | —C(O)NHC₆H₅ |
| 31 | isoquinolin-1-yl | 2-ethoxy-5-oxo-tetrahydrofuran-3-yl | —CH₃ |
| 32 | isoquinolin-1-yl | 2-ethoxy-5-oxo-tetrahydrofuran-3-yl | —CH₂CH₃ |
| 33 | isoquinolin-1-yl | 2-ethoxy-5-oxo-tetrahydrofuran-3-yl | —C(O)OCH₂C₆H₅ |
| 34 | isoquinolin-1-yl | 2-ethoxy-5-oxo-tetrahydrofuran-3-yl | —C(O)CH₃ |
| 35 | isoquinolin-1-yl | 2-ethoxy-5-oxo-tetrahydrofuran-3-yl | —SO₂CH₃ |
| 36 | isoquinolin-1-yl | 2-ethoxy-5-oxo-tetrahydrofuran-3-yl | —SO₂CH₂CH₃ |
| 37 | isoquinolin-1-yl | 2-ethoxy-5-oxo-tetrahydrofuran-3-yl | —SO₂CH(CH₃)₂ |
| 38 | isoquinolin-1-yl | 2-ethoxy-5-oxo-tetrahydrofuran-3-yl | —SO₂C₆H₅ |
| 39 | isoquinolin-1-yl | 2-ethoxy-5-oxo-tetrahydrofuran-3-yl | —C(O)C₆H₅ |
| 40 | isoquinolin-1-yl | 2-ethoxy-5-oxo-tetrahydrofuran-3-yl | —C(O)NHC₆H₅ |
| 41 | phenyl | 2-hydroxy-5-oxo-tetrahydrofuran-3-yl | —CH₃ |
| 42 | phenyl | 2-hydroxy-5-oxo-tetrahydrofuran-3-yl | —CH₂CH₃ |
| 43 | phenyl | 2-hydroxy-5-oxo-tetrahydrofuran-3-yl | —C(O)OCH₂C₆H₅ |
| 44 | phenyl | 2-hydroxy-5-oxo-tetrahydrofuran-3-yl | —C(O)CH₃ |
| 45 | phenyl | 2-hydroxy-5-oxo-tetrahydrofuran-3-yl | —SO₂CH₃ |
| 46 | phenyl | 2-hydroxy-5-oxo-tetrahydrofuran-3-yl | —SO₂CH₂CH₃ |
| 47 | phenyl | 2-hydroxy-5-oxo-tetrahydrofuran-3-yl | —SO₂CH(CH₃)₂ |
| 48 | phenyl | 2-hydroxy-5-oxo-tetrahydrofuran-3-yl | —SO₂C₆H₅ |
| 49 | phenyl | 2-hydroxy-5-oxo-tetrahydrofuran-3-yl | —C(O)C₆H₅ |
| 50 | phenyl | 2-hydroxy-5-oxo-tetrahydrofuran-3-yl | —C(O)NHC₆H₅ |
| 51 | naphth-1-yl | 2-hydroxy-5-oxo-tetrahydrofuran-3-yl | —CH₃ |
| 52 | naphth-1-yl | 2-hydroxy-5-oxo-tetrahydrofuran-3-yl | —CH₂CH₃ |
| 53 | naphth-1-yl | 2-hydroxy-5-oxo-tetrahydrofuran-3-yl | —C(O)OCH₂C₆H₅ |
| 54 | naphth-1-yl | 2-hydroxy-5-oxo-tetrahydrofuran-3-yl | —C(O)CH₃ |
| 55 | naphth-1-yl | 2-hydroxy-5-oxo-tetrahydrofuran-3-yl | —SO₂CH₃ |
| 56 | naphth-1-yl | 2-hydroxy-5-oxo-tetrahydrofuran-3-yl | —SO₂CH₂CH₃ |
| 57 | naphth-1-yl | 2-hydroxy-5-oxo-tetrahydrofuran-3-yl | —SO₂CH(CH₃)₂ |
| 58 | naphth-1-yl | 2-hydroxy-5-oxo-tetrahydrofuran-3-yl | —SO₂C₆H₅ |
| 59 | naphth-1-yl | 2-hydroxy-5-oxo-tetrahydrofuran-3-yl | —C(O)C₆H₅ |
| 60 | naphth-1-yl | 2-hydroxy-5-oxo-tetrahydrofuran-3-yl | —C(O)NHC₆H₅ |
| 61 | naphth-2-yl | 2-hydroxy-5-oxo-tetrahydrofuran-3-yl | —CH₃ |
| 62 | naphth-2-yl | 2-hydroxy-5-oxo-tetrahydrofuran-3-yl | —CH₂CH₃ |
| 63 | naphth-2-yl | 2-hydroxy-5-oxo-tetrahydrofuran-3-yl | —C(O)OCH₂C₆H₅ |
| 64 | naphth-2-yl | 2-hydroxy-5-oxo-tetrahydrofuran-3-yl | —C(O)CH₃ |
| 65 | naphth-2-yl | 2-hydroxy-5-oxo-tetrahydrofuran-3-yl | —SO₂CH₃ |
| 66 | naphth-2-yl | 2-hydroxy-5-oxo-tetrahydrofuran-3-yl | —SO₂CH₂CH₃ |
| 67 | naphth-2-yl | 2-hydroxy-5-oxo-tetrahydrofuran-3-yl | —SO₂CH(CH₃)₂ |
| 68 | naphth-2-yl | 2-hydroxy-5-oxo-tetrahydrofuran-3-yl | —SO₂C₆H₅ |
| 69 | naphth-2-yl | 2-hydroxy-5-oxo-tetrahydrofuran-3-yl | —C(O)C₆H₅ |
| 70 | naphth-2-yl | 2-hydroxy-5-oxo-tetrahydrofuran-3-yl | —C(O)NHC₆H₅ |
| 71 | isoquinolin-1-yl | 2-hydroxy-5-oxo-tetrahydrofuran-3-yl | —CH₃ |
| 72 | isoquinolin-1-yl | 2-hydroxy-5-oxo-tetrahydrofuran-3-yl | —CH₂CH₃ |
| 73 | isoquinolin-1-yl | 2-hydroxy-5-oxo-tetrahydrofuran-3-yl | —C(O)OCH₂C₆H₅ |
| 74 | isoquinolin-1-yl | 2-hydroxy-5-oxo-tetrahydrofuran-3-yl | —C(O)CH₃ |
| 75 | isoquinolin-1-yl | 2-hydroxy-5-oxo-tetrahydrofuran-3-yl | —SO₂CH₃ |
| 76 | isoquinolin-1-yl | 2-hydroxy-5-oxo-tetrahydrofuran-3-yl | —SO₂CH₂CH₃ |
| 77 | isoquinolin-1-yl | 2-hydroxy-5-oxo-tetrahydrofuran-3-yl | —SO₂CH(CH₃)₂ |
| 78 | isoquinolin-1-yl | 2-hydroxy-5-oxo-tetrahydrofuran-3-yl | —SO₂C₆H₅ |
| 79 | isoquinolin-1-yl | 2-hydroxy-5-oxo-tetrahydrofuran-3-yl | —C(O)C₆H₅ |
| 80 | isoquinolin-1-yl | 2-hydroxy-5-oxo-tetrahydrofuran-3-yl | —C(O)NHC₆H₅ |
| 81 | benzothiophen-2-yl | 2-hydroxy-5-oxo-tetrahydrofuran-3-yl | —CH₃ |
| 82 | benzothiophen-2-yl | 2-hydroxy-5-oxo-tetrahydrofuran-3-yl | —CH₂CH₃ |
| 83 | benzothiophen-2-yl | 2-hydroxy-5-oxo-tetrahydrofuran-3-yl | —C(O)OCH₂C₆H₅ |
| 84 | benzothiophen-2-yl | 2-hydroxy-5-oxo-tetrahydrofuran-3-yl | —C(O)CH₃ |
| 85 | benzothiophen-2-yl | 2-hydroxy-5-oxo-tetrahydrofuran-3-yl | —SO₂CH₃ |
| 86 | benzothiophen-2-yl | 2-hydroxy-5-oxo-tetrahydrofuran-3-yl | —SO₂CH₂CH₃ |
| 87 | benzothiophen-2-yl | 2-hydroxy-5-oxo-tetrahydrofuran-3-yl | —SO₂CH(CH₃)₂ |

TABLE I-continued

| No. | R | R¹ | —L²—R¹⁰ |
|---|---|---|---|
| 88 | benzothiophen-2-yl | 2-hydroxy-5-oxo-tetrahydrofuran-3-yl | —SO$_2$C$_6$H$_5$ |
| 89 | benzothiophen-2-yl | 2-hydroxy-5-oxo-tetrahydrofuran-3-yl | —C(O)C$_6$H$_5$ |
| 90 | benzothiophen-2-yl | 2-hydroxy-5-oxo-tetrahydrofuran-3-yl | —C(O)NHC$_6$H$_5$ |
| 91 | 3-chlorophenyl | 2-hydroxy-5-oxo-tetrahydrofuran-3-yl | —CH$_3$ |
| 92 | 3-chlorophenyl | 2-hydroxy-5-oxo-tetrahydrofuran-3-yl | —CH$_2$CH$_3$ |
| 93 | 3-chlorophenyl | 2-hydroxy-5-oxo-tetrahydrofuran-3-yl | —C(O)OCH$_2$C$_6$H$_5$ |
| 94 | 3-chlorophenyl | 2-hydroxy-5-oxo-tetrahydrofuran-3-yl | —C(O)CH$_3$ |
| 95 | 3-chlorophenyl | 2-hydroxy-5-oxo-tetrahydrofuran-3-yl | —SO$_2$CH$_3$ |
| 96 | 3-chlorophenyl | 2-hydroxy-5-oxo-tetrahydrofuran-3-yl | —SO$_2$CH$_2$CH$_3$ |
| 97 | 3-chlorophenyl | 2-hydroxy-5-oxo-tetrahydrofuran-3-yl | —SO$_2$CH(CH$_3$)$_2$ |
| 98 | 3-chlorophenyl | 2-hydroxy-5-oxo-tetrahydrofuran-3-yl | —SO$_2$C$_6$H$_5$ |
| 99 | 3-chlorophenyl | 2-hydroxy-5-oxo-tetrahydrofuran-3-yl | —C(O)C$_6$H$_5$ |
| 100 | 3-chlorophenyl | 2-hydroxy-5-oxo-tetrahydrofuran-3-yl | —C(O)NHC$_6$H$_5$ |
| 101 | 3-methylphenyl | 2-hydroxy-5-oxo-tetrahydrofuran-3-yl | —CH$_3$ |
| 102 | 3-methylphenyl | 2-hydroxy-5-oxo-tetrahydrofuran-3-yl | —CH$_2$CH$_3$ |
| 103 | 3-methylphenyl | 2-hydroxy-5-oxo-tetrahydrofuran-3-yl | —C(O)OCH$_2$C$_6$H$_5$ |
| 104 | 3-methylphenyl | 2-hydroxy-5-oxo-tetrahydrofuran-3-yl | —C(O)CH$_3$ |
| 105 | 3-methylphenyl | 2-hydroxy-5-oxo-tetrahydrofuran-3-yl | —SO$_2$CH$_3$ |
| 106 | 3-methylphenyl | 2-hydroxy-5-oxo-tetrahydrofuran-3-yl | —SO$_2$CH$_2$CH$_3$ |
| 107 | 3-methylphenyl | 2-hydroxy-5-oxo-tetrahydrofuran-3-yl | —SO$_2$CH(CH$_3$)$_2$ |
| 108 | 3-methylphenyl | 2-hydroxy-5-oxo-tetrahydrofuran-3-yl | —SO$_2$C$_6$H$_5$ |
| 109 | 3-methylphenyl | 2-hydroxy-5-oxo-tetrahydrofuran-3-yl | —C(O)C$_6$H$_5$ |
| 110 | 3-methylphenyl | 2-hydroxy-5-oxo-tetrahydrofuran-3-yl | —C(O)NHC$_6$H$_5$ |
| 111 | 3-fluorophenyl | 2-hydroxy-5-oxo-tetrahydrofuran-3-yl | —CH$_3$ |
| 112 | 3-fluorophenyl | 2-hydroxy-5-oxo-tetrahydrofuran-3-yl | —CH$_2$CH$_3$ |
| 113 | 3-fluorophenyl | 2-hydroxy-5-oxo-tetrahydrofuran-3-yl | —C(O)OCH$_2$C$_6$H$_5$ |
| 114 | 3-fluorophenyl | 2-hydroxy-5-oxo-tetrahydrofuran-3-yl | —C(O)CH$_3$ |
| 115 | 3-fluorophenyl | 2-hydroxy-5-oxo-tetrahydrofuran-3-yl | —SO$_2$CH$_3$ |
| 116 | 3-fluorophenyl | 2-hydroxy-5-oxo-tetrahydrofuran-3-yl | —SO$_2$CH$_2$CH$_3$ |
| 117 | 3-fluorophenyl | 2-hydroxy-5-oxo-tetrahydrofuran-3-yl | —SO$_2$CH(CH$_3$)$_2$ |
| 118 | 3-fluorophenyl | 2-hydroxy-5-oxo-tetrahydrofuran-3-yl | —SO$_2$C$_6$H$_5$ |
| 119 | 3-fluorophenyl | 2-hydroxy-5-oxo-tetrahydrofuran-3-yl | —C(O)C$_6$H$_5$ |
| 120 | 3-fluorophenyl | 2-hydroxy-5-oxo-tetrahydrofuran-3-yl | —C(O)NHC$_6$H$_5$ |

The compounds of Category I can be suitably prepared by the procedure outlined herein below, utilizing intermediate 6 which can be synthesized by the procedure described in Scheme I.

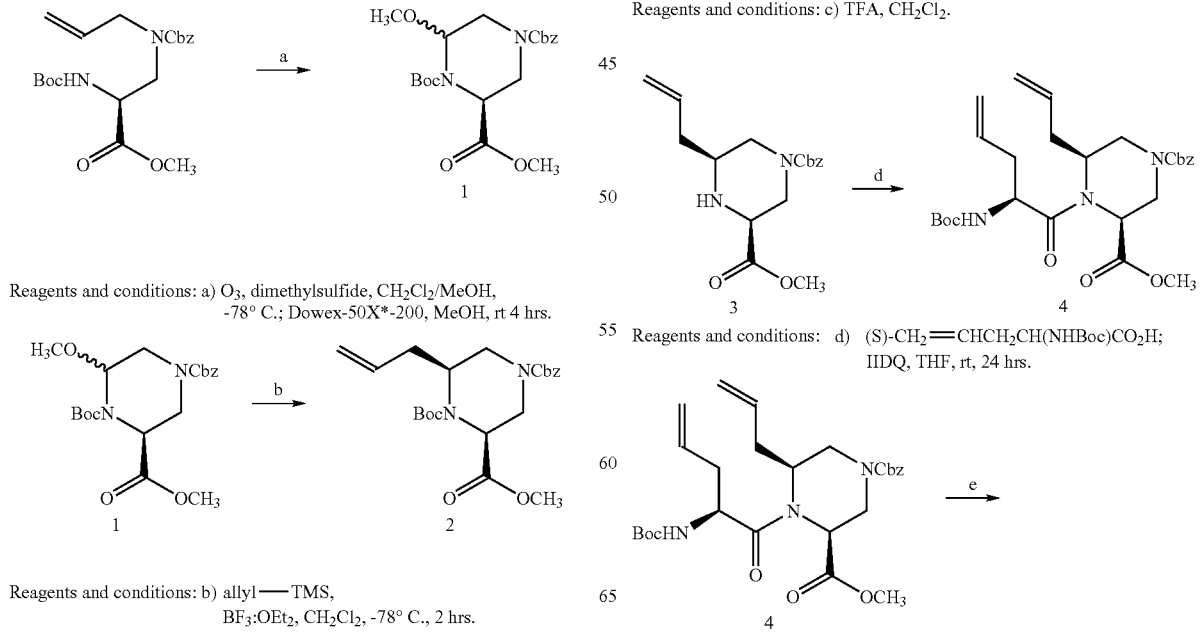

Scheme 1

Reagents and conditions: a) O$_3$, dimethylsulfide, CH$_2$Cl$_2$/MeOH, -78° C.; Dowex-50X*-200, MeOH, rt 4 hrs.

Reagents and conditions: b) allyl—TMS, BF$_3$:OEt$_2$, CH$_2$Cl$_2$, -78° C., 2 hrs.

Reagents and conditions: c) TFA, CH$_2$Cl$_2$.

Reagents and conditions: d) (S)-CH$_2$=CHCH$_2$CH(NHBoc)CO$_2$H; IIDQ, THF, rt, 24 hrs.

-continued

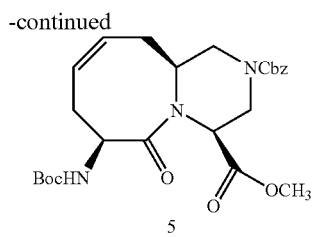

Reagents and Conditions: e) Grubbs catalyst; CH$_2$Cl$_2$, 40° C., 24 hrs.

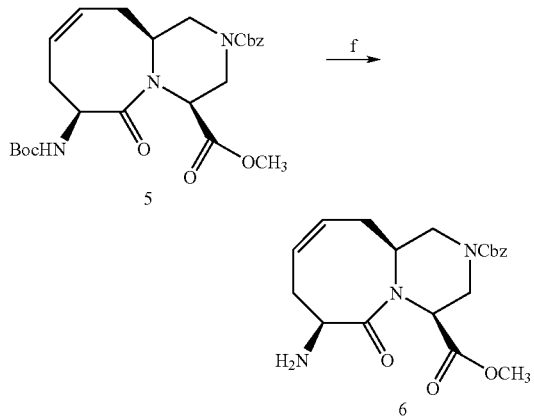

Reagents and conditions: f) TFA, CH$_2$Cl$_2$.

The starting material for this synthesis, 3-(allylbenzyloxycarbonylamino)-2-(S)-tert-butoxycarbonylamino propionic acid methyl ester, can be prepared from N-Boc-L-serine via the procedure described by A. M. Warshawsky et al., *Org. Chem.*, 62, p. 6439 (1997).

Preparation of 6-methoxy-piperazine-1,2,4-tricarboxylic acid 4-benzyl ester 1-tert-butyl ester 2-methyl ester (1): A solution containing 3-(allylbenzyloxycarbonylamino)-2-(S)-tert-butoxycarbonylamino propionic acid methyl ester (5.2 g, 12.8 mmol) in 550 mL of 10:1 CH$_2$Cl$_2$/MeOH is cooled to −78° C. Ozone gas is passed through the solution until a blue color persists. The solution is purged with N$_2$ to remove excess ozone and is then treated with excess dimethylsulfide. The solution is allowed to warm to rt overnight and the next morning concentrated in vacuo. The crude residue obtained is re-dissolved in MeOH and treated with Dowex50x-200. After stirring for 4 h, the solution was filtered, concentrated and immediately purified by flash chromatography on silica gel (EtOAc/hexane) to afford 2.75 g (53% yield) of the desired product. $^1$H NMR (CDCl$_3$) δ 7.40 (m, 5H), 5.60–3.40 (series of m, 6H), 5.19 (br s, 2H), 3.74 (s, 3H), 3.40 (series of s, 3H), 1.50 (series of s, 9H); MS 409 (M+H)$^+$.

Preparation of 6-allylpiperazine-1,2,4-tricarboxylic acid 4-benzyl ester 1-tert-butyl ester 2-methyl ester (2): 6-Methoxy-piperazine-1,2,4-tricarboxylic acid 4-benzyl ester 1-tert-butyl ester 2-methyl ester, 1, (2.71 g, 6.6 mmol) is dissolved in 50 mL of CH$_2$Cl$_2$ and cooled to −78° C. Allyltrimethylsilane (2.64 mL, 16.6 mmol) and BF$_3$OEt$_2$ (1.26 mL, 9.9 mmol) are added sequentially and the solution is stirred for 15 min before concentrating in vacuo. The crude residue obtained is used without further purification.

Preparation of 5-allyl-piperazine-1,3-dicarboxylic acid 1-benzyl ester 3-methyl ester (3): Crude 6-allylpiperazine-1,2,4-tricarboxylic acid 4-benzyl ester 1-tert-butyl ester 2-methyl ester, 2, obtained in the procedure above, is re-dissolved in 25% TFA in CH$_2$Cl$_2$ and stirred for 30 min at room temperature. After concentrating in vacuo, the residue is treated with saturated NaHCO$_3$ and the aqueous layer extracted with EtOAc. The organic layer is dried (MgSO$_4$) and concentrated to afford 1.8 g of crude material. Purification over silica gel (EtOAc/hexane) affords 840 mg of 3 as a clear oil. $^1$H NMR (CDCl$_3$) δ 7.39 (br s, 5H), 5.78 (m, 1H), 5.18 (m, 4H), 4.45 (m, 1H), 4.11 (m, 1H), 3.76 (s, 3H), 3.48 (dd, J=10.5, 3.0 Hz, 1H), 2.84 (m, 1H), 2.72 (m, 1H), 2.51 (m, 1H), 2.36–2.07 (m, 3H); $^{13}$C NMR (CDCl$_3$) δ 171.0, 155.3, 136.8, 133.9, 128.8 (2C), 128.4, 128.3(2C), 119.0, 67.6, 57.6, 54.0, 52.5, 49.2, 46.0, 38.2; MS 319 (M+H)$^+$.

Preparation of 5-allyl-4-(2-tert-butoxycarbonylaminopent-4-enoyl)-piperazine-1,3-dicarboxylic acid 1-benzyl ester 3-methyl ester (4): A solution containing 5-allyl-piperazine-1,3-dicarboxylic acid 1-benzyl ester 3-methyl ester, 3, (1.64 g, 5.1 mmol), N-Boc-allylglycine (3.9 g, 18.0 mmol) and 2-isobutoxy-1-isobutoxycarbonyl-1,2-dihydroquinoline (IIDQ) (5.5 g, 18.0 mmol) in THF was stirred at rt for 48 h. The solvent is removed in vacuo and the residue is purified over silica gel (EtOAc/hexane) to afford 1.28 g (48%) of 4. $^1$H NMR (CDCl$_3$) δ 7.39 (m, 5H), 5.78 (m, 2H), 5.38–5.10 (m, 6H), 5.0–4.1 (series of m, 5H), 3.73 (br s, 3H), 2.66–2.20 (series of m, 7H), 1.45 (br s, 9H); MS 516 (M+H)$^+$.

Preparation of (4S,6S,10aS)-6-tert-butoxycarbonylamino-1,3,4,5,6,7,10.10a-octahydro-2,4a-diaza-benzocyclooctene-2,4-dicarboxylic acid 2-benzyl ester 4-methyl ester (5): Grubbs catalyst (0.30 g) is added to a solution of 5-allyl-4-(2-tert-butoxycarbonyl-aminopent-4-enoyl)-piperazine-1,3-dicarboxylic acid 1-benzyl ester 3-methyl ester, 4, (1.28 g, 2.5 mmol) in 50 mL of CH$_2$Cl$_2$. The solution is refluxed for 12 hours after which additional catalyst (0.29 g) is added and the solution is refluxed for another 3 hours. The solution is then cooled, 1 mL of DMSO is added, and stirring continued at room temperature for an additional 12 hours. The solvent is removed in vacuo and the residue purified over silica gel (EtOAc/hexane) to afford 0.63 g (52%) of the desired product. $^1$H NMR (CDCl$_3$) δ 7.37 (m, 5H), 5.86 (br d, J=6.3 Hz, 1H), 5.63 (m, 2H), 5.17 (br s, 2H), 5.06 (d, J=4.2 Hz, 1H), 4.92 (m, 1H), 4.64 (d, J=13.8, 1H), 4.40 (m, 1H), 3.98 (m, 1H), 3.65 (m, 1H), 3.25 (m, 2H), 2.92 (m, 1H), 2.60–2.30 (m, 3H), 1.45 (s, 9H); MS 488 (M+H)$^+$.

Preparation of (4S,6S,10aS)-6-amino-5-oxo-1,3,4,5,6,7,10,10a-octahydro-2,4a-diaza-benzocyclooctene-2,4-dicarbocylic acid 2-benzyl ester 4-methyl ester (6): A solution containing 6-tert-butoxycarbonylamino-1,3,4,5,6,7,10,10a-octahydro-2,4a-diaza-benzocyclooctene-2,4-dicarboxylic acid 2-benzyl ester 4-methyl ester, 5, (0.98 g, 2.0 mmol) in 10 mL of CH$_2$Cl$_2$ is treated with 2.5 mL of TFA and stirred at room temperature for 30 minutes. The solution is concentrated in vacuo and treated with saturated NaHCO$_3$. Solid NaCl is added to the resulting aqueous solution and the solution is extracted with EtOAc. The organic layer was dried (MgSO$_4$) and concentrated in vacuo to afford the desired intermediate which can be used without further purification.

Intermediate 6, prepared by the procedure herein above, represents the core of the Category I scaffold. The formulator can now attach the desired R unit to the scaffold, for example, a benzoyl unit as illustrated in Scheme II herein below.

Scheme II

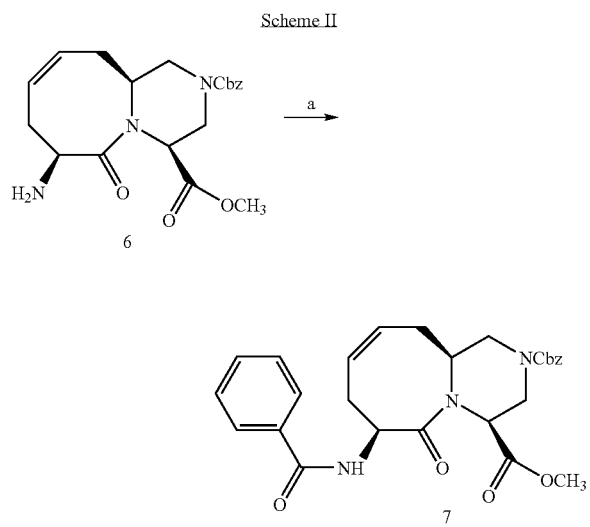

Reagents and conditions: a) benzoyl chloride, Et₃N, THF.

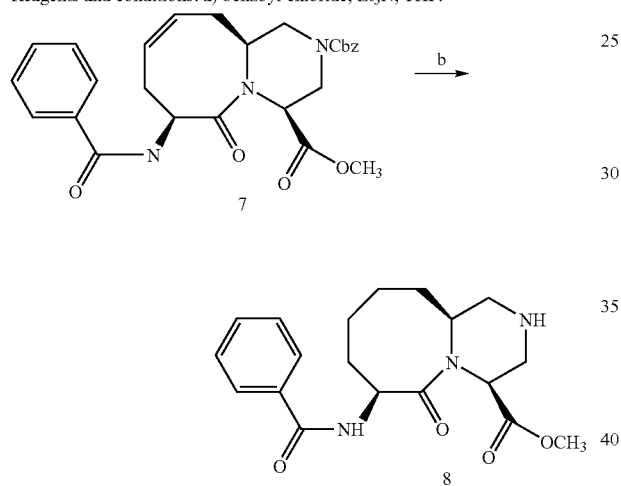

Reagents and conditions: b) H₂, Pd/C, MeOH.

Preparation of (4S,6S,10aS)-6-benzoylamino-5-oxo-1,3,4,5,6,7,10,10a-octahydro-2,4a-diaza-benzocyclooctene-2,4-dicarbocylic acid 2-benzyl ester 4-methyl ester (7): Crude (4S,6S,10aS)-6-amino-5-oxo-1,3,4,5,6,7,10,10a-octahydro-2,4a-diaza-benzocyclooctene-2,4-dicarbocylic acid 2-benzyl ester 4-methyl ester, 6, is dissolved in 10 mL of THF and treated with Et₃N (1.1 mL, 7.9 mmol) and benzoyl chloride (0.6 mL, 5.1 mmol). The solution is stirred for 1.5 hours at room temperature before being diluted with EtOAc, then washed with 1 N HCl and brine, and dried (MgSO₄). The solution is concentrated in vacuo and purified over silica gel (EtOAc/hexane) to afford 0.88 g of the desired product. $^1$H NMR (CDCl₃) δ 7.85 (m, 3H), 7.55–7.34 (m, 7H), 5.69 (m, 2H), 5.34 (m, 1H), 5.22 (d, J=12.6 Hz, 1H), 5.16 (d, J=12.6 Hz, 1H), 5.03 (d, J=3.9 Hz, 1H), 4.68 (d, J=13.8 Hz, 1H), 4.55 (m, 1H), 4.11 (m, 1H), 3.73 (m, 3H), 3.16 (m, 3H), 2.54 (m, 3H); MS 492 (M+H)⁺.

Preparation of (4S,6S,10aS)-6-benzoylamino-5-oxo-decahydro-2,4-diazabenzocyclo-octene-4-carbocylic acid methyl ester (8): (4S,6S,10aS)-6-benzoylamino-5-oxo-1,3,4,5,6,7,10,10a-octahydro-2,4a-diaza-benzocyclooctene-2,4-dicarbocylic acid 2-benzyl ester 4-methyl ester, 7, (135 mg, 0.27 mmol) is dissolved in 5 mL of MeOH and treated with wet 10% Pd/C (50 mg) under a H₂ atmosphere for 1 hour. The catalyst is removed by filtration and the solution concentrated in vacuo to afford the desired product. $^1$H NMR (CDCl₃) δ 7.81 (d, J=6.9 Hz, 2H), 7.6–7.4 (m, 3H), 5.21 (m, 2H), 4.50 (d, J=12.9 Hz, 1H), 4.31 (d, J=10.5 Hz, 1H), 3.79 (s, 3H), 3.32 (dd, J=14.1, 4.8 Hz, 1H), 2.99 (dd, J=13.5, 4.2 Hz, 1H), 2.23 (s, 3H), 2.35–1.40 (m, 10H); $^{13}$C NMR (CDCl₃) δ 173.4, 170.4, 170.1, 166.2, 134.3, 131.9, 128.8 (2C), 127.2(2C), 52.8, 51.7, 51.1, 50.9, 46.2, 45.0, 38.1, 33.5, 24.2, 23.8, 21.1; MS 402 (M+H)⁺.

Once the desired R unit has been attached to the now completed Category I [8,6] fused-ring scaffold, for example, intermediate 8, the formulator can further modify the core structure by attaching the selected R⁹ unit, as well as attaching the desired cysteine trap. Scheme III outlines the preparation of analogs which comprise a first iteration of Category I wherein R⁹ comprises an L² unit equal to C=O and R¹⁰ which is linear alkyl,. In the disclosed example R⁹ is an acetyl unit.

Scheme III

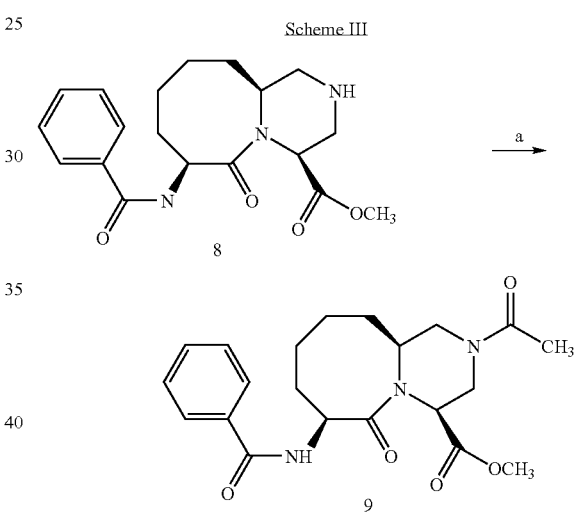

Reagents and conditions: a) CH₃COCl, Et₃N, THF.

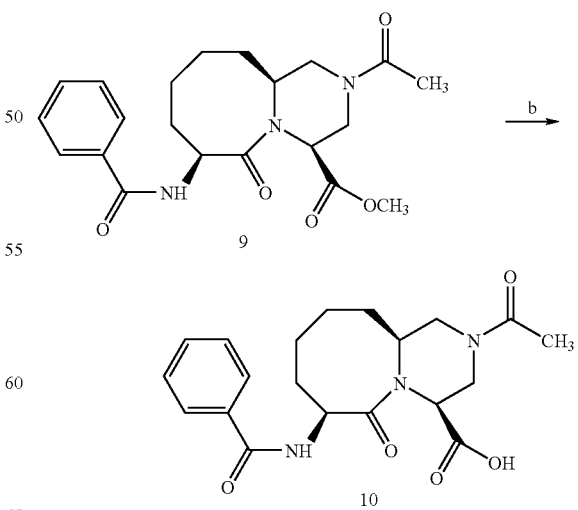

Reagents and conditions: b) LiOH, THF/H₂O, rt, 8 hrs.

-continued

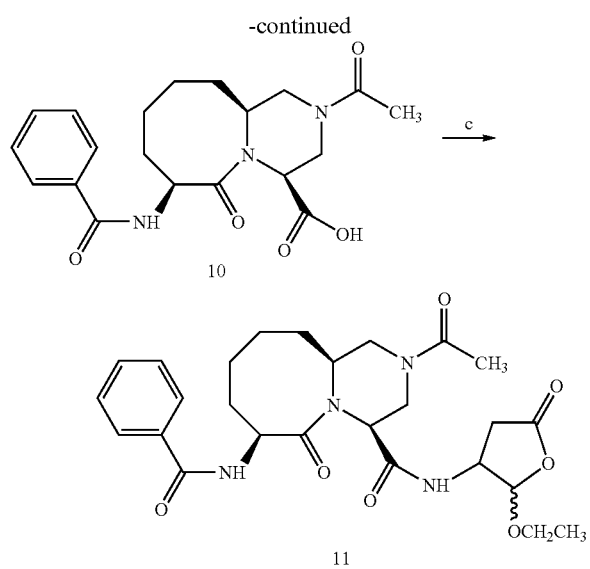

Reagents and conditions: c) (2-ethoxy-5-oxo-tetrahydrofurany-3-yl)-
carbamic acid allyl ester; N,N-
dimethylbarbituric acid, (Ph₃P)₄Pd,
CH₂Cl₂, EDCl, HOBt.

EXAMPLE 1

(4S,6S,10aS)-2-Acetyl-6-benzoylamino-5-oxo-decahydro-2,4a-diaza-benzocyclooctene-4-carboxylic acid (2-ethoxy-5-oxo-tetrahydrofuran-3-yl)amide (11)

Preparation of (4S,6S,10aS)-2-acetyl-6-benzoylamino-5-oxo-decahydro-2,4a-diaza-benzocyclooctene-4-carbocylic acid methyl ester (9): Crude (4S,6S,10aS)-6-benzoylamino-5-oxo-decahydro-2,4a-diazabenzocyclo-octene-4-carbocylic acid methyl ester, 8, prepared by the above procedure is dissolved in 5 mL of THF and treated with Et₃N (0.3 mL, 2.1 mmol) and acetyl chloride (0.08 mL, 1.1 mmol). After 30 min, the solution is diluted with EtOAc, washed with 1 N HCl and brine, and dried (MgSO₄). The solvent is removed in vacuo and the residue purified over silica gel (EtOAc/hexane) to afford 70 mg of the desired product.

Preparation of (4S,6S,10aS)-2-acetyl-6-benzoylamino-5-oxo-decahydro-2,4a-diaza-benzocyclooctene-4-carbocylic acid (10): A solution of (4S,6S,10aS)-2-acetyl-6-benzoylamino-5-oxo-decahydro-2,4a-diaza-benzocyclooctene-4-carbocylic acid methyl ester, 9, (70 mg, 0.17 mmol) in 4 mL of 3:1 THF/H₂O is treated with excess LiOH and stirred for 2.5 hours at room temperature. The solution is then acidified and extracted with EtOAc. The EtOAc layer is dried (MgSO₄) and concentrated in vacuo to yield 69 mg of the desired product.

Preparation of (4S,6S,10aS)-2-acetyl-6-benzoylamino-5-oxo-decahydro-2,4a-diaza-benzocyclooctene-4-carboxylic acid (2-ethoxy-5-oxo-tetrahydrofuran-3-yl)amide (11): A catalytic amount of Pd(Ph₃P)₄ is added to a solution of (2-Ethoxy-5-oxo-tetrahydrofuran-3-yl)-carbamic acid allyl ester (80 mg, 0.35 mmol) and N,N-dimethylbarbituric acid (109 mg, 0.70 mmol) in 2 mL CH₂Cl₂ at room temperature. The solution is stirred at rt for 15 minutes and (4S,6S,10aS)-2-acetyl-6-benzoylamino-5-oxo-decahydro-2,4a-diaza-benzo-cyclooctene-4-carbocylic acid, 10, (69 mg, 0.18 mmol) is added as a solution in 1 mL CH₂Cl₂, followed by 1-hydroxybenzotriazole (94 mg, 0.70 mmol) and 1-(3-dimethyl-aminopropyl)-3-ethyl-carbodiimide hydrochloride (132 mg, 0.70 mmol). The solution is stirred for 5 hours then diluted with EtOAc, washed with saturated NaHCO₃, brine, dried (MgSO₄), and concentrated in vacuo. Purification over silica gel afforded 70 mg of the desired product.

The compounds which comprise this iteration of Category I can also comprise other cysteine traps, for example, the 2-hydroxy-5-oxo-tetrahydrofuran-3-yl cysteine trap which can be prepared by the procedure outlined in Scheme IV beginning with the 2-ethoxy-5-oxo-tetrahydrofuran-3-yl cysteine trap. The example below converts compound 11 (analog 4 from Table I) to compound 12 (analog 44 from Table I).

Scheme IV

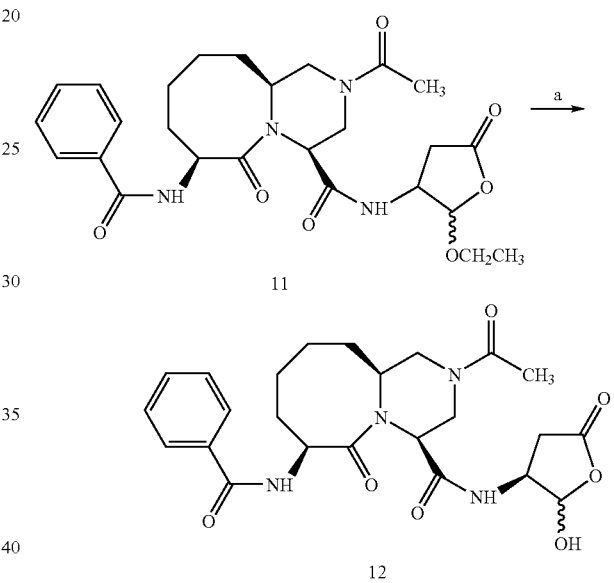

Reagents and conditions: a) TFA, acetonitrile/water.

EXAMPLE 2

(4S,6S10aS)-2-Acetyl-6-benzoylamino-5-oxo-decahydro-2,4a-diaza-benzocyclooctene-4-carboxylic acid (2-hydroxy-5-oxo-tetrahydrofuran-3-yl) amide (12)

Preparation of (4S,6S,10aS)-2-acetyl-6-benzoylamino-5-oxo-decahydro-2,4a-diaza-benzocyclooctene-4-carboxylic acid (2-hydroxy-5-oxo-tetrahydrofuran-3-yl)amide (12): A solution of (4S,6S,10aS)-2-acetyl-6-benzoylamino-5-oxo-decahydro-2,4a-diaza-benzocyclooctene-4-carboxylic acid (2-ethoxy-5-oxo-tetrahydrofuran-3-yl)amide, 11, (70 mg, 0.14 mmol) in acetonitrile/water is treated with trifluoroacetic acid. After stirring for 30 minutes the solution is concentrated in vacuo and the crude product purified by preparative reverse phase HPLC to afford 36 mg of the desired product as a white solid. ¹H NMR (CD₃OD) δ 7.90 (d, J=6.9 Hz, 2H), 7.52 (m, 3H), 5.2–4.2 (series of m, 7H), 3.40 (m, 1H), 3.18 (m, 1H), 2.8–1.2 (series of m, 12H), 2.35 (s, 3H); MS 487 (M+H)⁺.

Other non-limiting examples of this first iteration of Category I include:

(4S,6S,10aS)-2-Benzoyl-6-benzoylamino-5-oxo-decahydro-2,4a-diazabenzocydooctene-4-carboxylic acid (2-hydroxy-5-oxo-tetrahydro-furan-3-yl)-amide: $^1$H NMR (CD$_3$OD) δ 7.92–7.90 (d, J=6.9 Hz, 2H), 7.58–7.47 (m, 9H), 5.12–4.19 (series of m, 8H), 3.73–3.16 (series of m, 2H), 2.48–1.18 (series of m, 11H); MS 549 (M+H)$^+$.

(4S,6S,10aS)-6-Benzoylamino-2-methyl-5-oxo-decahydro-2,4a-diazabenzocydooctene-4-carboxylic acid (2-hydroxy-5-oxo-tetrahydro-furan-3-yl)-amide: $^1$H NMR (CD$_3$OD) δ 7.93–7.90 (d, J=7.5 Hz, 2H), 7.59–7.49 (m, 3H), 5.34 (s, 1H), 5.09–5.05 (d, J=11Hz, 1H), 4.71–4.34 (m, 3H), 3.87–3.83 (d, J=12.3 Hz, 1H), 3.42–3.57 (m, 3H), 3.12–3.07 (m, 1H), 2.96 (s, 3H), 2.68–1.13 (m, 11H); MS 458.9 (M+H)$^+$.

(4S,6S,10aS)-6-Benzoylamino-5-oxo-decahydro-2,4a-diaza-benzocyclooctene-2,4-dicarboxylic acid 4-[(2-hydroxy-5-oxo-tetrahydro-furan-3-yl)-amide]2-phenylamide: $^1$H NMR (CD$_3$OD) δ 7.93–7.90 (d, J=7.2 Hz, 2H), 7.60–7.47 (m, 3H), 7.40–7.27 (m, 6H), 7.06–7.01 (t, J=7.2 Hz, 1H), 5.16–5.08 (m, 2H), 4.73–4.72 (d, J=3.6 Hz, 1H), 4.52–4.36 (m, 3H), 4.22–4.17 (d, J=13.2 Hz, 1H), 3.42–3.31 (m, 3H), 2.73–2.49 (m, 2H), 2.18–1.18 (m, 8H); MS 563.8 (M+H)$^+$.

(4S,6S,10aS)-6-Benzoylamino-5-oxo-decahydro-2,4a-diaza-benzocyclooctene-4-carboxylic acid (2-hydroxy-5-oxo-tetrahydro-furan-3-yl) amide: $^1$H NMR (CD$_3$OD) δ 7.91–7.87 (m, 2H), 7.61–7.48 (m, 3H), 5.19–4.29 (series of m, 6H), 3.73–2.91 (series of m, 5H), 2.73–1.15 (series of m, 12H); MS 477 (M+H)$^+$.

(4S,6S,10aS)-6-[(Naphalene-2-carbonyl)-amino]-5-oxo-decahydro-2,4a-diazabenzocyclo-octene-4-carboxylic acid (2-hydroxy-5-oxo-tetrahydro-furan-3-yl)amide: $^1$H NMR (1:1 CD$_3$OD/D$_2$O) δ 8.47 (s, 1H), 8.01 (m, 4H), 7.65 (m, 2H), 5.25 (m, 1H), 5.12 (d, J=12.1 Hz, 1H), 4.70 (m, 2H), 4.23 (m, 1H), 3.81 (d, J=13.5 Hz, 1H), 3.60 (m, 1H), 3.23 (m, 1H), 2.60–1.20 (series of m, 11H); MS 495 (M+H)$^+$.

(4S,6S,10aS)-2-Acetyl-6-[(isoquinoline-1-carbonyl)-amino]-5-oxo-decahydro-2,4a-diazabenzocyclo-octene-4-carboxylic acid (2-hydroxy-5-oxo-tetrahydro-furan-3-yl) amide: $^1$H NMR (CD$_3$OD) δ 9.17 (d, J=8.0 Hz, 1H), 8.57 (d, J=5.5 Hz, 1H), 8.02 (m, 2H), 7.84 (dd, J=7.3, 6.9 Hz, 1H), 7.75 (dd, J=7.7, 7.7 Hz, 1H), 5.24 (d, J=8.8 Hz, 1H), 5.09 (m, 1H), 4.80–4.20 (m, 5H), 3.43 (m, 1H), 3.19 (m, 1H), 2.60 (m, 2H), 2.37 (s, 3H), 2.40–1.40 (series of m, 8H); MS 538 (M+H)$^+$.

(4S,6S,10aS)-2-Methanesulfonyl-6-[(naphalene-2-carbonyl)-amino]-5-oxo-decahydro-2,4a-diazabenzocyclo-octene-4-carboxylic acid (2-hydroxy-5-oxo-tetrahydro-furan-3-yl)amide: $^1$H NMR (CD$_3$OD) δ 8.48 (s, 1H), 8.02 (m, 1H), 7.98 (m, 3H), 7.60 (m, 2H), 5.18 (m, 2H), 4.71 (m, 1H), 4.55 (d, J=12.8 Hz, 1H), 4.33 (m, 1H), 4.23 (d, J=13.2 Hz, 1H), 3.69 (d, J=12.4 Hz, 1H), 3.33 (m, 1H), 3.08 (m, 1H), 3.02 (s, 3H), 2.61 (m, 2H), 2.20 (m, 2H), 1.90 (m, 4H), 1.60 (m, 2H); MS 573 (M+H)$^+$.

(4S,6S,10aS)-2-Benzenesulfonyl-6-[(naphalene-2-carbonyl)-amino]-5-oxo-decahydro-2,4a-diazabenzocyclo-octene-4-carboxylic acid (2-hydroxy-5-oxo-tetrahydro-furan-3-yl)amide: $^1$H NMR (CD$_3$OD) δ 8.43 (s, 1H), 7.95 (m, 6H), 7.68 (m, 5H), 5.10 (m, 2H), 4.73 (m, 1H), 4.48 (d, J=12.8 Hz, 1H), 4.30 (m, 2H), 3.63 (d, J=13.4 Hz, 1H), 2.90–2.50 (m, 4H), 2.35 (m, 1H), 2.10–1.75 (m, 4H), 1.65–1.30 (m, 4H); MS 635 (M+H)$^+$.

(4S,6S,10aS)-6-[(Isoquinoline-1-carbonyl)-amino]-5-oxo-decahydro-2,4a-diazabenzocyclo-octene-4-carboxylic acid (2-hydroxy-5-oxo-tetrahydro-furan-3-yl)amide: $^1$H NMR (CD$_3$OD) δ 8.75 (dd, J=7.0, 6.4 Hz, 1H), 8.55 (d, J=5.9 Hz, 1H), 8.06 (d, J=8.0 Hz, 1H), 8.04 (d, J=5.9 Hz, 1H), 7.88 (ddd, J=8.0, 7.0, 1.1 Hz, 1H), 7.78 (dd, J=8.0, 7.0 Hz, 1H), 5.25 (m, 1H), 5.18 (d, J=12.1 Hz, 1H), 4.85 (m, 3H), 4.20 (m, 1H), 3.82 (d, J=13.5 Hz, 1H), 3.58 (m, 1), 3.20 (m, 2H), 2.60–1.40 (series of m, 10H); MS 496 (M+H)$^+$.

(4S,6S,10aS)-2-Methanesulfonyl-6-[(Isoquinoline-1-carbonyl)-amino]-5-oxo-decahydro-2,4a-diazabenzocyclo-octene-4-carboxylic acid (2-hydroxy-5-oxo-tetrahydro-furan-3-yl)amide: $^1$H NMR (CD$_3$OD) δ 9.16 (d, J=8.5 Hz, 1H), 8.56 (d, J=5.5 Hz, 1H), 8.02 (d, J=9.1 Hz, 1H), 7.99 (d, J=5.5 Hz, 1H), 7.83 (ddd, J=8.1, 7.0, 1.1 Hz, 1H), 7.74 (ddd, J=8.5, 7.0, 1.1 Hz, 1H), 5.22 (m, 2H), 4.72 (m, 1H), 4.56 (d, J=12.8 Hz, 1H), 4.33 (m, 1H), 4.25 (d, J=12.8 Hz, 1H), 3.70 (d, J=12.5 Hz, 1H), 3.31 (m, 1H), 3.04 (m, 4H), 2.61 (m, 2H), 2.30 (m, 2H), 2.02 (m, 1H), 1.85 (m, 2H), 1.63 (m, 1 H), 1.52 (m, 1H), 1.30 (m, 1H); MS 574 (M+H)$^+$.

(4S,6S,10aS)-2-Benzenesulfonyl-6-[(Isoquinoline-1-carbonyl)-amino]-5-oxo-decahydro-2,4a-diaza-benzocyclo-octene-4-carboxylic acid (2-hydroxy-5-oxo-tetrahydro-furan-3-yl)amide: $^1$H NMR (CD$_3$OD) δ 9.09 (d, J=8.8 Hz, 1H), 8.53 (d, J=5.5 Hz, 1H), 7.99 (d, J=8.5 Hz, 1H), 7.96 (d, J=5.8 Hz, 1H), 7.89–7.62 (m, 7H), 5.11 (m, 2H), 4.73 (m, 1H), 4.49 (d, J=12.4 Hz, 1H), 4.30 (m, 2H), 3.63 (d, J=11.7 Hz, 1H), 2.81 (m, 1H), 2.60 (m, 3H), 2.30 (m, 2H), 2.02 (m, 1H), 1.82 (m, 2H), 1.70–1.40 (m, 4H); MS 636 (M+H)$^+$.

(4S,6S,10aS)-2-Benzenesulfonyl-6-benzylamino-5-oxo-decahydro-2,4a-diaza-benzocydooctene-4-carboxylic acid (2-hydroxy-5-oxo-tetrahydro-furan-3-yl)-amide: $^1$H NMR (CD$_3$OD) δ 7.86–7.84 (d, J=7.5 Hz, 4H), 7.75–7.63 (m, 4H), 7.57-7.43 (m, 3H), 5.05–4.95 (m, 4H), 4.72–4.70 (dd, J=4.2, 1.5 Hz, 1H), 4.48–4.44 (d, J=12 Hz, 1H), 4.38–4.32 (m, 1H), 4.27–4.23 (d, J=12.3 Hz, 1H), 3.64–3.60 (d, J=12 Hz, 1H), 3.41–3.34 (m, 1H), 2.79–1.27 (series of m, 11H); MS 584.9 (M+H)$^+$.

(4S,6S,10aS)-6-[(isoquinoline-1-carbonyl)-2amino]-2-methyl-5-oxo-decahydro-2,4a-diaza-benzocyclooctene-4-carboxylic acid (2-hydroxy-5-tetrahydro-furan-3-yl)-amide: $^1$H NMR (CD$_3$CN): δ 9.46 (d, J=8.7 Hz, 1H), 9.01 (d, J=7.0 Hz, 1H), 8.85 (d, J=5.4 Hz, 1H), 8.00 (m, 2H), 7.81 (m, 3H), 7.61 (m, 1H), 5.43 (m, 1H), 5.18 (m, 1H), 4.74 (m, 1H), 3.48 (m, 3H), 3.17 (m, 1H), 2.27 (m, 2H), 2.18 (s, 3H), 2.13–1.95 (m, 2H), 1.77 (m, 1H), 1.65 (m, 2H), 1.46 (m, 2H), 1.21 (m, 2H), 0.98 (m,1H). ESI MS 510.14 (M+H).

(4S,6S,10aS)-2-Benzenesulfonyl-6-[(isoquinoline-1-carbonyl)-amino]-5-oxo-decahydro-2,4a-diaza-benzocyclooctene-4-carboxylic acid (2-ethoxy-5-oxo-tetrahydro-furan-3-yl)-amide: (Mixture of diastereomers) $^1$H NMR (CDCl$_3$) δ 9.42 (d, J=8.4 Hz, 1H), 9.05 (m, 1H), 8.54 (s, 1 H), 7.89–7.49 (series of m, 9H), 5.51 (m, 1H), 5.15–5.01 (m, 2H), 4.71 (m, 1H), 4.37 (m, 2H), 4.14 (m, 1H), 4.01–3.85 (m, 1H), 3.77–3.65 (m, 2H), 3.06–2.78 (m, 2H), 2.51–2.24 (m, 4H), 2.07–1.89 (m, 3H), 1.49–1.23 (m, 6H); HRMS 664.2425 (M+H)+.

A further iteration within this first aspect of Category I are compound wherein R$^9$ units have the formula —SO$_2$R$^{10}$ (SO$_2$ units replace C═O units of the first iteration as linking units L$^2$). The compounds can be suitably prepared by the procedure outlined in Scheme V beginning with intermediate 8.

Scheme V

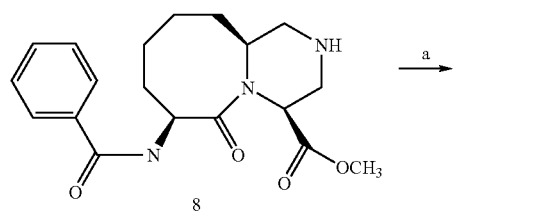

Reagents and conditions: a) CH₃SO₂Cl, Et₃N, THF, 0° C. to rt.

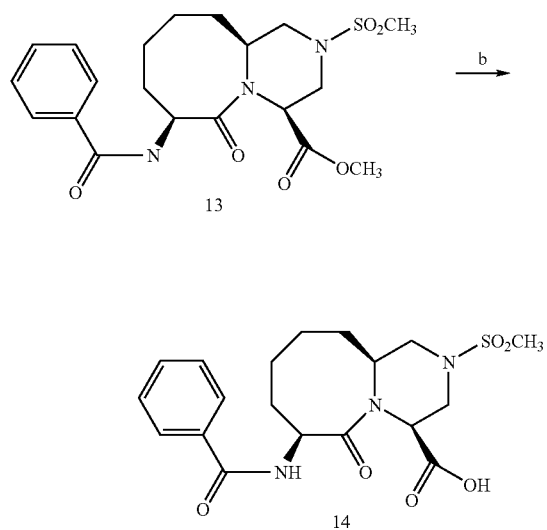

Reagents and conditions: b) LiOH, THF/H₂O, rt, 8 hrs.

Scheme V

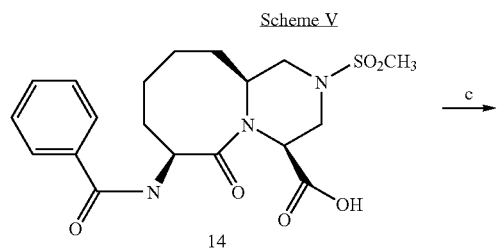

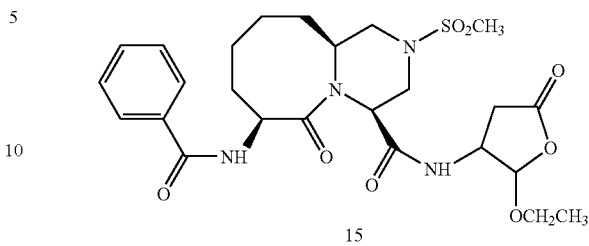

Reagents and conditions: c) (2-ethoxy-5-oxo-tetrahydrofurany-3-yl)-carbamic acid; N,N-dimethylbarbituric acid, (Ph₃P)₄Pd, CH₂Cl₂, EDCl, HOBt.

EXAMPLE 3

(4S,6S,10aS)-6-Benzoylamino-2-methanesulfonyl-5-oxo-decahydro-2,4a-diazabenzo-cyclooctene-4-carboxylic acid (2-hydroxy-5-oxo-tetrahydrofuran-3-yl) amide (15)

Preparation of (4S,6S,10aS)-6-benzoylamino-2-methanesulfonyl-5-oxo-decahydro-2,4a-diazabenxocylooctene-4-carboxylic acid methyl ester (13): To a cooled (0° C.) solution of (4S,6S,10aS)-6-benzoylamino-5-oxo-decahydro-2,4a-diaza-benzocyclo-octene-4-carbocylic acid methyl ester, 8, (359 mg, 1.0 mmol) in anhydrous tetrahydrofuran (10 mL) was added triethylamine (0.84 mL, 6 mmol), and then methanesulfonyl chloride (0.097 mL, 1.2 mmol). The resulting suspension was stirred at room temperature for twenty-four hours and the solvents were removed under reduced pressure. The crude product was purified by reverse phase HPLC to afford the desired product.

Preparation of (4S,6S,10aS)-6-benzoylamino-2-methanesulfonyl-5-oxo-decahydro-2,4a-diaza-benzocyclooctene-4-carboxylic acid (14): A solution of (4S,6S,10aS)-6-benzoyl-2-methane-sulfonylamino-5-oxo-decahydro-2,4a-diaza-benzocyclooctene-4-carboxylic acid methyl ester, 13, (100 mg, 0.234 mmol) in 4 mL of 3:1 THF/H₂O is treated with excess LiOH and stirred for 2.5 hours at room temperature. The solution is then acidified and extracted with EtOAc. The EtOAc layer is dried (MgSO₄) and concentrated in vacuo to yield 69 mg of the desired product.

Preparation of (4S,6S,10aS)-6-benzoylamino-2-methanesulfonyl-5-oxo-decahydro-2,4a-diaza-benzocyclooctene-4-carboxylic acid (2-ethoxy-5-oxo-tetrahydrofuran-3-yl) amide (15): A catalytic amount of Pd(Ph₃P)₄ is added to a solution of (2-Ethoxy-5-oxo-tetrahydrofuran-3-yl)-carbamic acid allyl ester (80 mg, 0.35 mmol) and N,N-dimethylbarbituric acid (109 mg, 0.70 mmol) in 2 mL CH₂Cl₂ at room temperature. The solution is stirred at rt for 15 minutes and (4S,6S,10aS)-6-benzoylamino2-methanesulfonyl-5-oxo-decahydro-2,4a-diazabenzo-cyclooctene-4-carbocylic acid, 10, is added as a solution in 1 mL CH₂Cl₂, followed by 1-hydroxybenzotriazole (94 mg, 0.70 mmol) and 1-(3-dimethyl-aminopropyl)-3-ethyl-carbodiimide hydrochloride (132 mg, 0.70 mmol). The solution is stirred for 5 hours then diluted with EtOAc, washed with saturated NaHCO₃, brine, dried (MgSO₄), and concentrated in vacuo. Purification over silica gel afforded 70 mg of the desired product.

The compounds of this aspect of Category I can also comprise the cysteine trap 2-hydroxy-5-oxo-tetrahydrofuran-3-yl and can be prepared by the procedure outlined in Scheme VI. The example below converts compound 15 (analog 5 from Table I) to compound 16 (analog 45 from Table I).

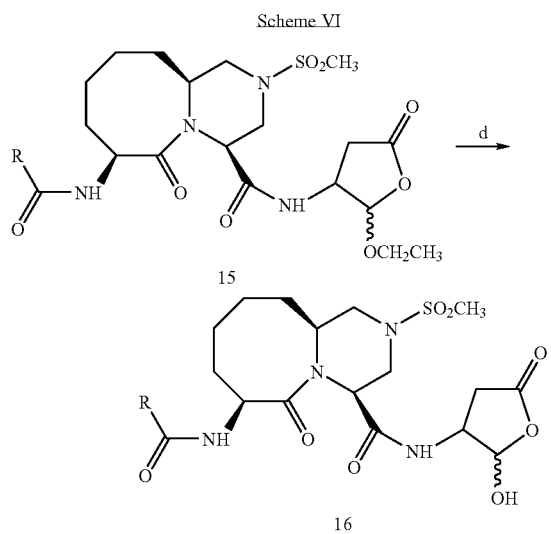

Reagents and conditions: d) TFA, acetonitrile/water.

EXAMPLE 4

(4S,6S,10aS)-2-Methansulfonyl-6-benzoylamino-5-oxo-decahydro-2,4a-diaza-benzocyclooctene-4-carboxylic acid (2-hydroxy-5-oxo-tetrahydrofuran-3-yl)amide (16)

Preparation of (4S,6S,10aS)-2-methansulfonyl-6-benzoylamino-5-oxo-decahydro-2,4a-diaza-benzocyclooctene-4-carboxylic acid (2-hydroxy-5-oxo-tetrahydrofuran-3-yl)amide (16): A solution of (4S,6S,10aS)-6-benzoylamino-2-methanesulfonyl-5-oxo-decahydro-2,4a-diaza-benzocyclooctene-4-carboxylic acid (2-ethoxy-5-oxo-tetrahydrofuran-3-yl)amide, 15, (70 mg, 0.13 mmol) in acetonitrile/water is treated with trifluoroacetic acid. After stirring for 30 minutes the solution is concentrated in vacuo and the crude product purified by preparative reverse phase HPLC to afford the desired product. $^1$H NMR (CD$_3$OD) δ 7.90–7.88 (d, J=6.9 Hz, 2H), 7.52–7.55 (t, J=7.2 Hz, 1H), 7.52–7.47 (d, J=6.9 Hz, 2H), 5.14–5.11 (m, 2H), 4.69–4.67 (m, 1H), 4.54–4.49 (broad, d, J=12.6 Hz, 1H), 4.34–4.30 (m, 1H), 4.24–4.19 (broad d, J=12.9 HZ, 1H), 3.69–3.65 (d, J=12 Hz,1H), 3.40–3.28 (m, 3H), 3.09–3.04 (m,1H), 3.01 (s, 3H), 2.71–1.28 (m, 11H); MS 522.8 (M+H)$^+$.

Category II of the interleukin-1β converting enzyme inhibitors of the present invention relates to compound comprising a 2,4,6-substituted 1,2,3,4,6,7,10,10a-octahydro-2,4-diaza-benzocycloocten-5-one scaffold having the formula:

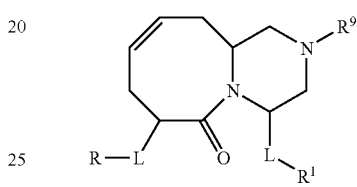

one iteration of which comprises scaffolds having the indicated stereochemistry. Table II relates to non-limiting examples of analogs comprising a first aspect of this category, said analogs having the formula:

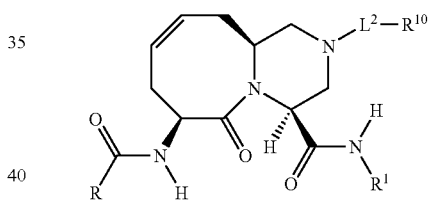

wherein R, R$^1$ and -L$^2$-R$^{10}$ are defined in Table II herein below.

TABLE II

| No. | R | R$^1$ | —L$^2$—R$^{10}$ |
|---|---|---|---|
| 121 | phenyl | 2-ethoxy-5-oxo-tetrahydrofuran-3-yl | —CH$_3$ |
| 122 | phenyl | 2-ethoxy-5-oxo-tetrahydrofuran-3-yl | —CH$_2$CH$_3$ |
| 123 | phenyl | 2-ethoxy-5-oxo-tetrahydrofuran-3-yl | —C(O)CH$_3$ |
| 124 | phenyl | 2-ethoxy-5-oxo-tetrahydrofuran-3-yl | —SO$_2$CH$_3$ |
| 125 | phenyl | 2-ethoxy-5-oxo-tetrahydrofuran-3-yl | —SO$_2$CH$_2$CH$_3$ |
| 126 | phenyl | 2-ethoxy-5-oxo-tetrahydrofuran-3-yl | —SO$_2$CH(CH$_3$)$_2$ |
| 127 | phenyl | 2-ethoxy-5-oxo-tetrahydrofuran-3-yl | —SO$_2$C$_6$H$_5$ |
| 128 | phenyl | 2-ethoxy-5-oxo-tetrahydrofuran-3-yl | —C(O)C$_6$H$_5$ |
| 129 | phenyl | 2-ethoxy-5-oxo-tetrahydrofuran-3-yl | —C(O)OCH$_2$C$_6$H$_5$ |
| 130 | phenyl | 2-ethoxy-5-oxo-tetrahydrofuran-3-yl | —C(O)NHC$_6$H$_5$ |
| 131 | naphth-1-yl | 2-ethoxy-5-oxo-tetrahydrofuran-3-yl | —CH$_3$ |
| 132 | naphth-1-yl | 2-ethoxy-5-oxo-tetrahydrofuran-3-yl | —CH$_2$CH$_3$ |
| 133 | naphth-1-yl | 2-ethoxy-5-oxo-tetrahydrofuran-3-yl | —C(O)CH$_3$ |
| 134 | naphth-1-yl | 2-ethoxy-5-oxo-tetrahydrofuran-3-yl | —SO$_2$CH$_3$ |
| 135 | naphth-1-yl | 2-ethoxy-5-oxo-tetrahydrofuran-3-yl | —SO$_2$CH$_2$CH$_3$ |
| 136 | naphth-1-yl | 2-ethoxy-5-oxo-tetrahydrofuran-3-yl | —SO$_2$CH(CH$_3$)$_2$ |
| 137 | naphth-1-yl | 2-ethoxy-5-oxo-tetrahydrofuran-3-yl | —SO$_2$C$_6$H$_5$ |
| 138 | naphth-1-yl | 2-ethoxy-5-oxo-tetrahydrofuran-3-yl | —C(O)C$_6$H$_5$ |
| 139 | naphth-1-yl | 2-ethoxy-5-oxo-tetrahydrofuran-3-yl | —C(O)OCH$_2$C$_6$H$_5$ |
| 140 | naphth-1-yl | 2-ethoxy-5-oxo-tetrahydrofuran-3-yl | —C(O)NHC$_6$H$_5$ |
| 141 | naphth-2-yl | 2-ethoxy-5-oxo-tetrahydrofuran-3-yl | —CH$_3$ |

TABLE II-continued

| No. | R | R¹ | —L²—R¹⁰ |
|---|---|---|---|
| 142 | naphth-2-yl | 2-ethoxy-5-oxo-tetrahydrofuran-3-yl | —CH$_2$CH$_3$ |
| 143 | naphth-2-yl | 2-ethoxy-5-oxo-tetrahydrofuran-3-yl | —C(O)CH$_3$ |
| 144 | naphth-2-yl | 2-ethoxy-5-oxo-tetrahydrofuran-3-yl | —SO$_2$CH$_3$ |
| 145 | naphth-2-yl | 2-ethoxy-5-oxo-tetrahydrofuran-3-yl | —SO$_2$CH$_2$CH$_3$ |
| 146 | naphth-2-yl | 2-ethoxy-5-oxo-tetrahydrofuran-3-yl | —SO$_2$CH(CH$_3$)$_2$ |
| 147 | naphth-2-yl | 2-ethoxy-5-oxo-tetrahydrofuran-3-yl | —SO$_2$C$_6$H$_5$ |
| 148 | naphth-2-yl | 2-ethoxy-5-oxo-tetrahydrofuran-3-yl | —C(O)C$_6$H$_5$ |
| 149 | naphth-2-yl | 2-ethoxy-5-oxo-tetrahydrofuran-3-yl | —C(O)OCH$_2$C$_6$H$_5$ |
| 150 | naphth-2-yl | 2-ethoxy-5-oxo-tetrahydrofuran-3-yl | —C(O)NHC$_6$H$_5$ |
| 151 | isoquinolin-1-yl | 2-ethoxy-5-oxo-tetrahydrofuran-3-yl | —CH$_3$ |
| 152 | isoquinolin-1-yl | 2-ethoxy-5-oxo-tetrahydrofuran-3-yl | —CH$_2$CH$_3$ |
| 153 | isoquinolin-1-yl | 2-ethoxy-5-oxo-tetrahydrofuran-3-yl | —C(O)CH$_3$ |
| 154 | isoquinolin-1-yl | 2-ethoxy-5-oxo-tetrahydrofuran-3-yl | —SO$_2$CH$_3$ |
| 155 | isoquinolin-1-yl | 2-ethoxy-5-oxo-tetrahydrofuran-3-yl | —SO$_2$CH$_2$CH$_3$ |
| 156 | isoquinolin-1-yl | 2-ethoxy-5-oxo-tetrahydrofuran-3-yl | —SO$_2$CH(CH$_3$)$_2$ |
| 157 | isoquinolin-1-yl | 2-ethoxy-5-oxo-tetrahydrofuran-3-yl | —SO$_2$C$_6$H$_5$ |
| 158 | isoquinolin-1-yl | 2-ethoxy-5-oxo-tetrahydrofuran-3-yl | —C(O)C$_6$H$_5$ |
| 159 | isoquinolin-1-yl | 2-ethoxy-5-oxo-tetrahydrofuran-3-yl | —C(O)OCH$_2$C$_6$H$_5$ |
| 160 | isoquinolin-1-yl | 2-ethoxy-5-oxo-tetrahydrofuran-3-yl | —C(O)NHC$_6$H$_5$ |
| 161 | phenyl | 2-hydroxy-5-oxo-tetrahydrofuran-3-yl | —CH$_3$ |
| 162 | phenyl | 2-hydroxy-5-oxo-tetrahydrofuran-3-yl | —CH$_2$CH$_3$ |
| 163 | phenyl | 2-hydroxy-5-oxo-tetrahydrofuran-3-yl | —C(O)CH$_3$ |
| 164 | phenyl | 2-hydroxy-5-oxo-tetrahydrofuran-3-yl | —SO$_2$CH$_3$ |
| 165 | phenyl | 2-hydroxy-5-oxo-tetrahydrofuran-3-yl | —SO$_2$CH$_2$CH$_3$ |
| 166 | phenyl | 2-hydroxy-5-oxo-tetrahydrofuran-3-yl | —SO$_2$CH(CH$_3$)$_2$ |
| 167 | phenyl | 2-hydroxy-5-oxo-tetrahydrofuran-3-yl | —SO$_2$C$_6$H$_5$ |
| 168 | phenyl | 2-hydroxy-5-oxo-tetrahydrofuran-3-yl | —C(O)C$_6$H$_5$ |
| 169 | phenyl | 2-hydroxy-5-oxo-tetrahydrofuran-3-yl | —C(O)OCH$_2$C$_6$H$_5$ |
| 170 | phenyl | 2-hydroxy-5-oxo-tetrahydrofuran-3-yl | —C(O)NHC$_6$H$_5$ |
| 171 | naphth-1-yl | 2-hydroxy-5-oxo-tetrahydrofuran-3-yl | —CH$_3$ |
| 172 | naphth-1-yl | 2-hydroxy-5-oxo-tetrahydrofuran-3-yl | —CH$_2$CH$_3$ |
| 173 | naphth-1-yl | 2-hydroxy-5-oxo-tetrahydrofuran-3-yl | —C(O)CH$_3$ |
| 174 | naphth-1-yl | 2-hydroxy-5-oxo-tetrahydrofuran-3-yl | —SO$_2$CH$_3$ |
| 175 | naphth-1-yl | 2-hydroxy-5-oxo-tetrahydrofuran-3-yl | —SO$_2$CH$_2$CH$_3$ |
| 176 | naphth-1-yl | 2-hydroxy-5-oxo-tetrahydrofuran-3-yl | —SO$_2$CH(CH$_3$)$_2$ |
| 177 | naphth-1-yl | 2-hydroxy-5-oxo-tetrahydrofuran-3-yl | —SO$_2$C$_6$H$_5$ |
| 178 | naphth-1-yl | 2-hydroxy-5-oxo-tetrahydrofuran-3-yl | —C(O)C$_6$H$_5$ |
| 179 | naphth-1-yl | 2-hydroxy-5-oxo-tetrahydrofuran-3-yl | —C(O)OCH$_2$C$_6$H$_5$ |
| 180 | naphth-1-yl | 2-hydroxy-5-oxo-tetrahydrofuran-3-yl | —C(O)NHC$_6$H$_5$ |
| 181 | naphth-2-yl | 2-hydroxy-5-oxo-tetrahydrofuran-3-yl | —CH$_3$ |
| 182 | naphth-2-yl | 2-hydroxy-5-oxo-tetrahydrofuran-3-yl | —CH$_2$CH$_3$ |
| 183 | naphth-2-yl | 2-hydroxy-5-oxo-tetrahydrofuran-3-yl | —C(O)CH$_3$ |
| 184 | naphth-2-yl | 2-hydroxy-5-oxo-tetrahydrofuran-3-yl | —SO$_2$CH$_3$ |
| 185 | naphth-2-yl | 2-hydroxy-5-oxo-tetrahydrofuran-3-yl | —SO$_2$CH$_2$CH$_3$ |
| 186 | naphth-2-yl | 2-hydroxy-5-oxo-tetrahydrofuran-3-yl | —SO$_2$CH(CH$_3$)$_2$ |
| 187 | naphth-2-yl | 2-hydroxy-5-oxo-tetrahydrofuran-3-yl | —SO$_2$C$_6$H$_5$ |
| 188 | naphth-2-yl | 2-hydroxy-5-oxo-tetrahydrofuran-3-yl | —C(O)C$_6$H$_5$ |
| 189 | naphth-2-yl | 2-hydroxy-5-oxo-tetrahydrofuran-3-yl | —C(O)OCH$_2$C$_6$H$_5$ |
| 190 | naphth-2-yl | 2-hydroxy-5-oxo-tetrahydrofuran-3-yl | —C(O)NHC$_6$H$_5$ |
| 191 | isoquinolin-1-yl | 2-hydroxy-5-oxo-tetrahydrofuran-3-yl | —CH$_3$ |
| 192 | isoquinolin-1-yl | 2-hydroxy-5-oxo-tetrahydrofuran-3-yl | —CH$_2$CH$_3$ |
| 193 | isoquinolin-1-yl | 2-hydroxy-5-oxo-tetrahydrofuran-3-yl | —C(O)CH$_3$ |
| 194 | isoquinolin-1-yl | 2-hydroxy-5-oxo-tetrahydrofuran-3-yl | —SO$_2$CH$_3$ |
| 195 | isoquinolin-1-yl | 2-hydroxy-5-oxo-tetrahydrofuran-3-yl | —SO$_2$CH$_2$CH$_3$ |
| 196 | isoquinolin-1-yl | 2-hydroxy-5-oxo-tetrahydrofuran-3-yl | —SO$_2$CH(CH$_3$)$_2$ |
| 197 | isoquinolin-1-yl | 2-hydroxy-5-oxo-tetrahydrofuran-3-yl | —SO$_2$C$_6$H$_5$ |
| 198 | isoquinolin-1-yl | 2-hydroxy-5-oxo-tetrahydrofuran-3-yl | —C(O)C$_6$H$_5$ |
| 199 | isoquinolin-1-yl | 2-hydroxy-5-oxo-tetrahydrofuran-3-yl | —C(O)OCH$_2$C$_6$H$_5$ |
| 200 | isoquinolin-1-yl | 2-hydroxy-5-oxo-tetrahydrofuran-3-yl | —C(O)NHC$_6$H$_5$ |
| 201 | benzothiophen-2-yl | 2-hydroxy-5-oxo-tetrahydrofuran-3-yl | —CH$_3$ |
| 202 | benzothiophen-2-yl | 2-hydroxy-5-oxo-tetrahydrofuran-3-yl | —CH$_2$CH$_3$ |
| 203 | benzothiophen-2-yl | 2-hydroxy-5-oxo-tetrahydrofuran-3-yl | —C(O)CH$_3$ |
| 204 | benzothiophen-2-yl | 2-hydroxy-5-oxo-tetrahydrofuran-3-yl | —SO$_2$CH$_3$ |
| 205 | benzothiophen-2-yl | 2-hydroxy-5-oxo-tetrahydrofuran-3-yl | —SO$_2$CH$_2$CH$_3$ |
| 206 | benzothiophen-2-yl | 2-hydroxy-5-oxo-tetrahydrofuran-3-yl | —SO$_2$CH(CH$_3$)$_2$ |
| 207 | benzothiophen-2-yl | 2-hydroxy-5-oxo-tetrahydrofuran-3-yl | —SO$_2$C$_6$H$_5$ |
| 208 | benzothiophen-2-yl | 2-hydroxy-5-oxo-tetrahydrofuran-3-yl | —C(O)C$_6$H$_5$ |
| 209 | benzothiophen-2-yl | 2-hydroxy-5-oxo-tetrahydrofuran-3-yl | —C(O)OCH$_2$C$_6$H$_5$ |
| 210 | benzothiophen-2-yl | 2-hydroxy-5-oxo-tetrahydrofuran-3-yl | —C(O)NHC$_6$H$_5$ |
| 211 | 3-chlorophenyl | 2-hydroxy-5-oxo-tetrahydrofuran-3-yl | —CH$_3$ |
| 212 | 3-chlorophenyl | 2-hydroxy-5-oxo-tetrahydrofuran-3-yl | —CH$_2$CH$_3$ |
| 213 | 3-chlorophenyl | 2-hydroxy-5-oxo-tetrahydrofuran-3-yl | —C(O)CH$_3$ |
| 214 | 3-chlorophenyl | 2-hydroxy-5-oxo-tetrahydrofuran-3-yl | —SO$_2$CH$_3$ |
| 215 | 3-chlorophenyl | 2-hydroxy-5-oxo-tetrahydrofuran-3-yl | —SO$_2$CH$_2$CH$_3$ |
| 216 | 3-chlorophenyl | 2-hydroxy-5-oxo-tetrahydrofuran-3-yl | —SO$_2$CH(CH$_3$)$_2$ |
| 217 | 3-chlorophenyl | 2-hydroxy-5-oxo-tetrahydrofuran-3-yl | —SO$_2$C$_6$H$_5$ |
| 218 | 3-chlorophenyl | 2-hydroxy-5-oxo-tetrahydrofuran-3-yl | —C(O)C$_6$H$_5$ |

TABLE II-continued

| No. | R | R¹ | —L²—R¹⁰ |
|---|---|---|---|
| 219 | 3-chlorophenyl | 2-hydroxy-5-oxo-tetrahydrofuran-3-yl | —C(O)OCH$_2$C$_6$H$_5$ |
| 220 | 3-chlorophenyl | 2-hydroxy-5-oxo-tetrahydrofuran-3-yl | —C(O)NHC$_6$H$_5$ |
| 221 | 3-methylphenyl | 2-hydroxy-5-oxo-tetrahydrofuran-3-yl | —CH$_3$ |
| 222 | 3-methylphenyl | 2-hydroxy-5-oxo-tetrahydrofuran-3-yl | —CH$_2$CH$_3$ |
| 223 | 3-methylphenyl | 2-hydroxy-5-oxo-tetrahydrofuran-3-yl | —C(O)CH$_3$ |
| 224 | 3-methylphenyl | 2-hydroxy-5-oxo-tetrahydrofuran-3-yl | —SO$_2$CH$_3$ |
| 225 | 3-methylphenyl | 2-hydroxy-5-oxo-tetrahydrofuran-3-yl | —SO$_2$CH$_2$CH$_3$ |
| 226 | 3-methylphenyl | 2-hydroxy-5-oxo-tetrahydrofuran-3-yl | —SO$_2$CH(CH$_3$)$_2$ |
| 227 | 3-methylphenyl | 2-hydroxy-5-oxo-tetrahydrofuran-3-yl | —SO$_2$C$_6$H$_5$ |
| 228 | 3-methylphenyl | 2-hydroxy-5-oxo-tetrahydrofuran-3-yl | —C(O)C$_6$H$_5$ |
| 229 | 3-methylphenyl | 2-hydroxy-5-oxo-tetrahydrofuran-3-yl | —C(O)OCH$_2$C$_6$H$_5$ |
| 230 | 3-methylphenyl | 2-hydroxy-5-oxo-tetrahydrofuran-3-yl | —C(O)NHC$_6$H$_5$ |
| 231 | 3-fluorophenyl | 2-hydroxy-5-oxo-tetrahydrofuran-3-yl | —CH$_3$ |
| 232 | 3-fluorophenyl | 2-hydroxy-5-oxo-tetrahydrofuran-3-yl | —CH$_2$CH$_3$ |
| 233 | 3-fluorophenyl | 2-hydroxy-5-oxo-tetrahydrofuran-3-yl | —C(O)CH$_3$ |
| 234 | 3-fluorophenyl | 2-hydroxy-5-oxo-tetrahydrofuran-3-yl | —SO$_2$CH$_3$ |
| 235 | 3-fluorophenyl | 2-hydroxy-5-oxo-tetrahydrofuran-3-yl | —SO$_2$CH$_2$CH$_3$ |
| 236 | 3-fluorophenyl | 2-hydroxy-5-oxo-tetrahydrofuran-3-yl | —SO$_2$CH(CH$_3$)$_2$ |
| 237 | 3-fluorophenyl | 2-hydroxy-5-oxo-tetrahydrofuran-3-yl | —SO$_2$C$_6$H$_5$ |
| 238 | 3-fluorophenyl | 2-hydroxy-5-oxo-tetrahydrofuran-3-yl | —C(O)C$_6$H$_5$ |
| 239 | 3-fluorophenyl | 2-hydroxy-5-oxo-tetrahydrofuran-3-yl | —C(O)OCH$_2$C$_6$H$_5$ |
| 240 | 3-fluorophenyl | 2-hydroxy-5-oxo-tetrahydrofuran-3-yl | —C(O)NHC$_6$H$_5$ |

The compounds of Category II can be suitably prepared by the procedure outlined herein below in Scheme VII utilizing intermediate 7.

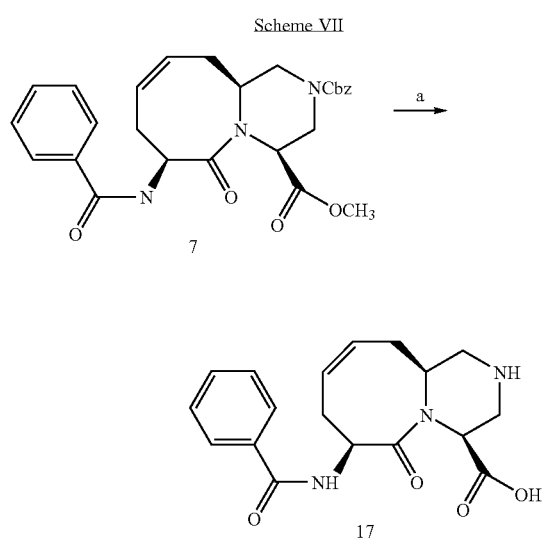

Scheme VII

Reagents and conditions: a) NaOH, THF/H$_2$O.

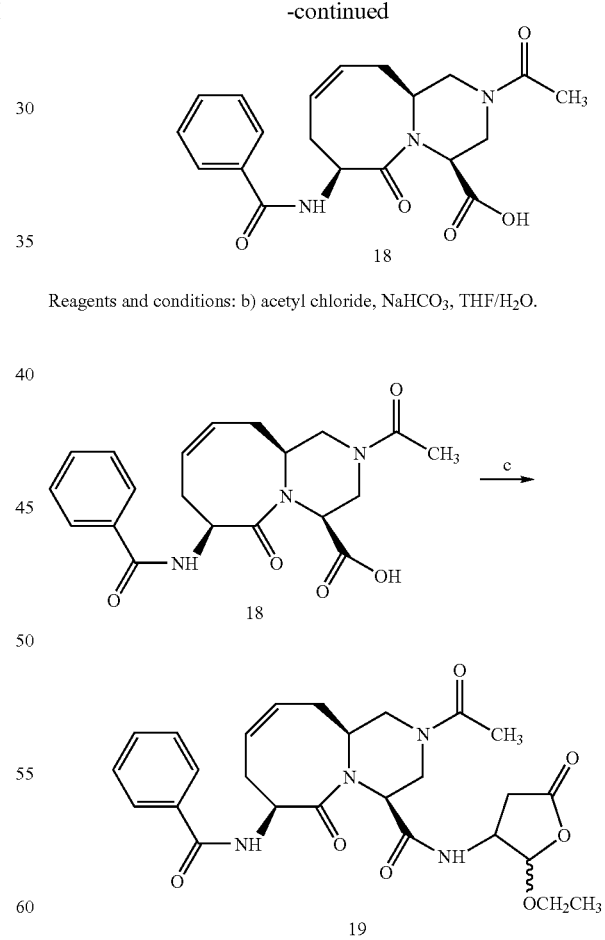

Reagents and conditions: b) acetyl chloride, NaHCO$_3$, THF/H$_2$O.

Reagents and conditions: c) (2-ethoxy-5-oxo-tetrahydrofurany-3-yl)-carbamic acid allyl ester; N,N-dimethylbarbituric acid, (Ph$_3$P)$_4$Pd, CH$_2$Cl$_2$, EDCl, HOBt.

EXAMPLE 5

(4S,6S,10aS)-2-Acetyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydro-furan-3-yl)-amide (19)

Preparation of (4S,6S,10aS)-6-benzoylamino-5-oxo-1,3,4,5,6,7,10,10a-octahydro-2H-2,4a-diaza-benzocyclooctene-4-carbocylic acid (17): Crude (4S,6S,10aS)-6-benzoylamino-5-oxo-1,3,4,5,6,7,10,10a-octahydro-2,4a-diaza-benzocyclo-octene-2,4-dicarbocylic acid 2-benzyl ester 4-methyl ester, 7, (0.49 g, 1.0 mmol) is dissolved in THF/H$_2$O (5 mL of 1:1) and NaOH (40 mg, 1 mmol) is added. The solution is stirred overnight then worked up for neutral product. The crude product obtained is used without further purification.

Preparation of (4S,6S,10aS)-2-acetyl-6-benzoylamino-5-oxo-1,3,4,5,6,7,10,10a-octahydro-2H-2,4a-diaza-benzocyclooctene-4-carboxylic acid (18): (4S,6S,10aS)-6-benzoylamino-5-oxo-1,3,4,5,6,7,10,10a-octahydro-2H-2,4a-diaza-benzocyclooctene-4-carbocylic acid, 17, prepared by the above procedure is dissolved in 5 mL of THF/H$_2$O and treated with NaHCO$_3$ (176 mg, 2.1 mmol) and acetyl chloride (0.08 mL, 1.1 mmol). After 30 min, the solution is diluted with EtOAc, washed with 1 N HCl and brine, and dried (MgSO$_4$). The solvent is removed in vacuo and the residue purified over silica (EtOAc/hexane) to afford the desired product Preparation of (4S,6S,10aS)-2-acetyl-6-benzoylamino-5-oxo-decahydro-2,4a-diaza-benzocyclooctene-4-carboxylic acid (2-ethoxy-5-oxo-tetrahydrofuran-3-yl)amide (19): A catalytic amount of Pd(Ph$_3$P)$_4$ is added to a solution of (2-Ethoxy-5-oxo-tetrahydrofuran-3-yl)-carbamic acid allyl ester (80 mg, 0.35 mmol) and N,N-dimethylbarbituric acid (109 mg, 0.70 mmol) in 2 mL CH$_2$Cl$_2$ at room temperature. The solution is stirred at rt for 15 minutes and (4S,6S,10aS)-2-acetyl-6-benzoylamino-5-oxo-1,3,4,5,6,7,10,10a-octahydro-2H-2,4a-diaza-benzocyclooctene-4-carbocylic acid, 18, (69 mg, 0.18 mmol) is added as a solution in 1 mL CH$_2$Cl$_2$, followed by 1-hydroxy-benzotriazole (94 mg, 0.70 mmol) and 1-(3-dimethyl-aminopropyl)-3-ethyl-carbodiimide hydrochloride (132 mg, 0.70 mmol). The solution is stirred for 5 hours then diluted with EtOAc, washed with saturated NaHCO$_3$, brine, dried (MgSO$_4$), and concentrated in vacuo. Purification over silica affords the desired product.

The compounds of this category wherein R$^1$ comprises the cysteine trap 2-hydroxy-5-oxo-tetrahydrofuran-3-yl can be prepared by the procedure outlined in Scheme VIII as indicated in the following example starting with compound 19.

The compounds which comprise this iteration of Category II can also comprise other cysteine traps, for example, the 2-hydroxy-5-oxo-tetrahydrofuran-3-yl cysteine trap which can be prepared by the procedure outlined in Scheme VIII beginning with the 2-ethoxy-5-oxo-tetrahydrofuran-3-yl cysteine trap. The example below converts compound 19 (analog 124 from Table II) to compound 12 (analog 164 from Table II).

Scheme VIII

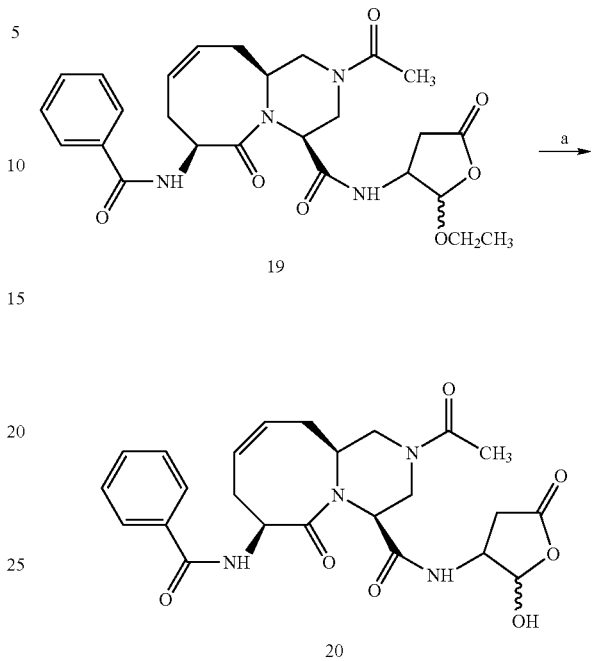

Reagents and conditions: a) TFA, acetonitrile/water.

EXAMPLE 6

(4S,6S10aS)-2-Acetyl-6-benzoylamino-5-oxo-1,3,4,5,4,6,7,10,10a-octahydro-2H-2,4a-diaza-benzocyclooctene-4-carboxylic acid (2-hydroxy-5-oxo-tetrahydro-furan-3-yl)-amide (20)

Preparation of (4S,6S,10aS)-2-acetyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide (20): A solution of (4S,6S,10aS)-2-acetyl-6-benzoylamino-5-oxo-decahydro-2,4a-diaza-benzocyclooctene-4-carboxylic acid (2-ethoxy-5-oxo-tetrahydrofuran-3-yl)amide, 19, (70 mg, 0.14 mmol) in acetonitrile/water is treated with trifluoroacetic acid. After stirring for 30 minutes the solution is concentrated in vacuo and the crude product purified by preparative reverse phase HPLC to afford the desired product as a white solid.

An alternative synthetic route for preparing the 4,6-disubstituted 5-oxo-1,3,4,5,6,7,10,10a-octahydro-2H-2,4a-diaza-benzocyclooctene scaffold is depicted in Scheme IX. This procedure begins with 3-amino-2-tert-butoxycarbonylamino-propionic acid and results in placing a 2-nitrobenzene sulfonyl unit onto the 8,6 fused ring scaffold. This unit, which in some instances is more easily removed than the carbobenzoyloxy unit depicted herein above, is utilized as a nitrogen protecting group from the beginning of the compound preparation.

Scheme IX

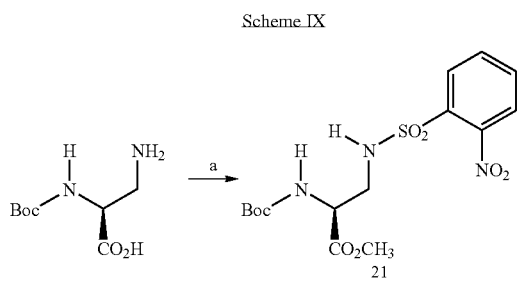

Reagents and conditions: a) i) 2-nitrobenzenesulfonyl chloride, NaHCO₃, THF/H₂O
ii) CH₂N₂, Et₂O; rt.

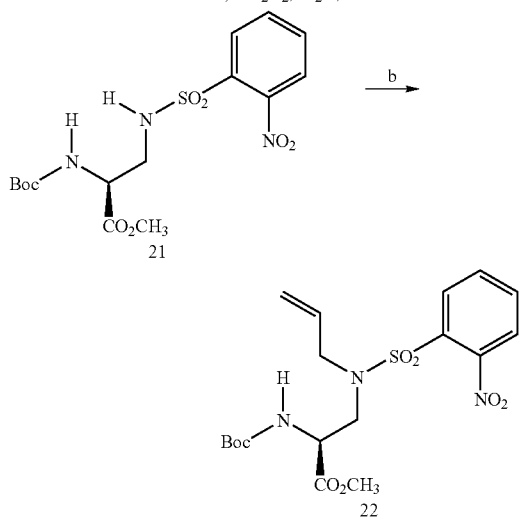

Reagents and conditions: b) allyl methyl carbonate, allyl palladium chloride, Ph₃P, THF

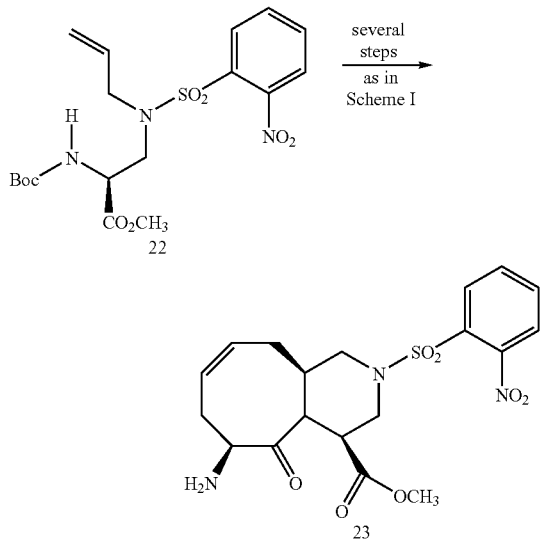

Compound 23 can be taken forward in the synthesis of Category II analogs in the same manner as depicted herein above in Scheme V and Scheme VII.

Preparation of 2-tert-butoxycarbonylamino-3-(2-nitro-benzenesulfonyl-amino)-propionic acid methyl ester (21): 3-Amino-2-tert-butoxycarbonylamino-propionic acid, pre- pared according to *J. Org. Chem.* 1997, 62, 6918, (38.8 g, 190.2 mmol) is dissolved in 1 L of 1:1 THF/H₂O and treated with NaHCO₃ (32 g, 380 mmol) followed by 2-nitrobenzenesulfonyl chloride (42.1 g, 190.2 mmol) of. The solution is stirred at rt overnight, concentrated to approximately 500 mL, and extracted with EtOAc. The organic extracts are washed with brine, dried (MgSO₄), filtered and concentrated in vacuo to afford 51.4 g of a white solid of the carboxylic acid. A portion of the carboxylic acid (35 g) is dissolved in Et₂O and treated with a freshly prepared ethereal solution of CH₂N₂ until a yellow color persisted. The reaction is quenched with HOAc and concentrated in vacuo. The crude residue is dissolved in EtOAc, washed with saturated NaHCO₃ and brine, dried (MgSO₄), filtered, and concentrated to afford 36.6 g of the desired product which is used without further purification. $^1$H NMR (CDCl₃) δ 8.18 (m, 1H), 7.92 (m, 1H), 7.80 (m, 2H), 5.87 (m, 1H), 5.38 (m, 1H), 4.42 (m, 1H), 3.83 (s, 3H), 3.56 (m, 2H), 1.47 (s, 9H).

Preparation of 3-[Allyl-(2-nitro-benzenesulfonyl)-amino]-2-tert-butoxycarbonylamino-propionic acid methyl ester (22): Crude 2-tert-butoxy-carbonylamino-3-(2-nitrobenzenesulfonylamino)-propionic acid methyl ester, 21, (41.8 g, 104 mmol) and allyl methyl carbonate (26.5 mL, 233.4 mmol) is dissolved in THF (400 mL) and treated with Ph₃P (2.6 g, 9.92 mmol) and allyl palladium chloride (820 mg, 2.25 mmol). The solution is stirred at rt overnight under nitrogen, concentrated, and purified directly over silica (5:1 to 2:1 hex/EtOAc) to afford 32 g of desired product. $^1$H NMR (CDCl₃) δ 8.09 (d, J=7.3 Hz, 1H), 7.74 (m, 3H), 5.65 (m, 1H), 5.27 (m, 3H), 4.20–3.60 (m, 4H), 3.80 (s, 3H), 1.48 (s, 9H).

Removal of the 2-nitorbenzenesulfonyl unit can be achieved by the following procedure.

Preparation of 6-[(Isoquinoline-1-carbonyl)-amino]-5-oxo-1,3,4,5,6,7,10,10a-octahydro-2H-2,4a-diazabenzo-cyclooctene-4-carboxylic acid methyl ester: To a solution of 6-[(isoquinoline-1-carbonyl)-amino]-2-(2-nitro-benzenesulfonyl)-5-oxo-1,3,4,5,6,7,10,10a-octahydro-2H-2,4a-diaza-benzocyclooctene-4-carboxylic acid methyl ester (1.5 g, 2.53 mmol) in DMF (55 mL) is added 4-mercaptophenol (1.28 g, 10.1 mmol) and K₂CO₃ (1.4 g, 10.1 mmol). The solution is stirred at rt for 12 hrs, diluted with EtOAc, washed with water and brine, dried (MgSO₄), filtered, and concentrated. The crude residue is purified by preparative reverse phase HPLC (CH₃CN/H₂O with 0.1% TFA) to yield 1.16 g of product as a TFA salt.

Other non-limiting examples of analogs belonging to Category II of the present invention include:

(4S,6S,10aS)-2-Carbobenzyloxy-6-[(naphthalene-2-carbonyl)-amino]-5-oxo-1,3,4,5,6,7,10,10 a-octahydro-2H-2,4a-diaza-benzocyclooctene-carboxylic acid (2-hydroxy-5-oxo-tetrahydrofuran-3-yl)-amide: $^1$H NMR (CD₃OD) δ 8.50 (s, 1H), 8.00 (m, 4H), 7.63 (m, 2H), 7.42 (m, 5H), 5.91 (m, 1H), 5.73 (m, 1H), 5.51 (m, 1H), 5.22 (br s, 2H), 5.05 (m, 1H), 4.60 (m, 3H), 4.34 (m, 1H), 3.82 (m, 1H), 3.58 (m, 1H), 3.15 (m, 1H), 2.80–2.40 (m, 6H); MS 627 (M+H)⁺.

(4S,6S,10aS)-6-Benzoylamino-4-(2-hydroxy-5-oxo-tetrahydro-furan-3-ylcarbamoyl)-5-oxo-1,3,4,5,6,7,10,10a-octahydro-2,4a-diaza-benzocyclooctene-2-carboxylic acid benzyl ester: $^1$H NMR (CDCl₃) δ 7.87–7.85 (d, J=6.6 Hz, 2H), 7.55–7.39 (m, 8H), 5.82–5.73 (m, 2H), 5.52–5.50 (m, 2H), 5.21 (broad s, 2H), 4.94–4.87 (m, 1H), 4.71–4.67 (d, J=13.2 Hz, 2H), 4.05 (broad s, 1H), 3.38–3.35 (broad s, 2H), 2.62–2.48 (m, 9H); MS 577 (M+H)⁺.

(4S,6S,10aS)-2-Carbobenzyloxy-6-[(isoquinoline-1-carbonyl)-amino]-5-oxo-1,3,4,5,6,7,10,10a-octahydro-2H-2,4a-diaza-benzocyclooctene-carboxylic acid (2-hydroxy-5- oxo-tetrahydrofuran-3-yl)-amide: $^1$H NMR (CD$_3$OD) δ 9.16 (d, J=8.4 Hz, 1H), 8.55 (d, J=5.5 Hz, 1H), 7.99 (m, 2H), 7.78 (m, 2H), 7.42 (m, 5H), 5.88 (m, 1H), 5.72 (m, 1H), 5.52 (m, 1H), 5.21 (s, 2H), 5.05 (m, 1H), 4.65 (m, 3H), 4.34 (m, 1H), 3.90 (m, 1H), 3.54 (m, 1H), 3.30 (m, 2H), 2.80–2.40 (m, 5H); MS 628 (M+H)$^+$.

(4S,6S,10aS)-2-Benzenesulfonyl-6-[isoquinoline-1-carbonyl)-amino]-5-oxo-1,3,4,5,6,7,10,10a-octahydro-2H-2,4a-diaza-benzocyclooctene-4-carboxylic acid (2-hydroxy-5-oxo-tetrahydro-furan-3-yl)-amide: $^1$H NMR (CD$_3$OD) δ 9.10 (d, J=8.4 Hz, 1H), 8.54 (s, 1H), 8.02 (m, 1H), 7.89–7.64 (m, 7H), 5.57 (m, 2H), 5.39 (m, 1H), 5.2–4.6 (series of m, 2H), 4.34 (m, 1H), 3.65 (m, 2H), 3.25 (m, 2H), 2.91–2.47 (m, 7H); MS 634 (M+H)$^+$.

(4S,6S,10aS)-2-Benzenesulfonyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)-amide: $^1$H NMR (CD$_3$OD) δ 7.87 (m, 4H), 7.67 (m, 4H), 7.55 (m, 2H), 5.72 (m, 2H), 5.34 (m, 2H), 5.1–4.6 (series of m, 2H), 4.34 (m, 1H), 3.63 (m, 1H), 3.17 (m, 2H), 2.81–2.43 (m, 7H); MS 583 (M+H)$^+$.

(4S,6S,10aS)-2-Benzenesulfonyl-6-[(naphthalene-2-carbonyl)-amino]-5-oxo-1,3,4,5,6,7,10,10a-octahydro-2H-2,4a-diaza-benzocyclooctene-4-carboxylic acid (2-hydroxy-5-oxo-tetrahydro-furan-3-yl)-amide: $^1$H NMR (CD$_3$OD) δ 8.46 (s, 1H), 7.94 (m, 6H), 7.66 (m, 5H), 5.77 (m, 1H), 5.68 (m, 1H), 5.39 (m, 1H), 5.02–4.63 (series of m, 2H), 4.31 (m, 2H), 3.64 (m, 1H), 3.20 (m, 2H), 2.82–2.40 (series of m, 7H); MS 633 (M+H)$^+$.

As it relates to analogs which comprise Category I and Category II of the present invention, scaffolds having, for example, the general formula:

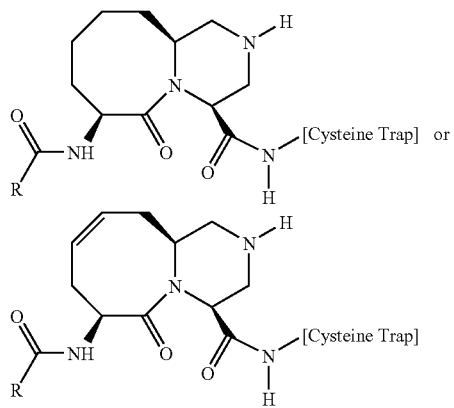

wherein R$^9$ is hydrogen, are also analogs according to the present invention, and therefore, the combination of a suitable R units and Cysteine Traps with the above scaffolds will provide analogs according to the present invention. In addition, substitutions for the R$^9$ unit hydrogen not specifically exemplified in the specification are still, however, within the scope of the present invention.

Category III of the interleukin-1β converting enzyme inhibitors according to the present invention relates to compound comprising a 4,6-substituted 3,4,6,7,10,10a-hexahydro-1H-2-oxa[4a]aza-benzocycloocten-5-one scaffold having the formula:

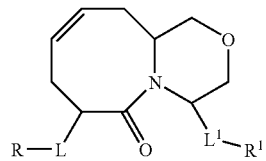

one iteration of the first aspect of this Category comprises scaffolds having the indicated stereochemistry. Table III relates to non-limiting examples of analogs comprising a first aspect of this category, said analogs having the formula:

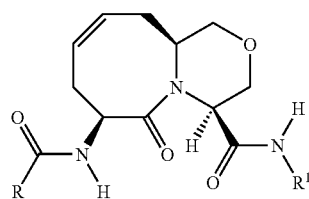

wherein R and R$^1$ are defined in Table III herein below.

TABLE III

| No. | R | R$^1$ |
|---|---|---|
| 241 | phenyl | 2-hydroxy-5-oxo-tetrahydrofuran-3-yl |
| 242 | phenyl | 2-ethoxy-5-oxo-tetrahydrofuran-3-yl |
| 243 | quinolin-2-yl | 2-hydroxy-5-oxo-tetrahydrofuran-3-yl |
| 244 | quinolin-2-yl | 2-ethoxy-5-oxo-tetrahydrofuran-3-yl |
| 245 | benzothiophen-2-yl | 2-hydroxy-5-oxo-tetrahydrofuran-3-yl |
| 246 | benzothiophen-2-yl | 2-ethoxy-5-oxo-tetrahydrofuran-3-yl |
| 247 | 2-thienyl | 2-hydroxy-5-oxo-tetrahydrofuran-3-yl |
| 248 | 2-thienyl | 2-ethoxy-5-oxo-tetrahydrofuran-3-yl |
| 249 | isoquinolin-1-yl | 2-hydroxy-5-oxo-tetrahydrofuran-3-yl |
| 250 | isoquinolin-1-yl | 2-ethoxy-5-oxo-tetrahydrofuran-3-yl |
| 251 | naphth-1-yl | 2-hydroxy-5-oxo-tetrahydrofuran-3-yl |
| 252 | naphth-1-yl | 2-ethoxy-5-oxo-tetrahydrofuran-3-yl |
| 253 | naphth-2-yl | 2-hydroxy-5-oxo-tetrahydrofuran-3-yl |
| 254 | naphth-2-yl | 2-ethoxy-5-oxo-tetrahydrofuran-3-yl |
| 255 | 2-chlorophenyl | 2-hydroxy-5-oxo-tetrahydrofuran-3-yl |
| 256 | 2-chlorophenyl | 2-ethoxy-5-oxo-tetrahydrofuran-3-yl |
| 257 | 3-chlorophenyl | 2-hydroxy-5-oxo-tetrahydrofuran-3-yl |
| 258 | 3-chlorophenyl | 2-ethoxy-5-oxo-tetrahydrofuran-3-yl |
| 259 | 4-chlorophenyl | 2-hydroxy-5-oxo-tetrahydrofuran-3-yl |
| 260 | 4-chlorophenyl | 2-ethoxy-5-oxo-tetrahydrofuran-3-yl |
| 261 | 2-fluorophenyl | 2-hydroxy-5-oxo-tetrahydrofuran-3-yl |
| 262 | 2-fluorophenyl | 2-ethoxy-5-oxo-tetrahydrofuran-3-yl |
| 263 | 3-fluorophenyl | 2-hydroxy-5-oxo-tetrahydrofuran-3-yl |
| 264 | 3-fluorophenyl | 2-ethoxy-5-oxo-tetrahydrofuran-3-yl |
| 265 | 4-fluorophenyl | 2-hydroxy-5-oxo-tetrahydrofuran-3-yl |
| 266 | 4-fluorophenyl | 2-ethoxy-5-oxo-tetrahydrofuran-3-yl |
| 267 | 3,4-difluorophenyl | 2-hydroxy-5-oxo-tetrahydrofuran-3-yl |
| 268 | 3,4-difluorophenyl | 2-ethoxy-5-oxo-tetrahydrofuran-3-yl |
| 269 | 4-fluorothienyl | 2-hydroxy-5-oxo-tetrahydrofuran-3-yl |
| 270 | 4-fluorothienyl | 2-ethoxy-5-oxo-tetrahydrofuran-3-yl |
| 271 | 2-aminopyrimidinyl | 2-hydroxy-5-oxo-tetrahydrofuran-3-yl |
| 272 | 2-aminopyrimidinyl | 2-ethoxy-5-oxo-tetrahydrofuran-3-yl |
| 273 | 2-phenylamino-4-pyrimidinyl | 2-hydroxy-5-oxo-tetrahydrofuran-3-yl |
| 274 | 2-phenylamino-4-pyrimidinyl | 2-ethoxy-5-oxo-tetrahydrofuran-3-yl |
| 275 | 2-phenoxy-4-pyrimidinyl | 2-hydroxy-5-oxo-tetrahydrofuran-3-yl |
| 276 | 2-phenoxy-4-pyrimidinyl | 2-ethoxy-5-oxo-tetrahydrofuran-3-yl |
| 277 | 2-benzyloxy-4-pyrimidinyl | 2-hydroxy-5-oxo-tetrahydrofuran-3-yl |
| 278 | 2-benzyloxy-4-pyrimidinyl | 2-ethoxy-5-oxo-tetrahydrofuran-3-yl |
| 279 | 2-methoxy-4-pyrimidinyl | 2-hydroxy-5-oxo-tetrahydrofuran-3-yl |
| 280 | 2-methoxy-4-pyrimidinyl | 2-ethoxy-5-oxo-tetrahydrofuran-3-yl |
| 281 | isoquinolin-3-yl | 2-hydroxy-5-oxo-tetrahydrofuran-3-yl |
| 282 | isoquinolin-3-yl | 2-ethoxy-5-oxo-tetrahydrofuran-3-yl |

TABLE III-continued

| No. | R | R¹ |
|---|---|---|
| 283 | 2-phenylamino-4-pyridinyl | 2-hydroxy-5-oxo-tetrahydrofuran-3-yl |
| 284 | 2-phenylamino-4-pyridinyl | 2-ethoxy-5-oxo-tetrahydrofuran-3-yl |
| 285 | 2-phenoxy-4-pyridinyl | 2-hydroxy-5-oxo-tetrahydrofuran-3-yl |
| 286 | 2-phenoxy-4-pyridinyl | 2-ethoxy-5-oxo-tetrahydrofuran-3-yl |
| 287 | 2-benzyloxy-4-pyridinyl | 2-hydroxy-5-oxo-tetrahydrofuran-3-yl |
| 288 | 2-benzyloxy-4-pyridinyl | 2-ethoxy-5-oxo-tetrahydrofuran-3-yl |
| 289 | 2-methoxy-4-pyridinyl | 2-hydroxy-5-oxo-tetrahydrofuran-3-yl |
| 290 | 2-methoxy-4-pyridinyl | 2-ethoxy-5-oxo-tetrahydrofuran-3-yl |
| 291 | 4-hydroxyphenyl | 2-hydroxy-5-oxo-tetrahydrofuran-3-yl |
| 292 | 4-hydroxyphenyl | 2-ethoxy-5-oxo-tetrahydrofuran-3-yl |
| 293 | 2-methylphenyl | 2-hydroxy-5-oxo-tetrahydrofuran-3-yl |
| 294 | 2-methylphenyl | 2-ethoxy-5-oxo-tetrahydrofuran-3-yl |
| 295 | 3-methylphenyl | 2-hydroxy-5-oxo-tetrahydrofuran-3-yl |
| 296 | 3-methylphenyl | 2-ethoxy-5-oxo-tetrahydrofuran-3-yl |
| 297 | 4-methylphenyl | 2-hydroxy-5-oxo-tetrahydrofuran-3-yl |
| 298 | 4-methylphenyl | 2-ethoxy-5-oxo-tetrahydrofuran-3-yl |
| 299 | 2-trifluoromethylphenyl | 2-hydroxy-5-oxo-tetrahydrofuran-3-yl |
| 300 | 2-trifluoromethylphenyl | 2-ethoxy-5-oxo-tetrahydrofuran-3-yl |
| 301 | 3-trifluoromethylphenyl | 2-hydroxy-5-oxo-tetrahydrofuran-3-yl |
| 302 | 3-trifluoromethylphenyl | 2-ethoxy-5-oxo-tetrahydrofuran-3-yl |
| 303 | 4-trifluoromethylphenyl | 2-hydroxy-5-oxo-tetrahydrofuran-3-yl |
| 304 | 4-trifluoromethylphenyl | 2-ethoxy-5-oxo-tetrahydrofuran-3-yl |
| 305 | phenylamino | 2-hydroxy-5-oxo-tetrahydrofuran-3-yl |
| 306 | phenylamino | 2-ethoxy-5-oxo-tetrahydrofuran-3-yl |
| 307 | 2-methoxyphenyl | 2-hydroxy-5-oxo-tetrahydrofuran-3-yl |
| 308 | 2-methoxyphenyl | 2-ethoxy-5-oxo-tetrahydrofuran-3-yl |
| 309 | 3-methoxyphenyl | 2-hydroxy-5-oxo-tetrahydrofuran-3-yl |
| 310 | 3-methoxyphenyl | 2-ethoxy-5-oxo-tetrahydrofuran-3-yl |
| 311 | 4-methoxyphenyl | 2-hydroxy-5-oxo-tetrahydrofuran-3-yl |
| 312 | 4-methoxyphenyl | 2-ethoxy-5-oxo-tetrahydrofuran-3-yl |

The compounds of Category III can be prepared by the procedure outlined herein below, utilizing intermediate 29 which can be synthesized by the procedure described in Scheme X.

Scheme X

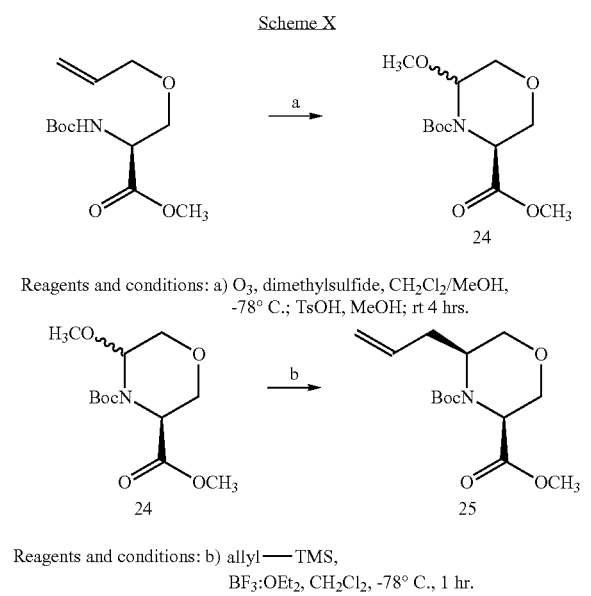

Reagents and conditions: a) O₃, dimethylsulfide, CH₂Cl₂/MeOH, −78° C.; TsOH, MeOH; rt 4 hrs.

Reagents and conditions: b) allyl—TMS, BF₃:OEt₂, CH₂Cl₂, −78° C., 1 hr.

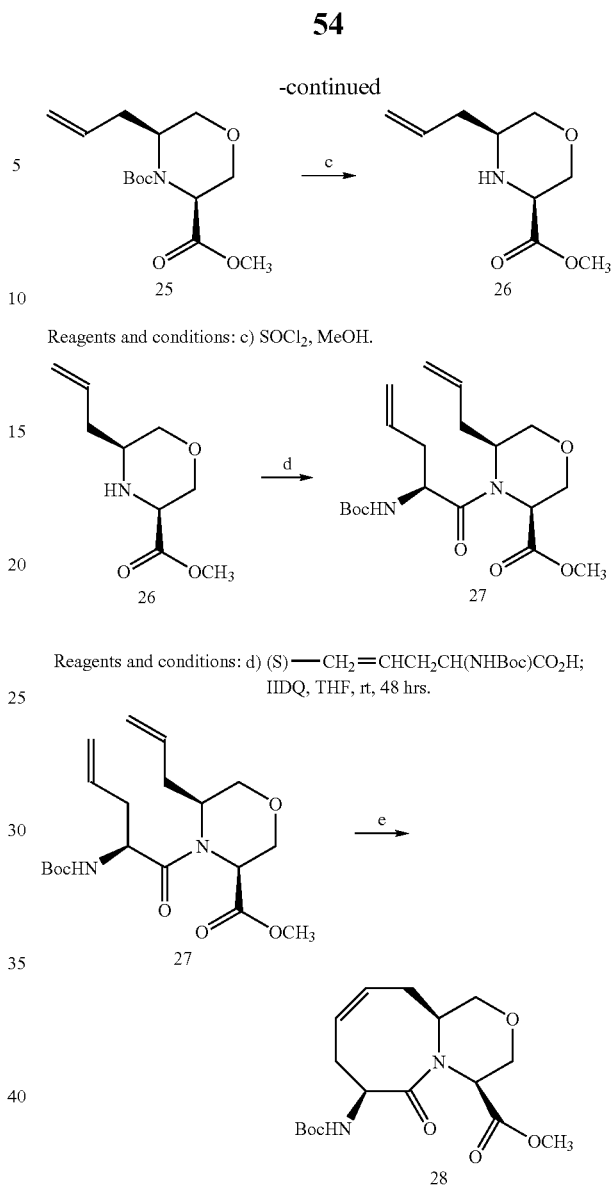

Reagents and conditions: c) SOCl₂, MeOH.

Reagents and conditions: d) (S)—CH₂=CHCH₂CH(NHBoc)CO₂H; IIDQ, THF, rt, 48 hrs.

Reagents and conditions: e) Grubbs catalyst; CH₂Cl₂, 40° C., 12 hrs.

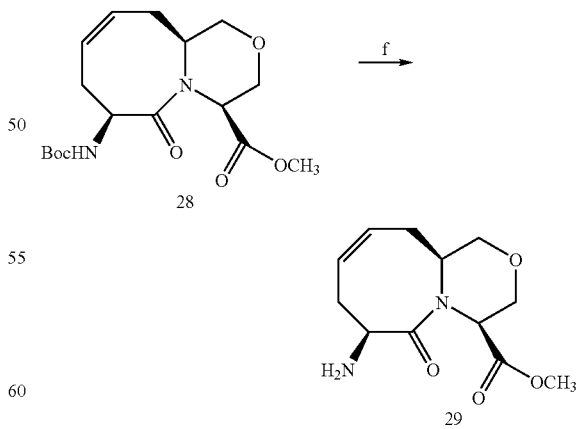

Reagents and conditions: f) TFA, CH₂Cl₂.

The starting material for the preparation of Category II analogs, 3-allyloxy-2-tert-butoxycarbonylamino-propionic acid methyl ester, can be prepared via the procedure described by F. L. Zumpe et al., *Synthesis*, 10, p. 1785–1791 (1999).

Preparation of 5-methoxymorpholine-3,4-dicarboxylic acid 4-tert-butyl ester 3-methyl ester (24): A solution containing 3-allyloxy-2-tert-butoxycarbonylamino-propionic acid methyl ester (30.0 g, 116 mmol) in 550 mL of 10:1 CH$_2$Cl$_2$/MeOH is cooled to −78° C. and purged with ozone until a blue color persisted (45 min). The solution is then purged with N$_2$ to remove excess ozone and treated with dimethylsulfide (35 mL). The solution is allowed to warm to room temperature overnight and the next morning concentrated in vacuo. The resulting solid is re-dissolved in 400 mL of MeOH and treated with 500 mg of p-toluenesulfonic acid. After stirring for 4 hours, the volume of solvent is reduced to about 100 mL and toluene (250 mL) is added. The solution is re-concentrate in vacuo and purified over silica gel (EtOAc/hexane) to afford 25 g (78%) of the desired product. $^1$H NMR (CDCl$_3$) δ 5.21 (br s, 0.5H), 5.05 (br s, 0.5H), 4.65–4.45 (m, 2H), 3.98 (dd, J=12.8, 12.5 Hz, 1H), 3.79 (s, 3H), 3.66 (br d, J=11.3 Hz, 1H), 3.56 (dd, J=9.9, 9.9 Hz, 1H), 3.42 (s, 3H), 1.54 (s, 0.5×9H), 1.50 (s, 0.5×9H); MS 276 (M+H)$^+$.

Preparation of 5-allylmorpholine-3,4-dicarboxylic acid 4-tert-butyl ester 3-carboxylic acid methyl ester (25): 5-methoxymorpholine-3,4-dicarboxylic acid 4-tert-butyl ester 3-methyl ester, 24, (30 g, 110 mmol) is dissolved in 550 mL of CH$_2$Cl$_2$ and cooled to −78° C. Allyltrimethylsilane (34.9 mL, 220 mmol) and BF$_3$OEt$_2$ (15.3 mL, 121 mmol) are added sequentially and the solution is stirred at −78° C. for 1 h. The cold reaction solution is then poured into 500 mL of water. The organic layer is isolated and concentrated in vacuo. The crude product is used without further purification.

Preparation of 5-allylmorpholine-3-carboxylic acid methyl ester (26): The crude 5-allyl-morpholine-3,4-dicarboxylic acid 4-tert-butyl ester 3-carboxylic acid methyl ester, 25, obtained above is dissolved in MeOH (500 mL), cooled to 0° C., and treated with 30 mL of SOCl$_2$. The solution is stirred at room temperature for 12 hours then concentrated in vacuo to afford the HCl salt of the crude product which is subsequently treated with saturated NaHCO$_3$ and partitioned into EtOAc to provide 14.7 g (72%) of the desired product, which is used in the next step without further purification. $^1$H NMR (CDCl$_3$) δ 5.79 (m, 1H), 5.18 (m, 2H), 4.14 (dd, J=11.0, 3.3 Hz, 1H), 3.81 (dd, J=11.0, 3.0 Hz, 1H), 3.76 (s, 3H), 3.71 (dd, J=11.3, 3.3 Hz, 1H), 3.41 (dd, J=10.6, 10.6 Hz, 1H), 3.14 (dd, J=10.6, 10.6 Hz, 1H), 2.92 (m, 1H), 2.18 (m, 2H); MS 186 (M+H)$^+$.

Preparation of 5-allyl-4-(2-N-Boc-amino-pent-4-enoyl) morpholine-3-carboxylic acid methyl ester (27): A solution containing 5-allylmorpholine-3-carboxylic acid methyl ester, 26, (14.7 g, 79.5 mmol), N-Boc-allylglycine (34.4 g, 160 mmol), IIDQ (48.5 g, 160 mmol) and THF (200 mL) is stirred at room temperature for 48 hours. The reaction solution is then diluted with EtOAc, washed with 1 N HCl, saturated NaHCO$_3$, and brine. The organic layer is concentrated in vacuo and purified over silica gel (EtOAc/hexane) to afford 18.5 g (61%) of the desired product. $^1$H NMR (CDCl$_3$) δ 5.81 (m, 2H), 5.18 (m, 5H), 4.63 (d, J=12.1 Hz, 1H), 4.22 (m, 1H), 3.97 (dd, J=11.0, 11.0 Hz, 1H), 3.79 (s, 3H), 3.66–3.48 (m, 2H), 2.70–2.28 (m, 5H), 1.46 (s, 9H); MS 383 (M+H)$^+$.

Preparation of (4S,6S,10aS)-6-N-Boc-amino-5-oxo-1,3,4,5,6,7,7,10,10a-octahydro-2-oxa-[4a]-azabenzocyclooctene-4-carboxylic acid methyl ester (28): Grubbs catalyst (1.8 g. 2.2 mmol) is added to a solution of 5-allyl-4-(2-N-Boc-amino-pent-4-enoyl)morpholine-3-carboxylic acid methyl ester, 27, (5.82 g, 15.2 mmol) in CH$_2$Cl$_2$ (200 mL). The reaction mixture is refluxed for 12 hours, then cooled and 1 mL of DMSO is added, and stirring continued at room temperature for another 12 hours. The solvent is removed in vacuo and the residue purified over silica gel (EtOAc/hexane) to afford 3.0 g (56%) of the desired product. $^1$H NMR (CDCl$_3$) δ 5.92 (br d, J=6.9 Hz, 1H), 5.66 (br s, 2H), 4.90 (m, 2H), 4.55 (d, J=11.7 Hz, 1H), 4.30 (br d, J=11.8 Hz, 1H), 3.86–3.64 (m, 3H), 3.77 (s, 3H), 2.92 (m, 2H), 2.48 (m, 1H), 2.31 (br d, J=16.5 Hz, 1H), 1.48 (s, 9H); $^{13}$C NMR (CDCl$_3$) 172.9, 170.5, 155.5, 128.9, 124.3, 80.0, 70.7, 67.9, 52.6, 51.6, 51.2, 51.0, 36.3, 33.4, 28.6(3C); MS 355 (M+H)$^+$.

Preparation of (4S,6S,10aS)-6-amino-5-oxo-1,3,4,5,6,7,7,10,10a-octahydro-2-oxa-[4a]-azabenzocyclooctene-4-carboxylic acid methyl ester (29): (4S,6S,10aS)-6-N-Boc-amino-5-oxo-1,3,4,5,6,7,7,10,10a-octahydro-2-oxa-[4a]-azabenzocyclooctene-4-carboxylic acid methyl ester, 28, is dissolved in CH$_2$Cl$_2$ and treated with excess TFA. The solution is stirred for 3 hours and then concentrated in vacuo to yield the desired product as a TFA salt which can be used without further purification.

Intermediate 29, prepared by the procedure herein above, represents the core of the Category III scaffold. The formulator can now attach the desired R unit to the scaffold, for example, a isoquinolin-1-yl unit as illustrated in Scheme XI herein below.

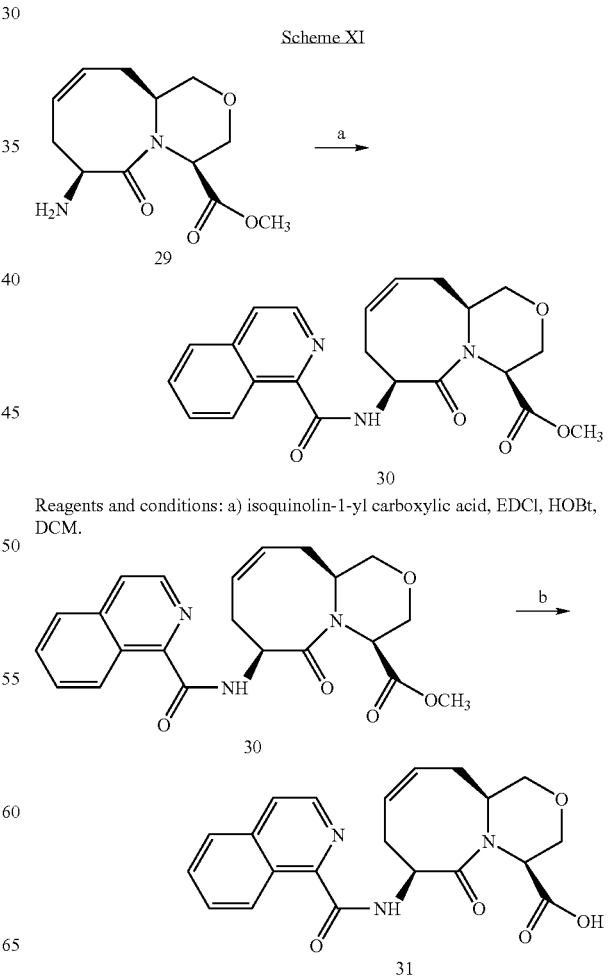

Reagents and conditions: a) isoquinolin-1-yl carboxylic acid, EDCl, HOBt, DCM.

-continued
Reagents and conditions: b) LiOH, THF/H₂O, rt, 12 hrs.

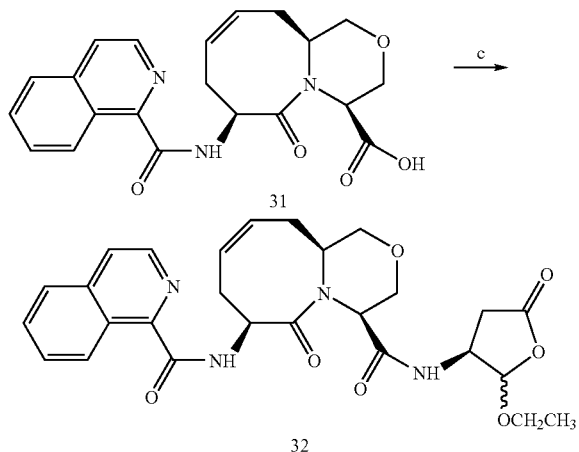

Reagents and conditions: c) (2-ethoxy-5-oxo-tetrahydrofurany-3-yl)-carbamic acid allyl ester; N,N-dimethylbarbituric acid, (Ph₃P)₄Pd, CH₂Cl₂, EDCl, HOBt.

EXAMPLE 7

(4S,6S,10aS)-6-Isoquinoline-1-carbonyl)amino]-5-oxo-1,3,4,5,6,7,10,10a-octahydro-2-oxo-[4a]-aza-benzocyclooctene-4-carboxylic acid (2-ethoxy-5-oxo-tetrahydrofuran-3-yl)amide (32)

Preparation of 6-[(isoquinoline-1-carbonyl)-amino]-5-oxo-1,3,4,5,6,7,10,10a-octahydro-2-oxa-[4a]-azabenzocyclooctene-4-carboxylic acid methyl ester (30): 6-amino-5-oxo-1,3,4,5,6,7,10,10a-octahydro-2-oxa-[4a]-azabenzocyclooctene-4-carboxylic acid methyl ester, 29, (0.62 g, 1.68 mmol) is dissolved in 1:1 CH₂Cl₂/DMF and 1-isoquinolinecarboxylic acid (1.4 g, 8.1 mmol), 1-hydroxybenzotriazole (0.35 g, 2.6 mmol), and 1-(3-dimethyl-aminopropyl)-3-ethyl-carbodiimide hydrochloride (0.5 g, 2.6 mmol) are added. The resulting solution is stirred at room temperature for 12 hours, diluted with EtOAc, washed with saturated NaHCO₃ then brine, and dried (MgSO₄). The solvent is removed in vacuo and the resulting residue is purified over silica gel (EtOAc/hexane) to afford 370 mg (54%) of the desired product. $^1$H NMR (CDCl₃) δ 9.48 (d, J=7.8 Hz, 1H), 9.40 (d, J=6.9 Hz, 1H), 8.45 (d, J=5.4 Hz, 1H), 7.74 (m, 2H), 7.64 (m, 2H), 5.68 (br s, 2H), 5.37 (m, 1H), 4.85 (d, J=4.5 Hz, 1H), 4.43 (m, 2H), 3.78–3.58 (m, 3H), 3.71 (s, 3H), 3.12 (m, 1H), 2.84 (m, 1H), 2.60 (m, 1H), 2.30 (d, J=16.5 Hz, 1H); MS 410 (M+H)⁺.

Preparation of 6-[(isoquinoline-1-carbonyl)amino]-5-oxo-1,3,4,5,6,7,10,10a-octahydro-2-oxa-[4a]-aza-benzocyclooctene-4-carboxylic acid (31): A solution of 6-[(isoquinoline-1-carbonyl)-amino]-5-oxo-1,3,4,5,6,7,10,10a-octahydro-2-oxa-[4a]-azabenzocyclooctene-4-carboxylic acid methyl ester, 30, (370 mg, 0.9 mmol) in 3:1 THF/H₂O is treated with excess LiOH (360 mg, 8.6 mmol) and stirred for 12 hours at room temperature. The solution is then acidified and the aqueous layer extracted with EtOAc. The EtOAc layer is dried (MgSO₄) and concentrated in vacuo to afford 250 mg (70%) of the desired product.

Preparation of 6-[(isoquinoline-1-carbonyl)amino]-5-oxo-1,3,4,5,6,7,10,10a-octahydro-2-oxa-[4a]-aza-benzocyclooctene-4-carboxylic acid (2-ethoxy-5-oxo-tetrahydro-furan-3-yl)-amide (32): A catalytic amount of Pd(Ph₃P)₄ is added to a solution of (2-ethoxy-5-oxo-tetrahydrofuran-3-yl)-carbamic acid allyl ester (338 mg, 1.48 mmol) and N,N-dimethylbarbituric acid (483 mg, 3.1 mmol) in CH₂Cl₂ (5 mL) at room temperature. The solution is stirred for 15 min then 6-[(isoquinoline-1-carbonyl)amino]-5-oxo-1,3,4,5,6,7,10,10a-octahydro-2-oxa-[4a]-aza-benzocyclooctene-4-carboxylic acid, 31, (200 mg) as prepared above is added as a solution in CH₂Cl₂ (1 mL) followed by 1-hydroxybenzotriazole (416 mg, 3.1 mmol) and 1-(3-dimethyl-aminopropyl)-3-ethyl-carbodiimide hydrochloride (3 hours, then diluted with EtOAc, washed with saturated NaHCO₃, brine, dried (MgSO₄), and concentrated in vacuo to afford the desired product in sufficient purity to be used directly.

The compounds which comprise this aspect of Category III can also comprise other cysteine traps, for example, the 2-hydroxy-5-oxo-tetrahydrofuran-3-yl cysteine trap which can be prepared by the procedure outlined in Scheme VIII beginning with the 2-ethoxy-5-oxo-tetrahydrofuran-3-yl cysteine trap. The example below converts compound 32 (analog 250 from Table III) to compound 33 (analog 249 from Table III).

Scheme XII

Reagents and conditions: a) TFA, acetonitrile/water.

EXAMPLE 8

(4S,6S,10aS)-6-[Isoquinoline-1-carbonyl)amino]-5-oxo-1,3,4,5,6,7,10,10a-octahydro-2-oxo-[4a]-aza-benzocyclooctene-4-carboxylic acid (2-ethoxy-5-oxo-tetrahydrofuran-3-yl) amide (33)

Preparation of (4S,6S,10aS)-6-[(isoquinoline-1-carbonyl)amino]-5-oxo-1,3,4,5,6,7,10,10a-octahydro-2-oxa-[4a]-aza-benzocyclooctene-4-carboxylic acid (2-hydroxy-5-oxo-tetrahydro-furan-3-yl)-amide (33): To a solution of (4S,6S,10aS)-6-[(isoquinoline-1-carbonyl)amino]-5-oxo-1,3,4,5,6,7,10,10a-octahydro-2-oxa-[4a]-aza-benzocyclooctene-4-carboxylic acid (2-ethoxy-5-oxo-tetrahydro-furan-3-yl)-amide, 32, from above in CH₃CN/H₂O is added trifluoroacetic acid. After stirring for 30 minutes the solution is concentrated in vacuo and the crude product purified by preparative reverse phase HPLC to afford 63 mg (25% from 31) of the desired product. $^1$H NMR (CD₃OD) δ 9.15 (d, J=8.4 Hz, 1H), 8.55 (d, J=5.7 Hz, 1H), 8.01 (m, 2H), 7.78

(m, 2H), 5.78 (m, 1H), 5.65 (m, 1H), 5.50 (m, 1H), 4.80–4.20 (series of m, 5H), 3.83 (br s, 2H), 3.68 (m, 1H), 3.29 (m, 1H), 2.89 (m, 1H), 2.73–2.44 (m, 4H); MS 495 (M+H)+.

The following are non-limiting examples of the first aspect of Category III analogs according to the present invention.

(4S,6S,10aS)-6-[(2-chlorobenzoyl)amino]-5-oxo-1,3,4,5,6,7,10,10a-octahydro-2-oxa-[4a]-aza-benzocyclooctene-4-carboxylic acid (2-hydroxy-5-oxo-tetrahydro-furan-3-yl)-amide: $^1$H NMR (CD$_3$OD) δ 7.62 (dd, J=7.0, 1.8 Hz, 1H), 7.48 (m, 3H), 5.75 (m, 2H), 5.44 (m, 1H), 4.80–4.22 (m, 5H), 3.83 (br s, 2H), 3.66 (dd, J=11.7, 4.4 Hz, 1H), 3.24 (m, 1H), 2.88 (m, 1H), 2.64 (m, 1H), 2.48 (m, 3H); MS 478, 480 (M+H)+.

(4S,6S,10aS)-6-[(3-chlorobenzoyl)amino]-5-oxo-1,3,4,5,6,7,10,10a-octahydro-2-oxa-[4a]-aza-benzocyclooctene-4-carboxylic acid (2-hydroxy-5-oxo-tetrahydro-furan-3-yl)-amide: $^1$H NMR (CD$_3$OD) δ 7.96 (dd, J=1.8, 1.4 Hz, 1H), 7.86 (ddd, J=7.7, 1.4, 1.1 Hz, 1H), 7.61 (br d, J=8.0 Hz, 1H), 7.52 (dd, J=8.0, 7.7 Hz, 1H), 5.56 (m, 1H), 5.53 (m, 1H), 5.49 (m, 1H), 4.80–4.20 (m, 5H), 3.83 (br s, 2H), 3.65 (m, 1H), 3.22 (m, 1H), 2.89 (m, 1H), 2.66 (m, 1H), 2.50 (m, 3H); MS 478, 480 (M+H)+.

(4S,6S,10aS)-6-[(4-chlorobenzoyl)amino]-5-oxo-1,3,4,5,6,7,10,10a-octahydro-2-oxa-[4a]-aza-benzocyclooctene-4-carboxylic acid (2-hydroxy-5-oxo-tetrahydro-furan-3-yl)-amide: $^1$H NMR (CD$_3$OD) δ 7.93 (d, J=8.4 Hz, 2H), 7.53 (d, J=8.4 Hz, 2H), 5.56 (m, 1H), 5.54 (m, 1H), 5.49 (m, 1H), 5.00–4.20 (m, 5H), 3.83 (br s, 2H), 3.65 (m, 1H), 3.20 (m, 1H), 2.90 (m, 1H), 2.80–2.40 (m, 4H); MS 478, 480 (M+H)+.

(4S,6S,10aS)-6-[(2-trifluoromethylbenzoyl)amino]-5-oxo-1,3,4,5,6,7,10,10a-octahydro-2-oxa-[4a]-aza-benzocyclooctene-4-carboxylic acid (2-hydroxy-5-oxo-tetrahydro-furan-3-yl)-amide: $^1$H NMR (CD$_3$OD) δ 7.81 (d, J=7.7 Hz, 1H), 7.72 (m, 3H), 5.73 (m, 2H), 5.42 (m, 1H), 4.78–4.24 (m, 5H), 3.82 (br s, 2H), 3.66 (dd, J=11.7, 4.5 Hz, 1H), 3.23 (m,1H), 2.88 (m,1H), 2.65 (m, 1H), 2.46 (m, 3H); MS 512 (M+H)+.

(4S,6S,10aS)-6-[(3-trifluoromethylbenzoyl)amino]-5-oxo-1,3,4,5,6,7,10,10a-octahydro-2-oxa-[4a]-aza-benzocyclooctene-4-carboxylic acid (2-hydroxy-5-oxo-tetrahydro-furan-3-yl)-amide: $^1$H NMR (CD$_3$OD) δ 8.26 (s, 1H), 8.20 (d, J=8.0 Hz, 1H), 7.91 (d, J7.5 Hz, 1H), 7.74 (dd, J=8.0, 7.5 Hz, 1H), 5.81 (m, 1H), 5.69 (m, 1H), 5.48 (m, 1H), 4.75–4.25 (m, 5H), 3.83 (br s, 2H), 3.68 (m, 1H), 3.23 (m, 1H), 2.88 (m, 1H), 2.67 (m, 1H), 2.50 (m, 3H); MS 512 (M+H)+.

(4S,6S,10aS)-6-[(4-trifluoromethylbenzoyl)amino]-5-oxo-1,3,4,5,6,7,10,10a-octahydro-2-oxa-[4a]-aza-benzocyclooctene-4-carboxylic acid (2-hydroxy-5-oxo-tetrahydro-furan-3-yl)-amide: $^1$H NMR (CD$_3$OD) δ 8.11 (d, J=8.0 Hz, 2H), 7.84 (d, J=8.0 Hz, 2H), 5.80 (m, 1H), 5.69 (m, 1H), 5.48 (m, 1H), 4.75–4.25 (m, 5H), 3.85 (br s, 2H), 3.67 (m, 1H), 3.23 (m, 1H), 2.90 (m, 1H), 2.67 (m, 1H), 2.52 (m, 3H); MS 512 (M+H)+.

(4S,6S,10aS)-6-[(Naphthalene-2-carbonyl)-amino]-5-oxo-1,3,4,5,6,7,10,10a-octahydro-2-oxa-4a-aza-benzocyclooctene-4-carboxylic acid (2-hydroxy-5-oxo-tetrahydro-furan-3-yl)-amide: $^1$H NMR (CD$_3$OD) δ 8.50 (s, 1H), 7.98 (m, 4H), 7.62 (m, 2H), 5.80 (m, 1H), 5.69 (m, 1H), 4.75 (d, J=2.1 Hz, 1H), 4.68 (m, 1H), 4.55 (m, 1H), 4.49 (d, J=6.15 Hz, 1H), 4.37 (m, 1H), 3.65 (dd, J=12, 4.5 Hz, 1H), 3.36–3.21 (m, 2H), 2.88 (m, 1H), 2.64 (m, 1H), 2.54 (m, 4H); MS 494 (M+H)+.

(4S,6S,10aS)-6-[(benzo[b]thiophene-2-carbonyl)-amino]-5-oxo-1,3,4,5,6,7,10,10a-octahydro-2-oxa-4a-aza-benzocyclooctene-4-carboxylic acid (2-hydroxy-5-oxo-tetrahydro-furan-3-yl)-amide: $^1$H NMR (CD$_3$OD) δ 8.13 (s, 1H), 7.96 (m, 2H), 7.48 (m, 2H), 5.77 (m, 1H), 5.70 (m, 1H), 5.45 (m, 1H), 4.74 (m, 1H), 4.66 (m, 1H), 4.51 (m, 2H), 4.36 (m, 1H), 3.83 (br s, 2H), 3.66 (br m, 1H), 3.23 (m, 1H), 2.89 (m, 1H), 2.68 (m, 1H), 2.50 (m, 3H); MS 500 (M+H)+.

(4S,6S,10aS)-6-{[3-(4-Chlorophenyl)-5-methyl-ioxazole-4-carbonyl]-amino}-5-oxo-1,3,4,5,6,7,10,10a-octahydro-2-oxa-4a-aza-benzocyclooctene-4-carboxylic acid (2-hydroxy-5-oxo-tetrahydro-furan-3-yl)-amide: $^1$H NMR (CD$_3$OD) δ 7.57 (m, 4H), 5.65 (br s, 2H), 5.21 (m, 1H), 4.61 (m, 2H), 4.42 (m, 3H), 3.77 (br s, 2H), 3.57 (dd, J=12.3, 4.2 Hz, 1H), 3.11 (m, 1H), 2.77 (s, 3H), 2.45–2.24 (m, 5H); MS 559 (M+H)+.

(4S,6S,10aS)-6-(3-Fluorobenzoylamino)-5-oxo-1,3,4,5,6,7,10,10a-octahydro-2-oxa-4a-aza-benzocyclooctene-4-carboxylic acid (2-hydroxy-5-oxo-tetrahydro-fuan-3-yl)-amide: $^1$H NMR (CD$_3$OD) δ 7.77–7.51 (m, 3H), 7.34 (m, 1H), 5.77 (m, 1H), 5.68 (m, 1H), 5.44 (m, 1H), 4.73 (m, 1H), 4.66 (m, 1H), 4.51 (m, 2H), 4.35 (m, 1H), 3.83 (br s, 2H), 3.65 (dd, J=12.3, 4.5 Hz, 1H), 3.21 (m, 1H), 2.87 (m, 1H), 2.67 (m, 1H), 2.52 (m, 3H).

(4S,6S,10aS)-6-(4-Fluorobenzoylamino)-5-oxo-1,3,4,5,6,7,10,10a-octahydro-2-oxa-4a-aza-benzocyclooctene-4-carboxylic acid (2-hydroxy-5-oxo-tetrahydro-fuan-3-yl)-amide: $^1$H NMR (CD$_3$OD) δ 7.99 (m, 2H), 7.25 (m, 2H), 5.77 (m, 1H), 5.68 (m, 1H), 5.43 (m, 1H), 4.73 (m, 1H), 4.66 (m, 1H), 4.51 (m, 2H), 4.35 (m, 1H), 3.65 (dd, J=12, 4.2 Hz, 1H), 3.23 (m, 2H), 2.87 (m, 1H), 2.67 (m, 1H), 2.49 (m, 4H); MS 462 (M+H)+.

(4S,6S,10aS)-5-Oxo-6-[(quinoxaline-2-carbonyl)-amino]-1,3,4,5,6,7,10,10a-octahydro-2-oxa-4a-aza-benzocyclooctene-4-carboxylic acid (2-hydroxy-5-oxo-tetrahydro-furan-3-yl-amide: $^1$H NMR (CD$_3$OD) δ 9.57 (s, 1H), 8.28 (m, 2H), 8.03 (m, 2H), 5.70–5.62 (m, 2H), 5.37 (m, 1H), 4.77 (m, 1H), 4.69 (m, 1H), 4.45–4.23 (m, 3H), 3.72 (br s, 2H), 3.66 (dd, J=11.7, 3.9 Hz, 1H), 2.85–2.33 (m, 6H).

(4S,6S,10aS)-6-benzoylamino-5-oxo-1,3,4,5,6,7,10,10a-octahydro-2-oxa-4a-aza-benzocyclooctene-4-carboxylic acid (2-hydroxy-5-oxo-tetrahydro-furan-3-yl)-amide: $^1$H NMR (CD$_3$OD) δ 7.93 (d, J=8.4 Hz, 2H), 7.60 (dd, J=6.9, 6.9 Hz, 1H), 7.52 (dd, J=7.5, 7.5 Hz, 2H), 5.90–5.60 (m, 2H), 5.43 (m, 1H), 4.73 (m, 1H), 4.66 (m, 1H), 4.51 (m, 2H), 4.35 (m, 1H), 3.83 (br s, 2H), 3.65 (m, 1H), 3.20 (m, 1H), 2.87 (m, 1H), 2.70–2.40 (m, 4H).

Category IV of the interleukin-1β converting enzyme inhibitors according to the present invention relates to compound comprising a 4,6-substituted octahydro-2-oxa [4a]aza-benzocyclocten-5-one scaffold having the formula:

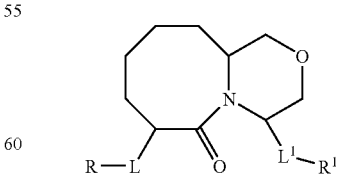

one iteration of the first aspect of this Category comprises scaffolds having the indicated stereochemistry. Table IV relates to non-limiting examples of analogs comprising a first aspect of this category, said analogs having the formula:

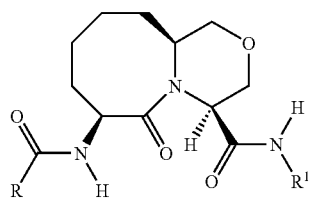

wherein R and R¹ are defined in Table IV herein below.

TABLE IV

| No. | R | R¹ |
|---|---|---|
| 313 | phenyl | 2-hydroxy-5-oxo-tetrahydrofuran-3-yl |
| 314 | phenyl | 2-ethoxy-5-oxo-tetrahydrofuran-3-yl |
| 315 | quinolin-2-yl | 2-hydroxy-5-oxo-tetrahydrofuran-3-yl |
| 316 | quinolin-2-yl | 2-ethoxy-5-oxo-tetrahydrofuran-3-yl |
| 317 | benzothiophen-2-yl | 2-hydroxy-5-oxo-tetrahydrofuran-3-yl |
| 318 | benzothiophen-2-yl | 2-ethoxy-5-oxo-tetrahydrofuran-3-yl |
| 319 | 2-thienyl | 2-hydroxy-5-oxo-tetrahydrofuran-3-yl |
| 320 | 2-thienyl | 2-ethoxy-5-oxo-tetrahydrofuran-3-yl |
| 321 | isoquinolin-1-yl | 2-hydroxy-5-oxo-tetrahydrofuran-3-yl |
| 322 | isoquinolin-1-yl | 2-ethoxy-5-oxo-tetrahydrofuran-3-yl |
| 323 | naphth-1-yl | 2-hydroxy-5-oxo-tetrahydrofuran-3-yl |
| 324 | naphth-1-yl | 2-ethoxy-5-oxo-tetrahydrofuran-3-yl |
| 325 | naphth-2-yl | 2-hydroxy-5-oxo-tetrahydrofuran-3-yl |
| 326 | naphth-2-yl | 2-ethoxy-5-oxo-tetrahydrofuran-3-yl |
| 327 | 2-chlorophenyl | 2-hydroxy-5-oxo-tetrahydrofuran-3-yl |
| 328 | 2-chlorophenyl | 2-ethoxy-5-oxo-tetrahydrofuran-3-yl |
| 329 | 3-chlorophenyl | 2-hydroxy-5-oxo-tetrahydrofuran-3-yl |
| 330 | 3-chlorophenyl | 2-ethoxy-5-oxo-tetrahydrofuran-3-yl |
| 331 | 4-chlorophenyl | 2-hydroxy-5-oxo-tetrahydrofuran-3-yl |
| 332 | 4-chlorophenyl | 2-ethoxy-5-oxo-tetrahydrofuran-3-yl |
| 333 | 2-fluorophenyl | 2-hydroxy-5-oxo-tetrahydrofuran-3-yl |
| 334 | 2-fluorophenyl | 2-ethoxy-5-oxo-tetrahydrofuran-3-yl |
| 335 | 3-fluorophenyl | 2-hydroxy-5-oxo-tetrahydrofuran-3-yl |
| 336 | 3-fluorophenyl | 2-ethoxy-5-oxo-tetrahydrofuran-3-yl |
| 337 | 4-fluorophenyl | 2-hydroxy-5-oxo-tetrahydrofuran-3-yl |
| 338 | 4-fluorophenyl | 2-ethoxy-5-oxo-tetrahydrofuran-3-yl |
| 339 | 3,4-difluorophenyl | 2-hydroxy-5-oxo-tetrahydrofuran-3-yl |
| 340 | 3,4-difluorophenyl | 2-ethoxy-5-oxo-tetrahydrofuran-3-yl |
| 341 | 4-fluorothienyl | 2-hydroxy-5-oxo-tetrahydrofuran-3-yl |
| 342 | 4-fluorothienyl | 2-ethoxy-5-oxo-tetrahydrofuran-3-yl |
| 343 | 2-aminopyrimidinyl | 2-hydroxy-5-oxo-tetrahydrofuran-3-yl |
| 344 | 2-aminopyrimidinyl | 2-ethoxy-5-oxo-tetrahydrofuran-3-yl |
| 345 | 2-phenylamino-4-pyrimidinyl | 2-hydroxy-5-oxo-tetrahydrofuran-3-yl |
| 346 | 2-phenylamino-4-pyrimidinyl | 2-ethoxy-5-oxo-tetrahydrofuran-3-yl |
| 347 | 2-phenoxy-4-pyrimidinyl | 2-hydroxy-5-oxo-tetrahydrofuran-3-yl |
| 348 | 2-phenoxy-4-pyrimidinyl | 2-ethoxy-5-oxo-tetrahydrofuran-3-yl |
| 349 | 2-benzoxy-4-pyrimidinyl | 2-hydroxy-5-oxo-tetrahydrofuran-3-yl |
| 350 | 2-benzoxy-4-pyrimidinyl | 2-ethoxy-5-oxo-tetrahydrofuran-3-yl |
| 351 | 2-methoxy-4-pyrimidinyl | 2-hydroxy-5-oxo-tetrahydrofuran-3-yl |
| 352 | 2-methoxy-4-pyrimidinyl | 2-ethoxy-5-oxo-tetrahydrofuran-3-yl |
| 353 | isoquinolin-3-yl | 2-hydroxy-5-oxo-tetrahydrofuran-3-yl |
| 354 | isoquinolin-3-yl | 2-ethoxy-5-oxo-tetrahydrofuran-3-yl |
| 355 | 2-phenylamino-4-pyridinyl | 2-hydroxy-5-oxo-tetrahydrofuran-3-yl |
| 356 | 2-phenylamino-4-pyridinyl | 2-ethoxy-5-oxo-tetrahydrofuran-3-yl |
| 357 | 2-phenoxy-4-pyridinyl | 2-hydroxy-5-oxo-tetrahydrofuran-3-yl |
| 358 | 2-phenoxy-4-pyridinyl | 2-ethoxy-5-oxo-tetrahydrofuran-3-yl |
| 359 | 2-benzoxy-4-pyridinyl | 2-hydroxy-5-oxo-tetrahydrofuran-3-yl |
| 360 | 2-benzoxy-4-pyridinyl | 2-ethoxy-5-oxo-tetrahydrofuran-3-yl |
| 361 | 2-methoxy-4-pyridinyl | 2-hydroxy-5-oxo-tetrahydrofuran-3-yl |
| 362 | 2-methoxy-4-pyridinyl | 2-ethoxy-5-oxo-tetrahydrofuran-3-yl |
| 363 | 4-hydroxyphenyl | 2-hydroxy-5-oxo-tetrahydrofuran-3-yl |
| 364 | 4-hydroxyphenyl | 2-ethoxy-5-oxo-tetrahydrofuran-3-yl |
| 365 | 2-methylphenyl | 2-hydroxy-5-oxo-tetrahydrofuran-3-yl |
| 366 | 2-methylphenyl | 2-ethoxy-5-oxo-tetrahydrofuran-3-yl |
| 367 | 3-methylphenyl | 2-hydroxy-5-oxo-tetrahydrofuran-3-yl |
| 368 | 3-methylphenyl | 2-ethoxy-5-oxo-tetrahydrofuran-3-yl |
| 369 | 4-methylphenyl | 2-hydroxy-5-oxo-tetrahydrofuran-3-yl |
| 370 | 4-methylphenyl | 2-ethoxy-5-oxo-tetrahydrofuran-3-yl |
| 371 | 2-trifluoromethylphenyl | 2-hydroxy-5-oxo-tetrahydrofuran-3-yl |
| 372 | 2-trifluoromethylphenyl | 2-ethoxy-5-oxo-tetrahydrofuran-3-yl |
| 373 | 3-trifluoromethylphenyl | 2-hydroxy-5-oxo-tetrahydrofuran-3-yl |
| 374 | 3-trifluoromethylphenyl | 2-ethoxy-5-oxo-tetrahydrofuran-3-yl |
| 375 | 4-trifluoromethylphenyl | 2-hydroxy-5-oxo-tetrahydrofuran-3-yl |
| 376 | 4-trifluoromethylphenyl | 2-ethoxy-5-oxo-tetrahydrofuran-3-yl |
| 377 | phenylamino | 2-hydroxy-5-oxo-tetrahydrofuran-3-yl |
| 378 | phenylamino | 2-ethoxy-5-oxo-tetrahydrofuran-3-yl |
| 379 | 2-methoxyphenyl | 2-hydroxy-5-oxo-tetrahydrofuran-3-yl |
| 380 | 2-methoxyphenyl | 2-ethoxy-5-oxo-tetrahydrofuran-3-yl |
| 381 | 3-methoxyphenyl | 2-hydroxy-5-oxo-tetrahydrofuran-3-yl |
| 382 | 3-methoxyphenyl | 2-ethoxy-5-oxo-tetrahydrofuran-3-yl |
| 383 | 4-methoxyphenyl | 2-hydroxy-5-oxo-tetrahydrofuran-3-yl |
| 384 | 4-methoxyphenyl | 2-ethoxy-5-oxo-tetrahydrofuran-3-yl |
| 385 | 2-methoxypyrimidin-4-yl | 2-hydroxy-5-oxo-tetrahydrofuran-3-yl |
| 386 | 2-methoxypyrimidin-4-yl | 2-ethoxy-5-oxo-tetrahydrofuran-3-yl |
| 387 | 2-phenoxypyrimidin-4-yl | 2-hydroxy-5-oxo-tetrahydrofuran-3-yl |
| 388 | 2-phenoxypyrimidin-4-yl | 2-ethoxy-5-oxo-tetrahydrofuran-3-yl |
| 389 | 2-benzyloxypyrimidin-4-yl | 2-hydroxy-5-oxo-tetrahydrofuran-3-yl |
| 390 | 2-benzyloxypyrimidin-4-yl | 2-ethoxy-5-oxo-tetrahydrofuran-3-yl |
| 391 | 2-(piperidin-2-yl)pyrimidin-4-yl | 2-hydroxy-5-oxo-tetrahydrofuran-3-yl |
| 392 | 2-(piperidin-2-yl)pyrimidin-4-yl | 2-ethoxy-5-oxo-tetrahydrofuran-3-yl |
| 393 | 2-(2-fluorophenylamino)pyrimidin-4-yl | 2-hydroxy-5-oxo-tetrahydrofuran-3-yl |
| 394 | 2-(2-fluorophenylamino)pyrimidin-4-yl | 2-ethoxy-5-oxo-tetrahydrofuran-3-yl |
| 395 | 2-(benzylamino)pyrimidin-4-yl | 2-hydroxy-5-oxo-tetrahydrofuran-3-yl |
| 396 | 2-(benzylamino)pyrimidin-4-yl | 2-ethoxy-5-oxo-tetrahydrofuran-3-yl |

The compounds comprising Category IV of the present invention can be suitably prepared under most circumstances from the corresponding Category III compounds by direct reduction of the 8-member ring double bond, for example, the conversion of compound 33 to 34 as depicted herein below in scheme XIII.

Scheme XIII

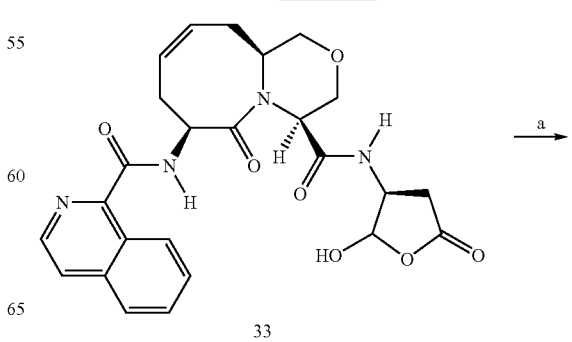

33

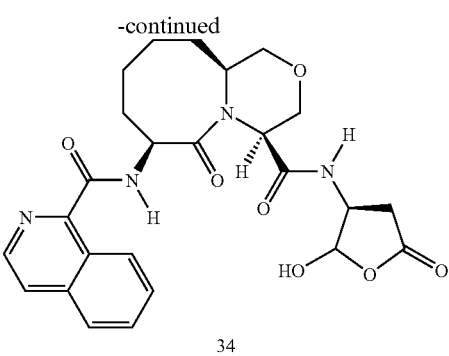

34

Reagents and conditions: a) H₂, Pd/C, EtOAc.

EXAMPLE 9

Preparation of (4S,6S,10aS)-6-[(isoquinoline-1-carbonyl)-amino]-5-oxo-decahydro-2-oxa-4a-azabenzocyclooctene-4-carboxylic acid (2-hydroxy-5-oxo-tetrahydro-furan-3-yl)-amide (34):

(4S,6S,10aS)-6-[(isoquinoline-1-carbonyl)amino]-5-oxo-1,3,4,5,6,7,10,10a-octahydro-2-oxa-[4a]-aza-benzocyclooctene-4-carboxylic acid (2-hydroxy-5-oxo-tetrahydro-furan-3-yl)-amide, 33, is dissolved in MeOH and treated with a catalytic amount of Pd/C. The resulting suspension is stirred at room temperature under a H₂ atmosphere for 2 hours. The solution is filtered to remove the catalyst and concentrated in vacuo to afford the desired product. 1H NMR (CD₃OD) δ 9.16 (d, J=8.4 Hz, 1H), 8.56 (d, J=5.7 Hz, 1H), 8.00 (m, 2H), 7.80 (m, 2H), 5.21 (d, J=9.0 Hz, 1H), 4.90 (m, 1H), 4.71 (m, 1H), 4.45 (m, 1H), 4.29 (m, 2H), 3.86 (m, 2H), 3.69 (m, 1H), 2.90–1.20 (series of m, 11H); MS 497 (M+H)+.

The following are non-limiting examples of this iteration of the first aspect of Category IV analogs according to the present invention.

6-[(Naphthalene-2-carbonyl)-amino]-5-oxo-decahydro-2-oxa-4a-aza-benzocyclooctene-4-carboxylic acid (2-hydroxy-5-oxo-tetrahydro-furan-3-yl)-amide: ¹H NMR (CD₃OD) δ 8.48 (s, 1H), 8.03 (m, 1H), 7.96 (m, 2H), 7.63 (m, 3H), 5.04 (dd, J=11.7, 2.4 Hz, 1H), 4.70 (m, 1H), 4.57 (m, 1H), 4.33–4.14 (br m, 3H), 3.87 (m, 2H), 3.67 (m, 1H), 2.90–1.20 (series of m, 10H); MS 496 (M+H)⁺.

6-[(benzo[b]thiophene-2-carbonyl)-amino]-5-oxo-decahydro-2-oxa-4a-aza-benzocyclooctene-4-carboxylic acid (2-hydroxy-5-oxo-tetrahydro-furan-3-yl)-amide: ¹H NMR (CD₃OD) δ 8.66 (br s, 1H), 8.10 (s, 1H), 7.94 (m, 2H), 7.47 (m, 2H), 5.52 (br s, 1H), 5.09 (m, 1H), 4.80 (br s, 1H), 4.71 (br s, 1H), 4.46–4.19 (m, 4H), 3.83 (m, 3H), 3.66 (m, 1H), 2.8–1.2 (series of m, 8H); MS 502 (M+H)⁺.

6-[(2-Methoxy-pyrimidine-4-carbonyl)-amino]-5-oxo-decahydro-2-oxa-4a-aza-benzocyclooctene-4-carboxylic acid (2-hydroxy-5-oxo-tetrahydro-furan-3-yl)-amide: ¹H NMR (CD₃OD) δ 9.09 (d, J=4.9 Hz, 1H), 8.83 (d, J=4.9 Hz, 1H), 5.12 (m, 1H), 4.83 (d, J=4.4Hz, 1H), 4.72 (d, J=4.0Hz, 1H), 4.44 (d, J=12.4 Hz, 1H), 4.33 (m, 1H), 4.19 (br d, J=12.4 Hz, 1H), 4.14 (s, 3H), 3.83 (br s, 2H), 3.64 (dd, J=12.4, 4.6 Hz, 1H), 2.61 (m, 1H), 2.38 (m, 1H), 2.20 (m, 1H), 2.22–1.68 (m, 3H), 1.64–1.40 (m, 2H), 1.27 (m, 1H); HRMS 478.195687 (M+H). 5-Oxo-6-[(2-phenoxy-pyrimidine-4-carbonyl)-amino]-decahydro-2-oxa-4a-aza-benzocyclooctene-4-carboxylic acid (2-hydroxy-5-oxo-tetrahydro-furan-3-yl)-amide: ¹H NMR (CD₃OD) δ 8.83 (d, J=4.7 Hz, 1H), 7.79 (d, J=4.7 Hz, 1H), 7.52 (dd, J=8.4, 7.5 Hz, 2H), 7.34 (t, J=7.5 Hz, 1H), 7.28 (d, J=8.4 Hz, 2H), 5.06 (dd, J=11.2, 2.8 Hz, 1H), 4.79 (d, J=3.6 Hz, 1H), 4.73 (d, J=3.7 Hz, 1H), 4.43 (d, J=12.4 Hz, 1H), 4.35 (m, 1H), 4.16 (br d, J=12.4 Hz, 1H), 3.81 (br s, 2H), 3.62 (dd, J=12.0, 4.4 Hz, 1H), 2.61 (m, 2H), 2.36 (m, 1H), 2.15 (m, 1H), 2.04–1.78 (m, 2H), 1.76–1.38 (m, 3H), 1.22 (m, 1H); HRMS 540.211897 (M+H)

6-[(2-benzyloxy-pyrimidine-4-carbonyl)-amino]-5-oxo-decahydro-2-oxa-4a-aza-benzocyclooctene-4-carboxylic acid (2-hydroxy-5-oxo-tetrahydro-furan-3-yl)-amide: ¹H NMR (CD₃OD) δ 8.83 (d, J=4.8 Hz, 1H), 7.70 (d, J=4.8 Hz, 1H), 7.61 (d, J=7.0 Hz, 2H), 7.44 (dd, J=7.3, 7.0 Hz, 2H), 7.38 (t, J=7.3 Hz, 1H), 5.58 (s, 2H), 5.11 (dd, J=11.8, 2.9 Hz, 1H), 4.88 (m, 1H), 4.73 (d, J=4.0 Hz, 1H), 4.45 (d, J=12.0 Hz, 1H), 4.35 (m, 1H), 4.19 (br d, J=12.8 Hz, 1H), 3.83 (s, 2H), 3.64 (dd, J=12.0, 4.4 Hz, 1H), 2.62 (m, 2H), 2.38 (m, 1H), 2.18 (m, 1H), 2.10–1.70 (m, 3H), 1.65–1.40 (m, 2H), 1.30 (m, 1H); HRMS 554.226590 (M+H)

5-Oxo-6-[(2-piperidin-1-yl-pyrimidine-4-carbonyl)-amino]-decahydro-2-oxa-4a-aza-benzocyclooctene-4-carboxylic acid (2-hydroxy-5-oxo-tetrahydro-furan-3-yl)-amide: ¹H NMR (CD₃OD) δ 9.06 (d, J=4.8 Hz, 1H), 8.54 (d, J=4.8 Hz, 1H), 5.08 (dd, J=11.4, 2.9 Hz, 1H), 4.84 (d, J=4.4 Hz, 1H), 4.72 (d, J=4.4 Hz, 1H), 4.44 (d, J=12.0 Hz, 1H), 4.34 (m, 1H), 4.18 (br d, J=12.4 Hz, 1H), 3.90 (m, 4H), 3.82 (s, 2H), 3.63 (dd, J=12.4, 4.4 Hz,1H), 2.62 (m, 2H), 2.38 (m,1H), 2.20 (m, 1H), 2.04–1.40 (m, 12H), 1.27 (m, 1H); HRMS 531.255732 (M+H)

6-{[2-(2-Fluoro-phenylamino)-pyrimidine-4-carbonyl]-amino}-5-oxo-decahydro-2-oxa-4a-aza-benzocyclooctene-4-carboxylic acid (2-hydroxy-5-oxo-tetrahydro-furan-3-yl)-amide:

¹H NMR (CD₃OD) δ 8.68 (d, J=4.8 Hz, 1H), 8.16 (ddd, J=8.0, 8.0,1.4 Hz, 1H), 7.44 (d, J=4.8 Hz, 1H), 7.36–7.12 (m, 3H), 5.09 (dd, J=11.7, 2.9 Hz, 1H), 4.85 (d, J=4.8 Hz,1H), 4.75 (d, J=3.7 Hz,1H), 4.44 (d, J=12.4 Hz, 1H), 4.38 (m, 1H), 4.17 (br d, J=12.8 Hz, 1H), 3.82 (s, 2H), 3.63 (dd, J=12.1, 4.4 Hz, 1H), 2.62 (m, 2H), 2.38 (m, 1H), 2.19 (m,1H), 2.06–1.40 (m, 5H), 1.24 (m, 1H); HRMS 557.217828 (M+H)

6-[(2-benzylamino-pyrimidine-4-carbonyl)-amino]-5-oxo-decahydro-2-oxa-4a-aza-benzocyclooctene-4-carboxylic acid (2-hydroxy-5-oxo-tetrahydro-furan-3-yl)-amide: ¹H NMR (CD₃OD) δ 8.49 (d, J=4.8 Hz,1H), 7.48 (m, 2H), 7.36 (dd, J=7.7, 7.3 Hz, 1H), 7.25 (t, J=7.7 Hz, 1H), 7.19 (d, J=4.8 Hz, 1H), 5.07 (dd, J=11.5, 2.8 Hz, 1H), 4.89 (m, 1H), 4.73 (d, J=3.7 Hz, 1H), 4.64 (s, 2H), 4.45 (d, J=12.1, 1H), 4.36 (m, 1H), 4.17 (br d, J=12.4 Hz, 1H), 3.81 (s, 2H), 3.62 (dd, J=12.1, 4.4 Hz, 1H), 2.62 (m, 2H), 2.37 (m, 1H), 2.12 (m, 1H), 2.05–1.63 (m, 3H), 1.62–1.40 (m, 2H), 1.25 (m, 1H); HRMS 553.242760 (M+H)

Category V of the interleukin-1β converting enzyme inhibitors according to the present invention relates to compound comprising a 4,7-disubstituted 1,2,3,4,7,8,11,11a-octahydro-pyrido[1,2-a]azocin-6-one scaffold having the formula:

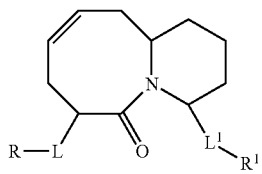

one iteration of the first aspect of this Category comprises scaffolds having the indicated stereochemistry. Table V relates to non-limiting examples of analogs comprising a first aspect of this category, said analogs having the formula:

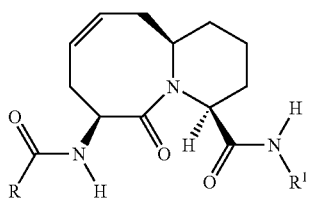

wherein R and R¹ are defined in Table V herein below.

TABLE V

| No. | R | R¹ |
|---|---|---|
| 397 | phenyl | 2-hydroxy-5-oxo-tetrahydrofuran-3-yl |
| 398 | phenyl | 2-ethoxy-5-oxo-tetrahydrofuran-3-yl |
| 399 | quinolin-2-yl | 2-hydroxy-5-oxo-tetrahydrofuran-3-yl |
| 400 | quinolin-2-yl | 2-ethoxy-5-oxo-tetrahydrofuran-3-yl |
| 401 | benzothiophen-2-yl | 2-hydroxy-5-oxo-tetrahydrofuran-3-yl |
| 402 | benzothiophen-2-yl | 2-ethoxy-5-oxo-tetrahydrofuran-3-yl |
| 403 | 2-thienyl | 2-hydroxy-5-oxo-tetrahydrofuran-3-yl |
| 404 | 2-thienyl | 2-ethoxy-5-oxo-tetrahydrofuran-3-yl |
| 405 | isoquinolin-1-yl | 2-hydroxy-5-oxo-tetrahydrofuran-3-yl |
| 406 | isoquinolin-1-yl | 2-ethoxy-5-oxo-tetrahydrofuran-3-yl |
| 407 | naphth-1-yl | 2-hydroxy-5-oxo-tetrahydrofuran-3-yl |
| 408 | naphth-1-yl | 2-ethoxy-5-oxo-tetrahydrofuran-3-yl |
| 409 | naphth-2-yl | 2-hydroxy-5-oxo-tetrahydrofuran-3-yl |
| 410 | naphth-2-yl | 2-ethoxy-5-oxo-tetrahydrofuran-3-yl |
| 411 | 2-chlorophenyl | 2-hydroxy-5-oxo-tetrahydrofuran-3-yl |
| 412 | 2-chlorophenyl | 2-ethoxy-5-oxo-tetrahydrofuran-3-yl |
| 413 | 3-chlorophenyl | 2-hydroxy-5-oxo-tetrahydrofuran-3-yl |
| 414 | 3-chlorophenyl | 2-ethoxy-5-oxo-tetrahydrofuran-3-yl |
| 415 | 4-chlorophenyl | 2-hydroxy-5-oxo-tetrahydrofuran-3-yl |
| 416 | 4-chlorophenyl | 2-ethoxy-5-oxo-tetrahydrofuran-3-yl |
| 417 | 2-fluorophenyl | 2-hydroxy-5-oxo-tetrahydrofuran-3-yl |
| 418 | 2-fluorophenyl | 2-ethoxy-5-oxo-tetrahydrofuran-3-yl |
| 419 | 3-fluorophenyl | 2-hydroxy-5-oxo-tetrahydrofuran-3-yl |
| 42 | 3-fluorophenyl | 2-ethoxy-5-oxo-tetrahydrofuran-3-yl |
| 421 | 4-fluorophenyl | 2-hydroxy-5-oxo-tetrahydrofuran-3-yl |
| 422 | 4-fluorophenyl | 2-ethoxy-5-oxo-tetrahydrofuran-3-yl |
| 423 | 3,4-difluorophenyl | 2-hydroxy-5-oxo-tetrahydrofuran-3-yl |
| 424 | 3,4-difluorophenyl | 2-ethoxy-5-oxo-tetrahydrofuran-3-yl |
| 425 | 4-fluorothienyl | 2-hydroxy-5-oxo-tetrahydrofuran-3-yl |
| 426 | 4-fluorothienyl | 2-ethoxy-5-oxo-tetrahydrofuran-3-yl |
| 427 | 2-aminopyrimidinyl | 2-hydroxy-5-oxo-tetrahydrofuran-3-yl |
| 428 | 2-aminopyrimidinyl | 2-ethoxy-5-oxo-tetrahydrofuran-3-yl |
| 429 | 2-phenylamino-4-pyrimidinyl | 2-hydroxy-5-oxo-tetrahydrofuran-3-yl |
| 430 | 2-phenylamino-4-pyrimidinyl | 2-ethoxy-5-oxo-tetrahydrofuran-3-yl |
| 431 | 2-phenoxy-4-pyrimidinyl | 2-hydroxy-5-oxo-tetrahydrofuran-3-yl |
| 432 | 2-phenoxy-4-pyrimidinyl | 2-ethoxy-5-oxo-tetrahydrofuran-3-yl |
| 433 | 2-benzoxy-4-pyrimidinyl | 2-hydroxy-5-oxo-tetrahydrofuran-3-yl |
| 434 | 2-benzoxy-4-pyrimidinyl | 2-ethoxy-5-oxo-tetrahydrofuran-3-yl |

TABLE V-continued

| No. | R | R¹ |
|---|---|---|
| 435 | 2-methoxy-4-pyrimidinyl | 2-hydroxy-5-oxo-tetrahydrofuran-3-yl |
| 436 | 2-methoxy-4-pyrimidinyl | 2-ethoxy-5-oxo-tetrahydrofuran-3-yl |
| 437 | isoquinolin-3-yl | 2-hydroxy-5-oxo-tetrahydrofuran-3-yl |
| 438 | isoquinolin-3-yl | 2-ethoxy-5-oxo-tetrahydrofuran-3-yl |
| 439 | 2-phenylamino-4-pyridinyl | 2-hydroxy-5-oxo-tetrahydrofuran-3-yl |
| 440 | 2-phenylamino-4-pyridinyl | 2-ethoxy-5-oxo-tetrahydrofuran-3-yl |
| 441 | 2-phenoxy-4-pyridinyl | 2-hydroxy-5-oxo-tetrahydrofuran-3-yl |
| 442 | 2-phenoxy-4-pyridinyl | 2-ethoxy-5-oxo-tetrahydrofuran-3-yl |
| 443 | 2-benzoxy-4-pyridinyl | 2-hydroxy-5-oxo-tetrahydrofuran-3-yl |
| 444 | 2-benzoxy-4-pyridinyl | 2-ethoxy-5-oxo-tetrahydrofuran-3-yl |
| 445 | 2-methoxy-4-pyridinyl | 2-hydroxy-5-oxo-tetrahydrofuran-3-yl |
| 446 | 2-methoxy-4-pyridinyl | 2-ethoxy-5-oxo-tetrahydrofuran-3-yl |
| 447 | 4-hydroxyphenyl | 2-hydroxy-5-oxo-tetrahydrofuran-3-yl |
| 448 | 4-hydroxyphenyl | 2-ethoxy-5-oxo-tetrahydrofuran-3-yl |
| 449 | 2-methylphenyl | 2-hydroxy-5-oxo-tetrahydrofuran-3-yl |
| 450 | 2-methylphenyl | 2-ethoxy-5-oxo-tetrahydrofuran-3-yl |
| 451 | 3-methylphenyl | 2-hydroxy-5-oxo-tetrahydrofuran-3-yl |
| 452 | 3-methylphenyl | 2-ethoxy-5-oxo-tetrahydrofuran-3-yl |
| 453 | 4-methylphenyl | 2-hydroxy-5-oxo-tetrahydrofuran-3-yl |
| 454 | 4-methylphenyl | 2-ethoxy-5-oxo-tetrahydrofuran-3-yl |
| 455 | 2-trifluoromethylphenyl | 2-hydroxy-5-oxo-tetrahydrofuran-3-yl |
| 456 | 2-trifluoromethylphenyl | 2-ethoxy-5-oxo-tetrahydrofuran-3-yl |
| 457 | 3-trifluoromethylphenyl | 2-hydroxy-5-oxo-tetrahydrofuran-3-yl |
| 58 | 3-trifluoromethylphenyl | 2-ethoxy-5-oxo-tetrahydrofuran-3-yl |
| 459 | 4-trifluoromethylphenyl | 2-hydroxy-5-oxo-tetrahydrofuran-3-yl |
| 460 | 4-trifluoromethylphenyl | 2-ethoxy-5-oxo-tetrahydrofuran-3-yl |
| 461 | phenylamino | 2-hydroxy-5-oxo-tetrahydrofuran-3-yl |
| 462 | phenylamino | 2-ethoxy-5-oxo-tetrahydrofuran-3-yl |
| 463 | 2-methoxyphenyl | 2-hydroxy-5-oxo-tetrahydrofuran-3-yl |
| 464 | 2-methoxyphenyl | 2-ethoxy-5-oxo-tetrahydrofuran-3-yl |
| 465 | 3-methoxyphenyl | 2-hydroxy-5-oxo-tetrahydrofuran-3-yl |
| 466 | 3-methoxyphenyl | 2-ethoxy-5-oxo-tetrahydrofuran-3-yl |
| 467 | 4-methoxyphenyl | 2-hydroxy-5-oxo-tetrahydrofuran-3-yl |
| 468 | 4-methoxyphenyl | 2-ethoxy-5-oxo-tetrahydrofuran-3-yl |

The compounds of Category V can be suitably prepared by the procedure outlined herein below, utilizing intermediate 42 which can be synthesized by the procedure described in Scheme XIV.

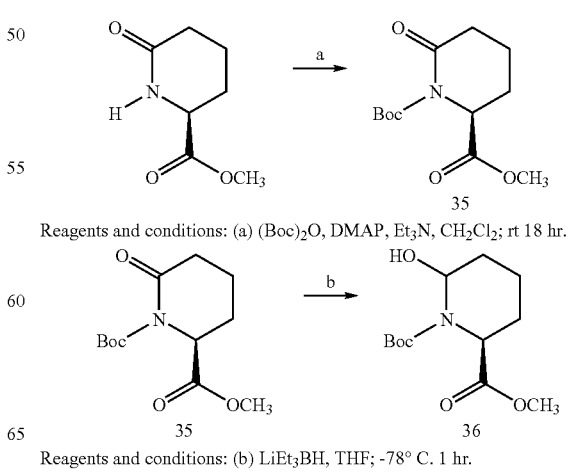

Scheme XIV

Reagents and conditions: (a) (Boc)₂O, DMAP, Et₃N, CH₂Cl₂; rt 18 hr.

Reagents and conditions: (b) LiEt₃BH, THF; -78° C. 1 hr.

-continued

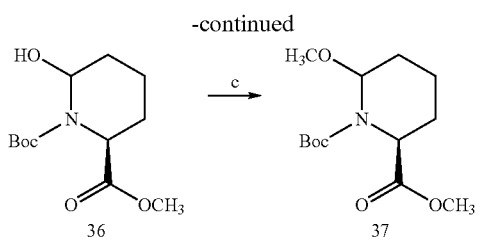

Reagents and conditions: (c) Dowex-50, MeOH; rt 3 hr..

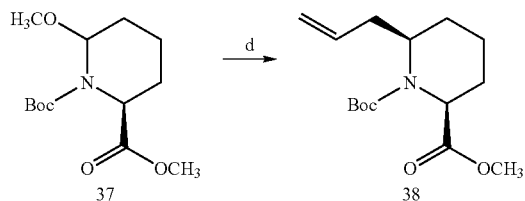

Reagents and conditions: (d) Allyl—TMS, BF3Et2O, CH2Cl2; -78° C. 1 hr.

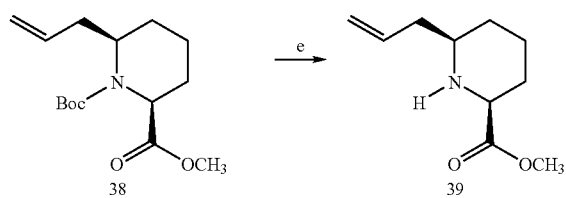

Reagents and conditions: (e) SOCl2, MeOH, rt 18 hr.

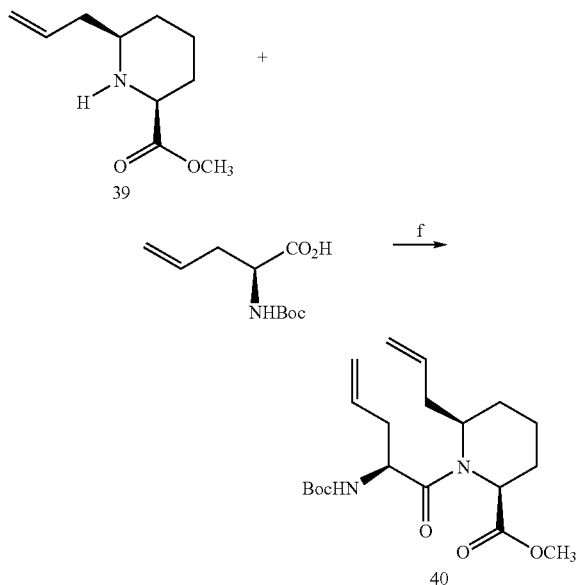

Reagents and conditions: (f) IIDQ, THF; rt 18 hr.

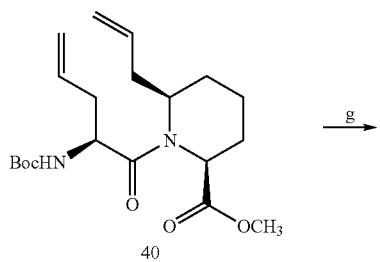

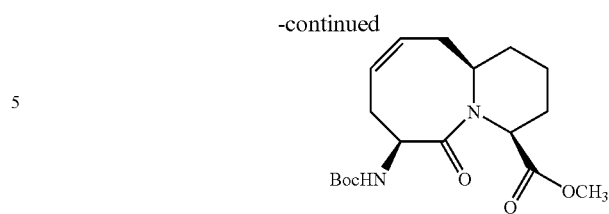

Reagents and conditions: (g) Grubbs' catalyst, CH2Cl2; reflux 24 hr.

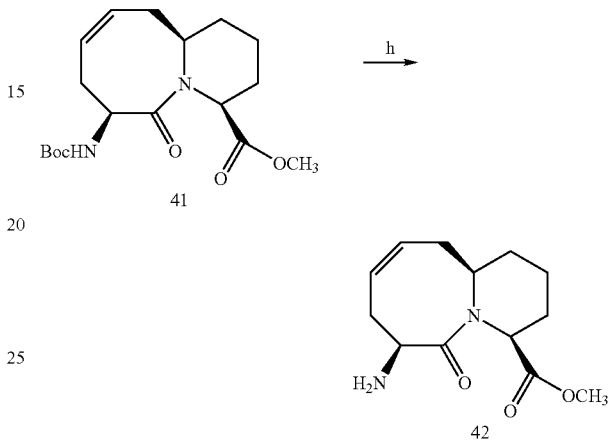

Reagents and conditions: (h) TFA, CH2Cl2; rt 2 hr.

Preparation of 6-oxo-piperidine-1,2-dicarboxylic acid 1-tert-butyl ester 2-methyl ester (35): To a solution of 6-oxo-piperidine-2-carboxylic acid methyl ester (3.58 g, 22.8 mmol), 4-dimethylaminopyridine (0.60 g, 4.9 mmol), and triethylamine (4.2 mL, 30 mmol) in CH$_2$Cl$_2$ (100 mL), di-t-butyldicarbonate (6.2 mL, 27 mmol) is added. After the consumption of the starting material, the reaction is diluted with EtOAc, washed with H$_2$O (2×100 mL) and brine (1×100 mL), dried over MgSO$_4$, filtered, and concentrated in vacuo to yield 5.16 g of crude product that is used in the next step without further purification. $^1$H NMR (CDCl$_3$) δ 4.75 (dd, J=5.8, 4.0 Hz, 1H), 3.81 (s, 3H), 2.69–2.46 (m, 2H), 2.26–2.40 (m, 2H), 1.86–1.74 (m, 2H), 1.54 (s, 9H).

Preparation of 6-hydroxy-piperidine-1,2-dicarboxylic acid 1-tert-butyl ester 2-methyl ester (36): To a solution of 6-oxo-piperidine-1,2-dicarboxylic acid 1-tert-butyl ester 2-methyl ester, 35, (5.1 g, 19.8 mmol) in THF (100 mL) at −78° C., a 1M solution of LiEt$_3$BH in THF (22.0 mL, 22 mmol) is added. After stirring for 1 hr at −78° C., the solution is cautiously quenched aqueous NH$_4$Cl. The crude product is extracted with EtOAc and the combined EtOAc extracts are washed with brine, dried (MgSO$_4$), and concentrated in vacuo. The desired product is used without further purification.

Preparation of 6-methoxy-piperidine-1,2-dicarboxylic acid 1-tert-butyl ester 2-methyl ester (37): The crude 6-hydroxy-piperidine-1,2-dicarboxylic acid 1-tert-butyl ester 2-methyl ester, 36, obtained in the previous step is dissolved in methanol (500 mL) and treated with Dowex-50 (1.0 g). After stirring at rt for 3 hr, the solution is filtered and concentrated in vacuo, and the residue is purified over silica (hexanes/ethyl acetate, 5:1) to afford 2.1 g of the desired product. $^1$H NMR (CDCl$_3$) δ 5.43 (br s, 0.5H), 5.28 (br s, 0.5H), 4.88 (br s, 0.5H), 4.66 (br s, 0.5H), 3.73 (s, 3H), 3.33 (s, 3H), 2.32 (m, 1H), 1.87 (m, 2H), 1.70–1.40 (m, 3H), 1.51 (s, 9H).

Preparation of 6-allyl-piperidine-1,2-dicarboxylic acid 1-tert-butyl ester 2-methyl ester (38): To a solution of 6-methoxy-piperidine-1,2-dicarboxylic acid 1-tert-butyl ester 2-methyl ester, 37, (5.0 g, 18.3 mmol) and allyltrimethylsilane (5.8 mL, 36.6 mmol) in CH$_2$Cl$_2$ (125 mL) at −78° C. is added dropwise boron trifluoride etherate (2.5 mL, 19.7 mmol). After 1 h, the solution is poured into water and extracted with EtOAc. The extracts are washed with brine, dried (MgSO$_4$), and concentrated in vacuo. The resulting residue is used in the next step without purification.

Preparation of 6-allyl-piperidine-2-carboxylic acid methyl ester (39): The crude 6-allyl-piperidine-1,2-dicarboxylic acid 1-tert-butyl ester 2-methyl ester obtained from the previous step is dissolved in MeOH (500 mL) and treated with thionyl chloride (20 mL). The solution is stirred overnight and the solvent removed in vacuo. The crude residue is dissolved in EtOAc, washed with saturated NaHCO$_3$, dried (MgSO$_4$), and concentrated to yield 2.1 g of the desired product. The product is used in the next step without purification. $^1$H NMR (CDCl$_3$) δ 5.82 (m, 1H), 5.22–5.10 (m, 2H), 3.75 (s, 3H), 3.37 (dd, J=11.1, 2.8 Hz, 1H), 2.60 (m, 1H), 2.21 (m, 2H), 2.10–1.10 (m, 6H).

Preparation of 6-allyl-1-(2-tert-butoxycarbonylamino-pent-4-enoyl)-piperidine-2-carboxylic acid methyl ester (40): A solution of 6-allyl-piperidine-2-carboxylic acid methyl ester, 39, (2.1 g, 11.5 mmol), 2-tert-butoxycarbonylamino-pent-4-enoic acid (9.9 g, 46 mmol), and IIDQ (13.9 g, 46 mmol) in THF (50 mL) is stirred at rt for 24 h. The reaction is diluted with EtOAc and washed with 1N HCl, saturated NaHCO$_3$, and brine. The solution is then dried (MgSO$_4$), concentrated, and purified by flash chromatography over silica (hexanes/ethyl acetate) to afford 1.1 g of the desired product. $^1$H NMR (CDCl$_3$) δ 5.76 (m, 2H), 5.60–4.20 (series of m, 8H), 3.71 (s, 3H), 2.60–1.50 (series of m, 10H), 1.44 (s, 9H).

Preparation of (4S,7S,11aR)-7-tert-butoxycarbonylamino-6-oxo-1,3,4,6,7,8,11,11a-octahydro-2H-pyrido[1,2-a]azocine-4-carboxylic acid methyl ester (41): 6-Allyl-1-(2-tert-butoxycarbonylamino-pent-4-enoyl)-piperidine-2-carboxylic acid methyl ester, 40, (1.0 g, 2.6 mmol) is dissolved in dichloromethane (100 mL). Grubbs catalyst (0.5 g, 0.61 mmol) is added and the mixture is heated at reflux for 24 hours. The reaction is cooled and dimethylsulfoxide (2 mL) is added. After 24 hours, the solution is concentrated to a oil, which is purified over silica (ethyl acetate/hexanes) to afford 680 mg of the desired product. $^1$H NMR (CDCl$_3$) δ 6.02 (d, J=6.6 Hz,1H), 5.61 (m, 1H), 5.21 (m, 1H), 4.93 (ddd, J=6.6, 6.2, 6.2 Hz, 1H), 4.54 (m, 1H), 3.71 (s, 3H), 2.95 (ddd, J=16.2, 5.9, 5.9 Hz, 1H), 2.63 (ddd, J=17.6, 12.0, 5.5 Hz,1H), 2.42 (ddd, J=16.2, 5.8, 5.1 Hz, 1H), 2.34–2.16 (m, 2H), 1.90–1.58 (m, 5H), 1.48 (s, 9H); $^{13}$C NMR δ 173.0, 172.5, 155.6, 129.2, 125.0, 79.9, 52.4, 52.0, 51.2, 50.8, 36.6, 34.5, 30.1, 28.8(3C), 26.4, 16.0.

Preparation of (4S,7S,11aR)-7-amino-6-oxo-1,3,4,6,7,8,11,11a-octahydro-2H-pyrido[1,2-a]azocine-4-carboxylic acid methyl ester (42): 7-tert-butoxycarbonyl-amino-6-oxo-1,3,4,6,7,8,11,11a-octahydro-2H-pyrido[1,2-a]azocine-4-carboxylic acid methyl ester , 41, (0.40 g, 1.1 mmol) is treated with a solution of 1:2 trifluoroacetic acid/CH$_2$Cl$_2$ (100 mL) and allowed to stir for 2 hours at room temperature after which the solution is concentrated in vacuo. The crude residue is redissolved in EtOAc, washed with saturated NaHCO$_3$, dried (MgSO$_4$), and concentrated. The resulting residue is used in the next step without purification. $^1$H NMR (CDCl$_3$) δ 5.68 (br s, 2H), 5.08 (br s, 1H), 4.76 (m, 1H), 4.45 (m, 1H), 3.71 (s, 3H), 3.12 (m, 1H), 2.68–2.42 (m, 2H), 2.28 (m, 2H), 1.86 (m, 1H), 1.78–1.60 (m, 4H).

Intermediate 42, prepared by the procedure herein above, represents the core of the Category V scaffold. The formulator can now attach the desired R unit to the scaffold, for example, a benzoyl unit as illustrated in Scheme XV herein below.

Scheme XV

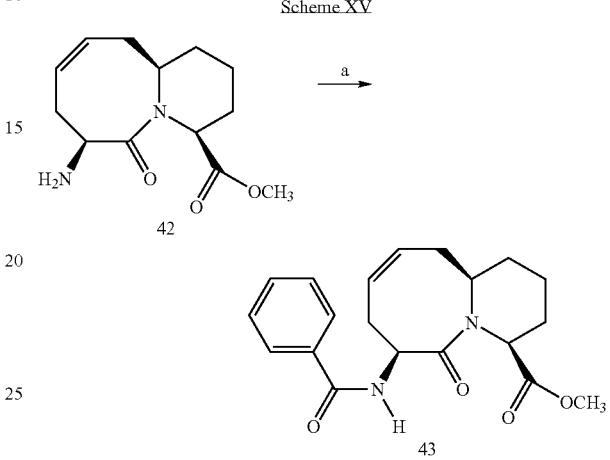

Reagents and conditions: (a) benzoyl chloride, Et$_3$N, THF.

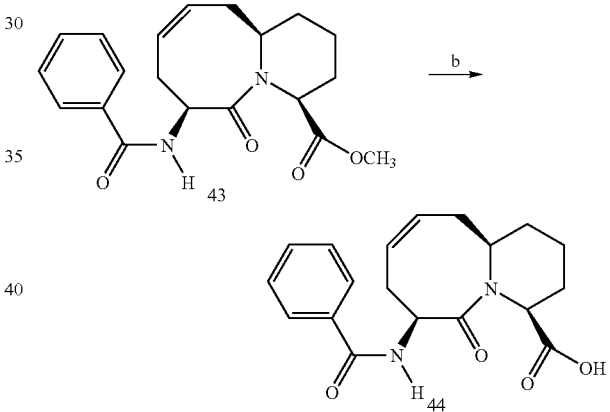

Reagents and conditions: b) LiOH, THF/H$_2$O; rt 4 hr.

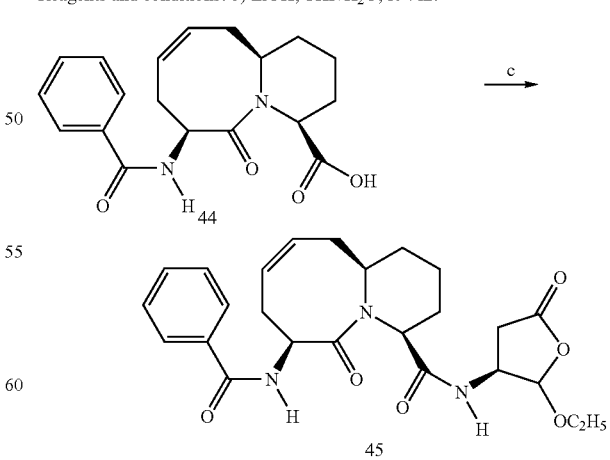

Reagents and conditions: c) (2-ethoxy-5-oxo-tetrahydrofurany-3-yl)-carbamic acid allyl ester; N,N-dimethylbarbituric acid, (Ph$_3$P)$_4$Pd, CH$_2$Cl$_2$, EDCl, HOBt.

EXAMPLE 10

(4S,7S,11aR)-7-Benzoylamino-6-oxo-1,3,4,6,7,8,11,11a-octahydro-2H-pyrido[1,2-a]azocine-4-carboxylic acid (2-ethoxy-5-oxo-tetrahydro-furan-3-yl)-amide (45)

Preparation of (4S,7S,11aR)-7-benzoylamino-6-oxo-1,3,4,6,7,8,11,11a-octahydro-2H-pyrido[1,2-a]azocine-4-carboxylic acid methyl ester (43): A solution containing crude 7-amino-6-oxo-1,3,4,6,7,8,11,11a-octahydro-2H-pyrido[1,2-a]azocine-4-carboxylic acid methyl ester, 42, (50 mg, 0.2 mmol) and Et$_3$N (0.56 mL, 4.0 mmol) in 5 mL THF is treated with excess benzoyl chloride (0.23 mL, 2.0 mmol) and stirred for 5 minutes. The reaction is quenched with MeOH and concentrated. The crude residue obtained is purified by preparative reverse phase HPLC (CH$_3$CN/H$_2$O) to yield 45 mg of desired product. $^1$H NMR (CDCl$_3$) δ 7.92 (d, J=5.9 Hz, 1H), 7.87 (d, J=7.7 Hz, 2H), 7.57–7.42 (m, 3H), 5.70 (m, 2H), 5.30 (m, 1H), 5.18 (m, 1H), 4.63 (m, 1H), 3.74 (s, 3H), 3.12 (m, 1H), 2.67 (m, 1H), 2.52 (m, 1H), 2.29 (m, 2H), 1.90–1.60 (m, 5H); $^{13}$C NMR δ 172.8, 172.3, 166.4, 134.4, 131.8, 129.9, 128.8(2C), 127.3(2C), 125.0, 52.3, 51.8, 51.4, 50.8, 35.4, 34.2, 29.7, 26.4, 15.7.

Preparation of (4S,7S,11aR)-7-benzoylamino-6-oxo-1,3,4,6,7,8,11,11a-octahydro-2H-pyrido[1,2-a]azocine-4-carboxylic acid (44): 7-Benzoylamino-6-oxo-1,3,4,6,7,8,11,11a-octahydro-2H-pyrido[1,2-a]azocine-4-carboxylic acid methyl ester, 43, (45 mg, 0.13 mmol) is dissolved in 4 mL of 3:1 THF/H$_2$O and treated with excess LiOH. The solution is stirred for 6 h, acidified with 1 N HCl, and extracted with EtOAc. The combined EtOAc extracts are washed with brine, dried (MgSO$_4$), and concentrated to yield 40 mg of the desired acid. The crude product is used without purification. $^1$H NMR (CDCl$_3$) δ 7.94–7.86 (m, 3H), 7.58–7.45 (m, 3H), 5.85–5.61 (m, 2H), 5.39 (m, 1H), 5.02 (br d, J=5.1 Hz, 1H), 4.68 (m, 1H), 3.22 (m, 1H), 2.67 (m, 1H), 2.48 (m, 1H), 2.35 (m, 2H), 2.06–1.60 (m, 5H).

Preparation of (4S,7S,11aR)-7-benzoylamino-6-oxo-1,3,4,6,7,8,11,11a-octahydro-2H-pyrido[1,2-a]azocine-4-carboxylic acid (2-ethoxy-5-oxo-tetrahydro-furan-3-yl)-amide (45) A catalytic amount of Pd(Ph$_3$P)$_4$ (35 mg, 0.03 mmol) is added to a solution of (2-Ethoxy-5-oxo-tetrahydrofuran-3-yl)-carbamic acid allyl ester (69 mg, 0.3 mmol) and N,N-dimethylbarbituric acid (156 mg, 1.0 mmol) in 2 mL CH$_2$Cl$_2$ at room temperature. The solution is stirred at rt for 15 minutes and (4S,7S,11aS)-7-benzoylamino-6-oxo-1,3,4,6,7,8,11,11a-octahydro-2H-pyrido[1,2-a]azocine-4-carboxylic acid, 44, (40 mg, 0.12 mmol) is added as a solution in 1 mL CH$_2$Cl$_2$, followed by 1-hydroxybenzotriazole (41 mg, 0.3 mmol) and 1-(3-dimethyl-aminopropyl)-3-ethyl-carbodiimide hydrochloride (58 mg, 0.3 mmol). The solution is stirred for 4 hours, diluted with EtOAc, washed with saturated NaHCO$_3$ and brine, dried (MgSO$_4$), and concentrated in vacuo. Purification by flash chromatography over silica gel afforded 32 mg of the desired product. $^1$H NMR (CDCl$_3$) δ 7.88 (m, 2H), 7.72 (m, 1H), 7.51 (m, 3H), 5.75–5.25 (series of m, 4H), 5.02 (d, J=5.8 Hz, 1H), 4.66 (m, 2H), 3.98 (dq, J=9.3, 7.0 Hz, 1H), 3.73 (dq, J=9.3, 7.0 Hz, 1H), 3.24 (m, 1H), 2.96–1.45 (series of m, 11H), 1.37 (t, J=7.0 Hz, 3H); MS 470 (M+H)$^+$.

The compounds of this aspect of Category V can also comprise the bio-active form which is the cysteine trap 2-hydroxy-5-oxo-tetrahydrofuran-3-yl and can be prepared by the procedure outlined in Scheme XVI. The example below converts compound 45 (analog 398 from Table V) to compound 46 (analog 397 from Table V).

Scheme XVI

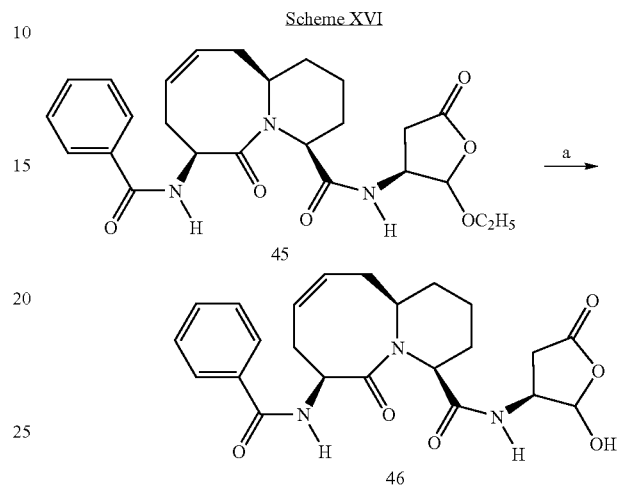

Reagents and conditions: (a) TFA, acetonitrile/water; rt 2 hr.

EXAMPLE 11

(4S,7S,11aR)-7-Benzoylamino-6-oxo-1,3,4,6,7,8,11,11a-octahydro-2H-pyrido[1,2-a]azocine-4-carboxylic acid (2-hydroxy-5-oxo-tetrahydrofuran-3-yl)-amide (46)

Preparation of (4S,7S,11aR)-7-benzoylamino-6-oxo-1,3,4,6,7,8,11,11a-octahydro-2H-pyrido[1,2-a]azocine-4-carboxylic acid (2-hydroxy-5-oxo-tetrahydrofuran-3-yl)-amide (46): A solution of (4S,7S,11aS)-7-benzoylamino-6-oxo-1,3,4,6,7,8,11,11a-octahydro-2H-pyrido[1,2-a]azocine-4-carboxylic acid (2-ethoxy-5-oxo-tetrahydro-furan-3-yl)-amide, 45, (32 mg) in 10 mL of 1:1 acetonitrile/water is treated with 2 mL of trifluoroacetic acid. After stirring for 30 minutes the solution is concentrated in vacuo and the crude product purified by preparative reverse phase HPLC to afford 21 mg of the desired product as a white solid. $^1$H NMR (CD$_3$OD) δ 7.92 (d, J=7.0 Hz, 2H), 7.54 (m, 3H), 5.75 (m, 1H), 5.63 (m, 1H), 5.42 (dd, J=8.1, 4.8 Hz, 1H), 5.01 (d, J=6.2 Hz, 1H), 4.72 (m, 1H0, 4.65 (d, J=4.0 Hz, 0.5H), 4.64 (d, J=4.0 Hz, 0.5 H), 4.31 (m, 1H), 3.18 (m, 1H), 2.68 (m, 2H), 2.45 (m, 3H), 2.26 (br d, J=13.9 Hz, 1H), 2.10 (m, 1H), 1.94 (m, 1H), 1.80 (br d, J=13.2 Hz, 1H), 1.61 (m, 2H); MS 442 (M+H)$^+$.

(4S,7S,11aR)-7-[(Isoquinoline-1-carbonyl)-amino]-6-oxo-1,3,4,6,7,8,11,11a-octahydro-2H-pyrido[1,2-a]azocine-4-carboxylic acid (2-hydroxy-5-oxo-tetrahydrofuran-3-yl)-amide $^1$H NMR (acetone-d$_6$) δ 9.60 (m, 2H), 8.68 (m, 1H), 8.10 (m, 2H), 7.84 (m, 2H), 6.00–5.35 (m, 4H), 5.20–4.70 (m, 3H), 3.40 (m, 1), 3.10–1.50 (series of m, 11H); MS 493 (M+H)$^+$.

(4S,7S,11aR)-6-Oxo-7-(3-phenyl-ureido)-1,3,4,6,7,8,11,11a-octahydro-2H-pyrido[1,2-a]azocine-4-carboxylic acid (2-hydroxy-5-oxo-tetrahydro-furan-3-yl)-amide ¹H NMR (acetone-d₆) δ 7.56 (d, J=8.0 Hz, 2H), 7.26 (dd, J=8.0, 7.7 Hz, 2H), 6.95 (t, J=7.7 Hz, 1H), 5.60 (m, 3H), 5.20 (m, 2H), 4.50 (m, 2H), 3.20–1.50 (series of m, 12H); MS 457 (M+H)⁺.

(4S,7S,11aR)-7-(3-Chloro-benzoylamino)-6-oxo-1,3,4,6,7,8,11,11a-octahydro-2H-pyrido[1,2-a]azocine-4-carboxylic acid (2-hydroxy-5-oxo-tetrahydro-furan-3-yl)-amide: ¹H NMR (CD₃OD) δ 7.95 (dd, J=1.8, 1.8 Hz, 1H), 7.85 (ddd, J=8.0, 1.8, 1.1 Hz, 1H), 7.60 (ddd, J=8.0, 1.8, 1.1 Hz, 1H), 7.51 (dd, J=8.0, 8.0 Hz, 1H), 5.76 (m, 1H), 5.63 (m, 1H), 5.42 (dd, J=8.4, 4.7 Hz, 1H), 5.00 (d, J=6.2 Hz, 1H), 4.72 (m, 1H), 4.65 (dd, J=4.4, 3.6 Hz, 1H), 4.32 (m, 1H), 3.18 (ddd, J=15.4, 7.0, 7.0 Hz, 1H), 2.67 (m, 2H), 2.44 (m, 3H), 2.25 (br d, J=13.9 Hz, 1H), 2.10 (m, 1H), 1.94 (m, 1H0, 1.78 (br d, J=12.8 Hz, 1H), 1.61 (m, 2H); MS 476, 478 (M+H).

(4S,7S,11aR)-6-Oxo-7-(3-trifluoromethyl-benzoylamino)-1,3,4,6,7,8 ,11,11a-octahydro-2H-pyrido[1,2-a]azocine-4-carboxylic acid (2-hydroxy-5-oxo-tetrahydro-furan-3-yl)-amide ¹H NMR (CD₃OD) δ 8.25 (s, 1H), 8.19 (d, J=8.0 Hz, 1H), 7.90 (d, J=8.0 Hz, 1H), 7.73 (dd, J=8.0, 8.0 Hz, 1H), 5.76 (m, 1H), 5.64 (m, 1H), 5.45 (dd, J=8.4, 4.8 Hz, 1H), 5.00 (d, J=6.6 Hz, 1H), 4.73 (m, 1H), 4.64 (dd, J=4.4, 4.0 Hz, 1H), 4.32 (m, 1H), 3.20 (m, 1H), 2.70 (m, 2H), 2.46 (m, 3H), 2.25 (br d, J=13.2 Hz, 1H), 2.11 (m, 1H), 1.96 (m, 1H), 1.78 (br d, J=14.3 Hz, 1H), 1.62 (m, 2H); MS 510 (M+H)

(4S,7S,11aR)-7-[(benzo[b]thiophene-2-carbonyl)-amino]-6-oxo-1,3,4,6,7,8,11,11a-octahydro-2H-pyrido[1,2-a]azocine-4-carboxylic acid (2-hydroxy-5-oxo-tetrahydro-furan-3-yl)-amide ¹H NMR (CD₃OD) δ 8.12 (s, 1H), 7.94 (m, 2H), 7.47 (m, 2H), 5.76 (m, 1H), 5.43 (dd, J=8.4, 4.8 Hz, 1H), 5.01 (d, J=6.2 Hz, 1H), 4.70 (m, 1H), 4.65 (dd, J=4.4, 3.7 Hz, 1H), 4.32 (m, 1H), 3.20 (m, 1H), 2.68 (m, 2H), 2.44 (m, 3H), 2.24 (br d, J=13.5 Hz, 1H), 2.10 (m, 1H), 1.94 (m, 1H), 1.79 (m, 1H), 1.60(m, 2H); MS 498 (M+1)

(4S,7S,11aR)-7-[(Naphthalene-2-carbonyl)-amino]-6-oxo-1,3,4,6,7,8 ,11,11a-octahydro-2H-pyrido[1,2-a]azocine-4-carboxylic acid (2-hydroxy-5-oxo-tetrahydro-furan-3-yl)-amide ¹H NMR (CD₃OD) δ 8.49 (s, 1H), 8.00 (m, 4H), 7.61 (m, 2H), 5.78 (m, 1H), 5.64 (m, 1H), 5.48 (dd, J=8.4, 4.8 Hz, 1H), 5.02 (d, J=6.2 Hz, 1H), 4.74 (m, 1H), 4.66 (dd, J=4.0, 4.0 Hz, 1H), 4.34 (m, 1H), 3.22 (m, 1H), 2.69 (m, 2H), 2.48 (m, 3H), 2.26 (br d, J=13.6 Hz, 1H), 2.16 (m, 1H), 1.96 (m, 1H), 1.80 (br d, J=14.6 Hz, 1H), 1.62 (m, 2H); MS 492 (M+1).

(4S,7S,11aR)-9-methyl-5-oxo-6-(3-trifluoromethyl-benzoylamino)-1,3,4,5,6,7,10,10a,-octahydro-2-oxa-4a-azabenzocyclooctene-4-carboxylic acid-(2-hydroxy-5-oxotetrahydrofuran-3-yl)-amide: ¹H NMR (CD₃OD): δ 8.19 (m, 2H), 7.89 (d, J=8.0 Hz, 1H), 7.72 (t, J=8.1 Hz, 1H), 5.57 (m, 1H), 5.35 (dd, J=8.4, 3.3 Hz, 1H), 4.69 (m, 2H), 4.49 (m, 1H), 4.33 (m, 2H), 3.82 (m, 2H), 3.69 (m, 1H), 3.20 (m, 1H), 2.79 (m, 1H), 2.64 (m, 1H), 2.49 (m, 2H), 2.34 (m, 1H), 1.75 (s, 3H); ESI MS 526.08 (M+H).

(4S,7S,11aR)-9-methyl-6-[(naphthalene-2-carbonyl)-amino]-5-oxo-1,3,4,5,6,7,10,10a,-octahydro-2-oxa-4a-azabenzocyclooctene-4-carboxylic acid-(2-hydroxy-5-oxotetrahydrofuran-3-yl)-amide: ¹H NMR (CD₃OD): δ 8.50 (m, 1H), 7.99 (m, 4H), 7.62 (m, 3H), 5.60 (m, 1H), 5.39 (m, 1H), 4.71 (m, 2H), 4.54 (m, 1H), 4.37 (m, 2H), 3.85 (m, 2H), 3.69 (m, 1H), 3.22 (m, 1H), 2.89–2.64 (m, 2H), 2.55–2.34 (m, 3H), 1.77 (s, 3H); ESI MS 508.10 (M+H).

Category VI of the interleukin-1β converting enzyme inhibitors according to the present invention relates to compound comprising a 4,7-disubstituted decahydro-pyrido[1,2-a]azocin-6-one scaffold having the formula:

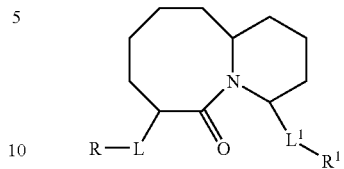

one iteration of the first aspect of this Category comprises scaffolds having the indicated stereochemistry. Table VI relates to non-limiting examples of analogs comprising a first aspect of this category, said analogs having the formula:

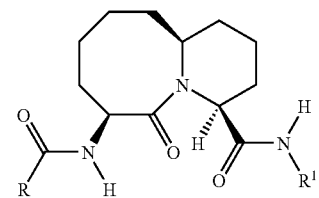

wherein R and R¹ are defined in Table VI herein below.

TABLE VI

| No. | R | R¹ |
|---|---|---|
| 469 | phenyl | 2-hydroxy-5-oxo-tetrahydrofuran-3-yl |
| 470 | phenyl | 2-ethoxy-5-oxo-tetrahydrofuran-3-yl |
| 471 | quinolin-2-yl | 2-hydroxy-5-oxo-tetrahydrofuran-3-yl |
| 472 | quinolin-2-yl | 2-ethoxy-5-oxo-tetrahydrofuran-3-yl |
| 473 | benzothiophen-2-yl | 2-hydroxy-5-oxo-tetrahydrofuran-3-yl |
| 474 | benzothiophen-2-yl | 2-ethoxy-5-oxo-tetrahydrofuran-3-yl |
| 475 | 2-thienyl | 2-hydroxy-5-oxo-tetrahydrofuran-3-yl |
| 476 | 2-thienyl | 2-ethoxy-5-oxo-tetrahydrofuran-3-yl |
| 477 | isoquinolin-1-yl | 2-hydroxy-5-oxo-tetrahydrofuran-3-yl |
| 478 | isoquinolin-1-yl | 2-ethoxy-5-oxo-tetrahydrofuran-3-yl |
| 479 | naphth-1-yl | 2-hydroxy-5-oxo-tetrahydrofuran-3-yl |
| 480 | naphth-1-yl | 2-ethoxy-5-oxo-tetrahydrofuran-3-yl |
| 481 | naphth-2-yl | 2-hydroxy-5-oxo-tetrahydrofuran-3-yl |
| 482 | naphth-2-yl | 2-ethoxy-5-oxo-tetrahydrofuran-3-yl |
| 483 | 3-fluorophenyl | 2-hydroxy-5-oxo-tetrahydrofuran-3-yl |
| 484 | 3-fluorophenyl | 2-ethoxy-5-oxo-tetrahydrofuran-3-yl |
| 485 | 4-fluorophenyl | 2-hydroxy-5-oxo-tetrahydrofuran-3-yl |
| 486 | 4-fluorophenyl | 2-ethoxy-5-oxo-tetrahydrofuran-3-yl |
| 487 | 3,4-difluorophenyl | 2-hydroxy-5-oxo-tetrahydrofuran-3-yl |
| 488 | 3,4-difluorophenyl | 2-ethoxy-5-oxo-tetrahydrofuran-3-yl |
| 489 | 4-fluorothienyl | 2-hydroxy-5-oxo-tetrahydrofuran-3-yl |
| 490 | 4-fluorothienyl | 2-ethoxy-5-oxo-tetrahydrofuran-3-yl |
| 491 | 2-aminopyrimidinyl | 2-hydroxy-5-oxo-tetrahydrofuran-3-yl |
| 492 | 2-aminopyrimidinyl | 2-ethoxy-5-oxo-tetrahydrofuran-3-yl |
| 493 | 2-phenylamino-4-pyrimidinyl | 2-hydroxy-5-oxo-tetrahydrofuran-3-yl |
| 494 | 2-phenylamino-4-pyrimidinyl | 2-ethoxy-5-oxo-tetrahydrofuran-3-yl |
| 495 | 2-phenoxy-4-pyrimidinyl | 2-hydroxy-5-oxo-tetrahydrofuran-3-yl |
| 496 | 2-phenoxy-4-pyrimidinyl | 2-ethoxy-5-oxo-tetrahydrofuran-3-yl |
| 497 | 2-benzoxy-4-pyrimidinyl | 2-hydroxy-5-oxo-tetrahydrofuran-3-yl |
| 498 | 2-benzoxy-4-pyrimidinyl | 2-ethoxy-5-oxo-tetrahydrofuran-3-yl |
| 499 | 2-methoxy-4-pyrimidinyl | 2-hydroxy-5-oxo-tetrahydrofuran-3-yl |
| 500 | 2-methoxy-4-pyrimidinyl | 2-ethoxy-5-oxo-tetrahydrofuran-3-yl |
| 501 | isoquinolin-3-yl | 2-hydroxy-5-oxo-tetrahydrofuran-3-yl |
| 502 | isoquinolin-3-yl | 2-ethoxy-5-oxo-tetrahydrofuran-3-yl |
| 503 | 2-phenylamino-4-pyridinyl | 2-hydroxy-5-oxo-tetrahydrofuran-3-yl |
| 504 | 2-phenylamino-4-pyridinyl | 2-ethoxy-5-oxo-tetrahydrofuran-3-yl |
| 505 | 2-phenoxy-4-pyridinyl | 2-hydroxy-5-oxo-tetrahydrofuran-3-yl |
| 506 | 2-phenoxy-4-pyridinyl | 2-ethoxy-5-oxo-tetrahydrofuran-3-yl |
| 507 | 2-benzoxy-4-pyridinyl | 2-hydroxy-5-oxo-tetrahydrofuran-3-yl |

TABLE VI-continued

| No. | R | R¹ |
|---|---|---|
| 508 | 2-benzoxy-4-pyridinyl | 2-ethoxy-5-oxo-tetrahydrofuran-3-yl |
| 509 | 2-methoxy-4-pyridinyl | 2-hydroxy-5-oxo-tetrahydrofuran-3-yl |
| 510 | 2-methoxy-4-pyridinyl | 2-ethoxy-5-oxo-tetrahydrofuran-3-yl |
| 511 | 4-hydroxyphenyl | 2-hydroxy-5-oxo-tetrahydrofuran-3-yl |
| 512 | 4-hydroxyphenyl | 2-ethoxy-5-oxo-tetrahydrofuran-3-yl |
| 513 | 4-methylphenyl | 2-hydroxy-5-oxo-tetrahydrofuran-3-yl |
| 514 | 4-methylphenyl | 2-ethoxy-5-oxo-tetrahydrofuran-3-yl |
| 515 | 2-trifluoromethylphenyl | 2-hydroxy-5-oxo-tetrahydrofuran-3-yl |
| 516 | 2-trifluoromethylphenyl | 2-ethoxy-5-oxo-tetrahydrofuran-3-yl |
| 517 | 3-trifluoromethylphenyl | 2-hydroxy-5-oxo-tetrahydrofuran-3-yl |
| 518 | 3-trifluoromethylphenyl | 2-ethoxy-5-oxo-tetrahydrofuran-3-yl |
| 519 | 4-trifluoromethylphenyl | 2-hydroxy-5-oxo-tetrahydrofuran-3-yl |
| 520 | 4-trifluoromethylphenyl | 2-ethoxy-5-oxo-tetrahydrofuran-3-yl |

The compounds comprising Category VI of the present invention can be suitably prepared under most circumstances from the corresponding Category V compounds by direct reduction of the 8-member ring double bond, for example, the conversion of compound 46 to 47 as depicted herein below in Scheme XVII.

Scheme XVII

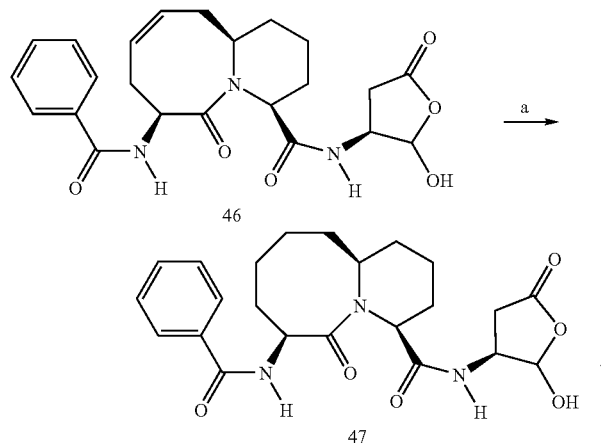

Reagents and conditions: (a) H₂: Pd/C, EtOAc

EXAMPLE 12

Preparation of (4S,7S,11aS)-7-benzoylamino-6-oxo-decahydro-pyrido[1,2-a]azocine-4-carboxylic acid (2-hydroxy-5-oxo-tetrahydro-furan-3-yl)-amide (47): (4S,7S,11aR)-7-benzoylamino-6-oxo-1,3,4,6,7,8,11,11a-octahydro-2H-pyrido[1,2-a]azocine-4-carboxylic acid (2-hydroxy-5-oxo-tetrahydrofuran-3-yl)-amide, 46, is dissolved in EtOAc and treated with a catalytic amount of Pd/C. The resulting suspension is stirred at room temperature under a H₂ atmosphere for 2 hours. The solution is filtered to remove the catalyst and concentrated in vacuo to afford the desired product The cysteine traps of the present invention can be prepared by any convenient method selected by the formulator. The following is a description of the preparation of (2-ethoxy-5-oxo-tetrahydrofuran-3-yl)-carbamic acid allyl ester which is used to introduce one category of cysteine trap into the scaffolds of the present invention.

Scheme XVIII

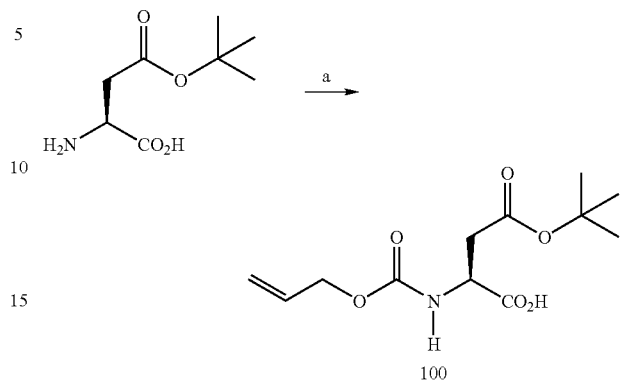

Reagents and conditions: (a) allyl chloroformate, NaHCO₃, THF/H₂O (3:1).

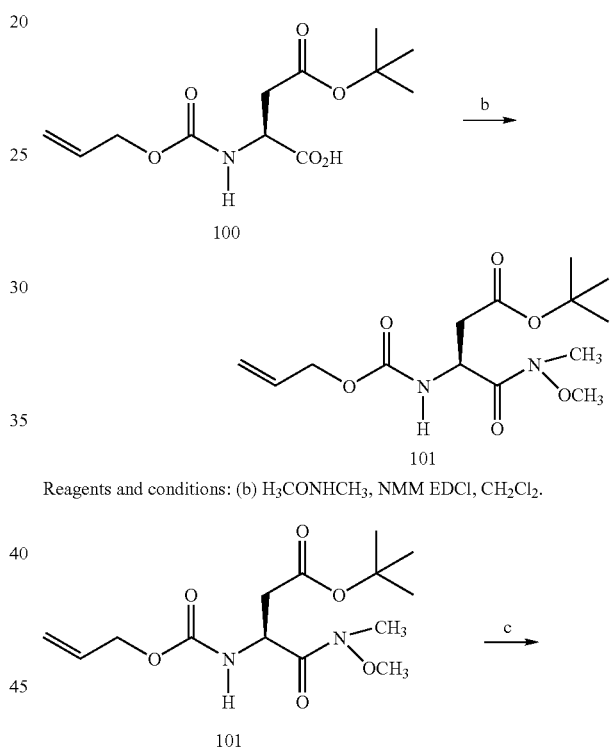

Reagents and conditions: (b) H₃CONHCH₃, NMM EDCl, CH₂Cl₂.

Reagents and conditions: (c) LAH, THF/H₂O (3:1).

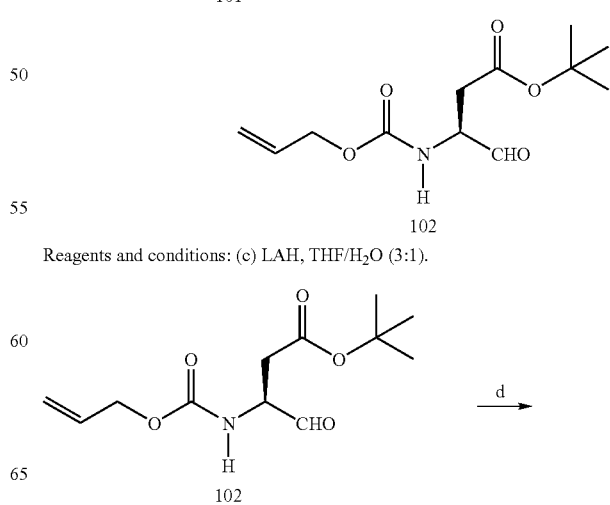

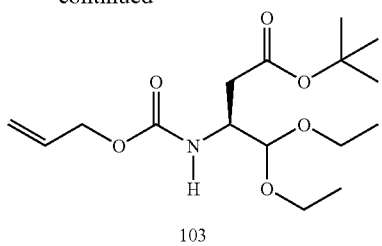

103

Reagents and conditions: (d) CH(OC₂H₅)₃, PTSA, EtOH.

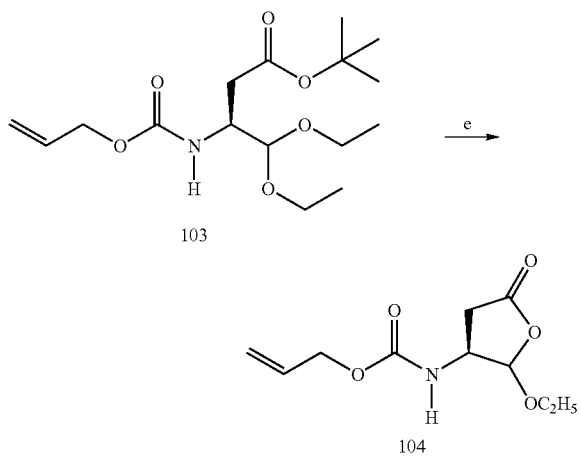

Reagents and conditions: (e) TFA, CH₂Cl₂.

EXAMPLE 13

(2-Ethoxy-5-oxo-tetrahydro-furan-3-yl)-carbamic acid allyl ester (104)

Preparation of 2-allyloxycarbonylamino-succinic acid 4-tert-butyl ester (100): L-aspartic acid β-t-butyl ester (30.3 g, 0.160 mol) is dissolved in 100 mL THF and 300 mL H₂O. Under cooling (ice bath) and with stirring, allyl chloroformate (38.8 mL, 44.1 g, 0.365 mol) and sodium bicarbonate (60.1 g, 0.715 mol) are added in one portion. After the consumption of the starting material, the mixture is acidified to a pH of 2 using 6 N HCl and then extracted with ether (3×400 mL). The ether layer is dried with MgSO₄ and concentrated under reduced pressure. The residue is purified over silica (CH₂Cl₂/MeOH/acetic acid 3:97:0.1) to furnish 40.7 g (90% yield) of the desired product as a clear oil.

Preparation of 3-allyloxycarbonylamino-N-methoxy-N-methyl-succinamic acid tert-butyl ester (101): 2-Allyloxycarbonylamino-succinic acid 4-tert-butyl ester, 100, (43.4 g, 0.159 mol) is dissolved in CH₂Cl₂(900 mL). To this solution O,N-dimethyl-hydroxylamine hydrochloride (18.6 g, 0.191 mol), 4-Methyl-morpholine (21.0 mL, 19.3 g, 0.191 mol), and 1-(3-Dimethylaminopropyl)-3-ethylcarbodiimide hydrochloride (36.6 g, 0.191 mol) are added. After the consumption of the starting material, the solution is washed with 1.0 N HCl (2×400 mL) and brine (1×250 mL). The organic layer is concentrated in vacuo and the residue purified over silica (hexanes/ethyl acetate 65:35) to afford 40.8 g (81% yield) of the desired product as a clear oil.

Preparation of 3-allyloxycarbonylamino-4-oxo-butyric acid tert-butyl ester (102): A solution of 3-allyloxycarbonylamino-N-methoxy-N-methyl-succinamic acid tert-butyl ester, 101, (24.3 g, 76.8 mmol) in THF (60 mL) is treated at −78° C. with lithium aluminum hydride (1 M in THF, 39 mL, 39 mmol) dissolved in ether (200 mL) over 5 minutes. After the consumption of starting material, the solution is cautiously quenched with 1.0 N HCl, washed with 1.0 N HCl (2×100 mL) and brine (1×150 mL). The organic layer is concentrated in vacuo to afford 18.2 g (91% yield) of the desired product as a clear oil.

Preparation of 3-allyloxycarbonylamino-4,4-diethoxy-butyric acid tert-butyl ester (103): To a solution of 3-allyloxycarbonylamino-4-oxo-butyric acid tert-butyl ester, 102, (13.3 g, 51.7 mmol) in anhydrous ethanol (75 mL) is added ethyl orthoformate (45 mL, 0.270 mol), p-toluenesulfonic acid (0.15 g, cat.) and 4 Å molecular sieves (10 g, kiln dried) under N₂. After the consumption of starting material, the sieves are removed by filtration and the solvent removed in vacuo to provide the desired compound as a clear oil which is used directly without further purification. MS (ESI): m/e=332.21 (M+H).

Preparation of (2-ethoxy-5-oxo-tetrahydro-furan-3-yl)-carbamic acid allyl ester (104). A solution of the crude 3-Allyloxycarbonylamino-4,4-diethoxy-butyric acid tert-butyl ester, 103, obtained in the procedure above, in CH₂Cl₂ (50 mL) is treated with triflouroacetic acid (50 mL). After the consumption of starting material, the organics are reduced under vacuum. The residual triflouroacetic acid is removed with ethyl acetate by azeotroping conditions. The final residue is purified over silica (hexanes/ethyl acetate 80:20) to afford 10.1 g (85% yield) of the desired product as a slightly yellow oil. ¹H-NMR, (300 MHz, CDCl₃): δ 1.23 (m, 3H), 2.41–2.54 (m, 1H), 2.82–3.06 (m, 2H), 3.61–3.73 (m, 1H), 3.82–3.98 (m, 1H), 4.06–4.25 (m, 1H), 4.61 (br s, 2H), 5.24–5.53 (m, 3H), 5.86–6.01 (m, 1H); MS (ESI): m/e=230.03 (M+H).

In the above Scheme XVIII, intermediate 102 can be converted to the bio-equivalent form of the trap wherein R⁵ is benzyl by the process outlined in Scheme XIX.

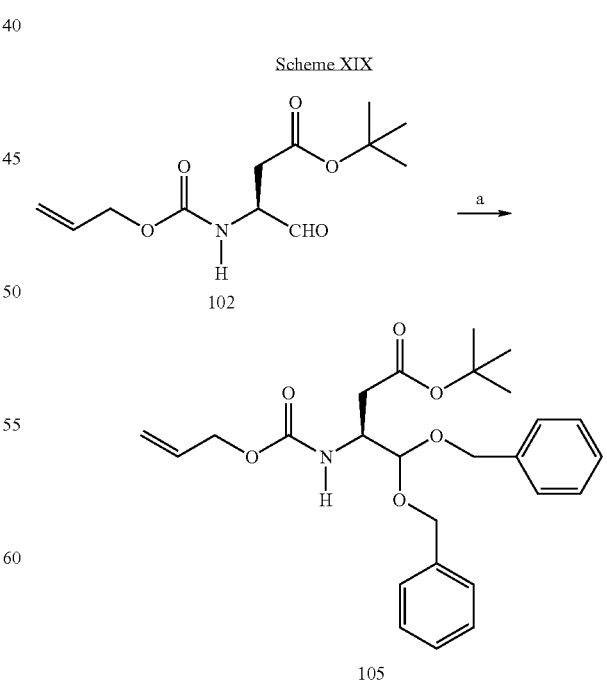

Reagents and conditions: (a) benzyl alcohol, TsOH, 3 Å sieves.

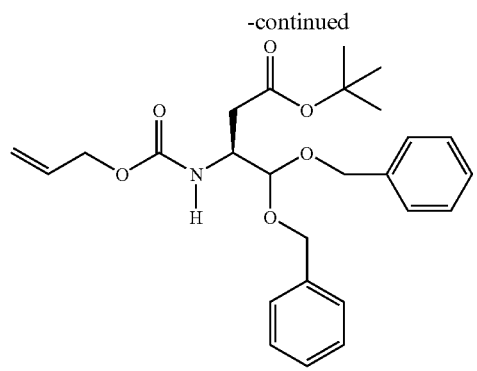

105

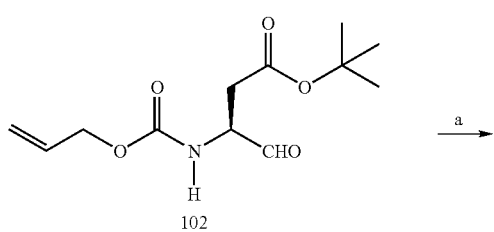

105

Reagents and conditions: (b) TFA, CH$_2$Cl$_2$.

Details for converting intermediate 102 to the bio-equivalent cysteine trap 106 can be found in K. T. Chapman *Bioorg. Med Chem. Lett.*, 2, 613–618 (1992) incorporated herein by reference.

Another category of reversible cysteine traps according to the present invention relates to units wherein J is an alkylenearyl unit having the formula —(CH)$_u$R$^{21}$. Scheme XX summarizes the preparation of a cysteine trap wherein R$^{21}$ is benzyl. For a more complete description of the preparation of bio-equivalent forms of cysteine traps comprising the second iteration of the second aspect of reversible traps according to the present invention see Adrian M. M. Mjalli et al, *Bioorg. Med Chem. Lett.*, 3, 2689–2692 (1993) incorporated herein by reference.

Scheme XX

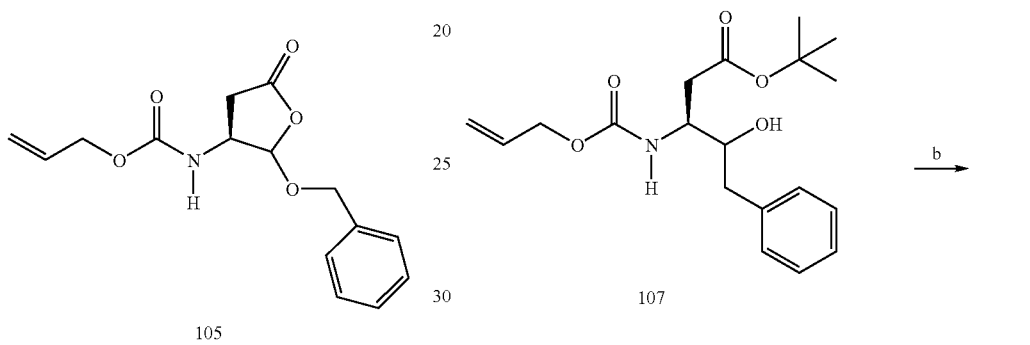

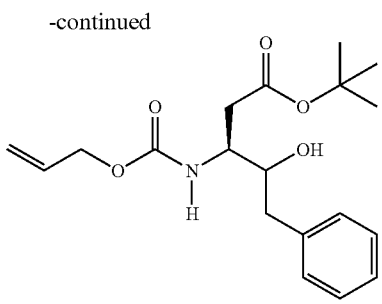

107

Reagents and conditions: (a) Benzylmagnesium chloride, THF; -78° C.

Reagents and conditions: (b) Dess-Martin reagent, CH$_2$Cl$_2$; rt, 1 hr..

Preparation of 3-allyloxycarbonylamino-4-hydroxy-5-phenyl-pentanoic acid Tert-Butyl ester (107): To a solution of benzylmagnesium chloride (20 mL, 20 mmol) in THF at −78° C. is added dropwise a 0° C. solution of 3-allyloxycarbonylamino-4-oxo-butyric acid tert-butyl ester, 102, (5.14 g, 20 mmol) in THF (100 mL). Once the addition is complete, the solution is allowed to warm to 0° C. over 30 minutes then the reaction mixture is poured into a beaker of crushed ice. The solution is extracted ×3 with CH$_2$Cl$_2$ (100 mL), the organic layers combined, dried over Na$_2$SO$_4$ and concentrated in vacuo to afford the desired product which is used without further purification.

Preparation of 3-allyloxycarbonylamino-4-oxo-5-phenyl-pentanoic acid tert-butyl ester (108): A solution of 3-allyloxycarbonylamino-4-hydroxy-5-phenyl-pentanoic acid tert-butyl ester, 107, (0.8 g, 2.23 mmol) in CH$_2$Cl$_2$ (10 mL) is added to a solution of Dess-Martin reagent (1.05 g, 2.47 mmol) in CH$_2$Cl$_2$ (10 mL). After 1 hour the reaction solution is diluted with ether (50 mL) and the solution poured into a 1.3 M solution of NaOH (20 mL). Stir for 1 hour and decant the organic layer. Dry the organic layer over Na$_2$SO$_4$, concentrate in vacuo to afford a crude residue that is purified over silica to afford the desired product.

Intermediate 108 can be directly coupled to the desired scaffold. Once coupled the formulator may choose to hydrolyze the tert-butyl ester moiety (bio-equivalent form) to the free acid (bio-active form) or convert the ester to another bio-equivalent form.

The traps of the present invention further include irreversible traps such as aryloxymethyl ketones. Scheme XXI outlines a procedure for preparing an aryloxy-methyl ketone trap and the coupling of said trap to a scaffold according to the present invention.

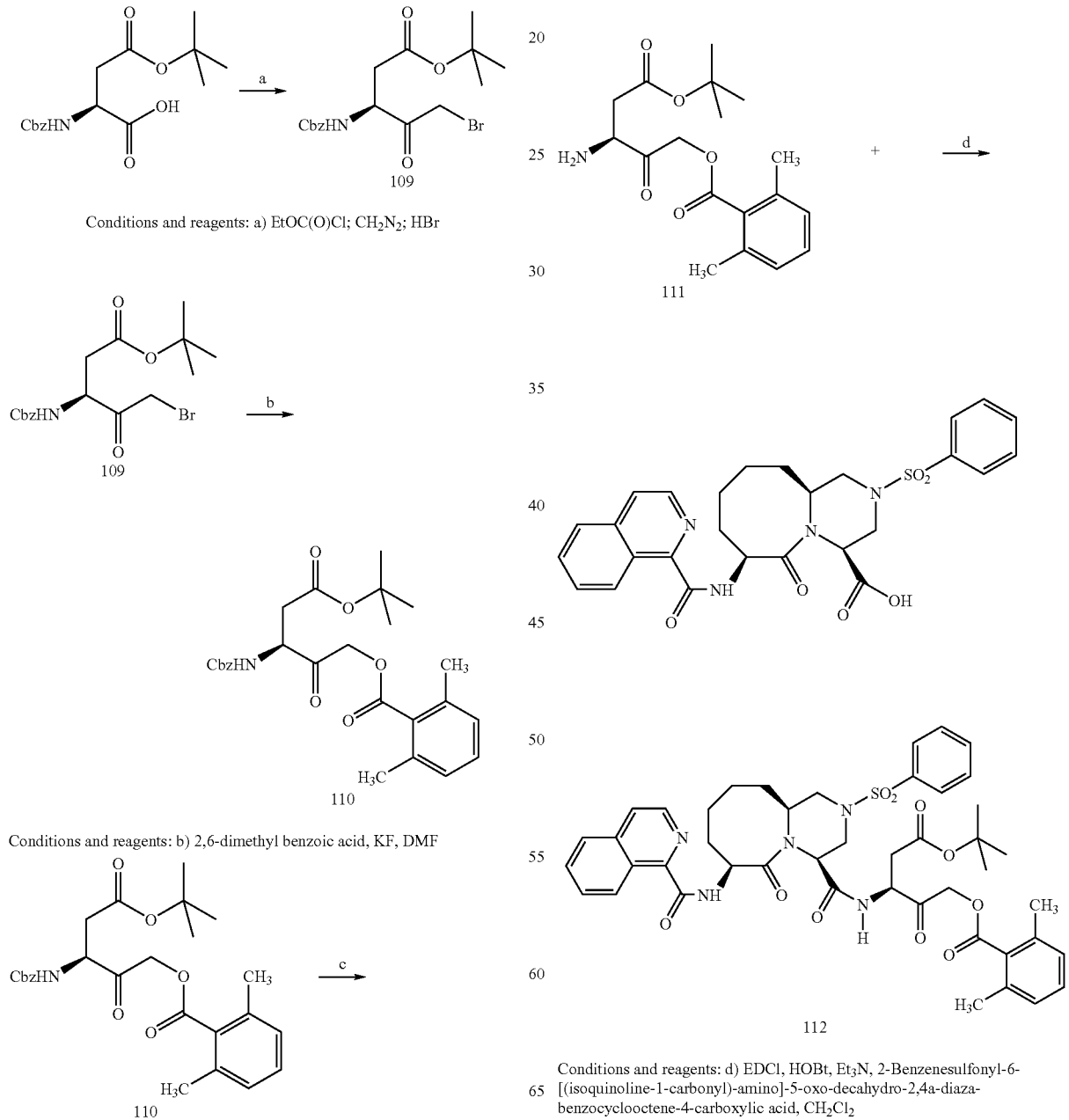

Conditions and reagents: a) EtOC(O)Cl; CH$_2$N$_2$; HBr

Conditions and reagents: b) 2,6-dimethyl benzoic acid, KF, DMF

Conditions and reagents: c) H$_2$, Pd/C, EtOH, 1N HCl

Conditions and reagents: d) EDCl, HOBt, Et$_3$N, 2-Benzenesulfonyl-6-[(isoquinoline-1-carbonyl)-amino]-5-oxo-decahydro-2,4a-diaza-benzocyclooctene-4-carboxylic acid, CH$_2$Cl$_2$

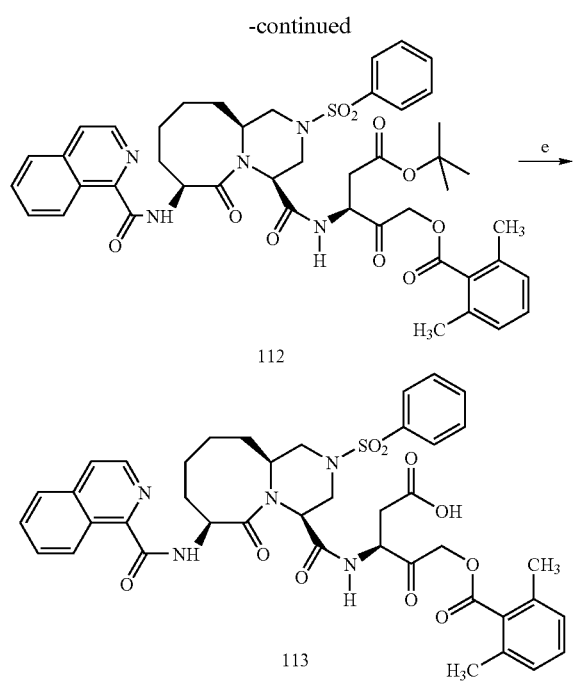

Conditions and reagents: e) TFA, CH₂Cl₂

EXAMPLE 14

2,6-Dimethyl-benzoic acid 3-({2-benzenesulfonyl-6-[(isoquinoline-1-carbonyl)-amino]-5-oxo-decahydro-2,4a-diaza-benzocyclooctene-4-carbonyl}-amino)-4-carboxy-2-oxo-butyl ester (113)

Preparation of 3-benzyloxycarbonylamino-5-bromo-4-oxo-pentanoic acid tert-butyl ester (109): To a solution containing Z-Asp(OtBu)-OH (12.92 g, 40 mmol) and 4-methylmorpholine (5.6 g, 56 mmol) in 250 mL of THF at −20° C. is added ethyl chloroformate (5.0 mL, 52 mmol). The solution is stirred at −20° C. for 20 min and then excess CH₂N₂ (an ethereal solution, freshly prepared from N-nitrosomethyl urea and dried over KOH) is added and the solution is warmed to rt. After stirring at rt for 2 h, the solution is cooled to −20° C. and treated with HBr (80 mL of a 33% solution in HOAc). The reaction is stirred for an additional 20 min, treated with 200 mL of H₂O, and diluted with EtOAc. The organic layer is separated, washed with water, saturated NaHCO₃, and brine, and dried over MgSO₄. The solution is filtered, concentrated, and purified by flash chromatography on silica gel (hexane/EtOAc) to yield 11.6 g of the desired product. ¹H NMR (CDCl₃) δ 7.40 (br s, 5H), 5.91 (d, J=8.8 Hz,1H), 5.18 (s, 2H), 4.78 (m,1H), 4.22 (s, 2H), 3.01 (dd, J=17.2, 4.8 Hz, 1H), 2.78 (dd, J=17.2, 4.8 Hz, 1H), 1.45 (s, 9H).

Preparation of 2,6-dimethyl-benzoic acid 3-benzyloxycarbonylamino-4-tert-butoxycarbonyl-2-oxo-butyl ester (110):

A heterogeneous solution containing 3-benzyloxycarbonylamino-5-bromo-4-oxo-pentanoic acid tert-butyl ester, 109, (9.89 g, 24.7 mmol), 2,6-dimethyl benzoic acid (4.45 g, 29.6 mmol), and KF (3.58 g, 61.8 mmol) in 250 mL of DMF is stirred at rt for 12 h. The solution is diluted with EtOAc, washed with water, saturated NaHCO₃, and brine, dried (MgSO₄), and concentrated in vacuo. Purification of the crude material by flash chromatography on silica gel (hexane/EtOAc) yields 11.3 g of the desired product as a white solid.

Preparation of 2,6-dimethyl-benzoic acid 3-amino-4-tert-butoxycarbonyl-2-oxo-butyl ester (111): 2,6-Dimethyl-benzoic acid 3-benzyloxycarbonylamino-4-tert-butoxycarbonyl-2-oxo-butyl ester, 110, (11.3 g, 24.1 mmol) is dissolved in a solution of EtOH (400 mL) and 1N HCl (29 mL), treated with 10% Pd/C (500 mg) and stirred under a hydrogen atmosphere for 4 h. The solution is filtered and concentrated to yield 7.6 g of the desired product as an HCl salt that was used without further purification.

Preparation of 2,6-dimethyl-benzoic acid 3-({2-benzenesulfonyl-6-[(isoquinoline-1-carbonyl)-amino]-5-oxo-decahydro-2,4a-diaza-benzocyclooctene-4-carbonyl}-amino)-4-tert-butoxycarbonyl-2-oxo-butyl ester (112): To a solution of 2-benzenesulfonyl-6-[(isoquinoline-1-carbonyl)-amino]-5-oxo-decahydro-2,4a-diaza-benzocyclooctene-4-carboxylic acid, 111, (124 mg, 0.23 mmol) in dichloromethane is added EDCl (191 mg, 1 mmol), HOBt (135 mg, 1 mmol), 2,6-dimethyl-benzoic acid 3-amino-4-tert-butoxycarbonyl-2-oxo-butyl ester (200 mg, 0.62 mmol), and triethylamine (0.15 mL, 1 mmol). After consumption of the starting material, the reaction is diluted with EtOAc and washed with water, 1N HCl, saturated NaHCO₃, and brine. The organic layer is concentrated in vacuo and the crude residue obtained is used directly in the next step without purification.

Preparation of 2,6-Dimethyl-benzoic acid 3-({2-benzenesulfonyl-6-[(isoquinoline-1-carbonyl)-amino]-5-oxo-decahydro-2,4a-diaza-benzocyclooctene-4-carbonyl}-amino)-4-carboxy-2-oxo-butyl ester (113): The crude 2,6-dimethyl-benzoic acid 3-({2-benzenesulfonyl-6-[(isoquinoline-1-carbonyl)-amino]-5-oxo-decahydro-2,4a-diaza-benzocyclooctene-4-carbonyl}-amino)-4-tert-butoxycarbonyl-2-oxo-butyl ester, 112, obtained above is treated with solution of trifluoroacetic acid (10 ml) and dichloromethane (10 ml). The mixture is stirred for 2 hours and solvent is removed in vacuo. The residue is purified by flash chromatography on silica gel (CH₂Cl₂/MeOH) to afford 120 mg of the desired product.

Scheme XXII

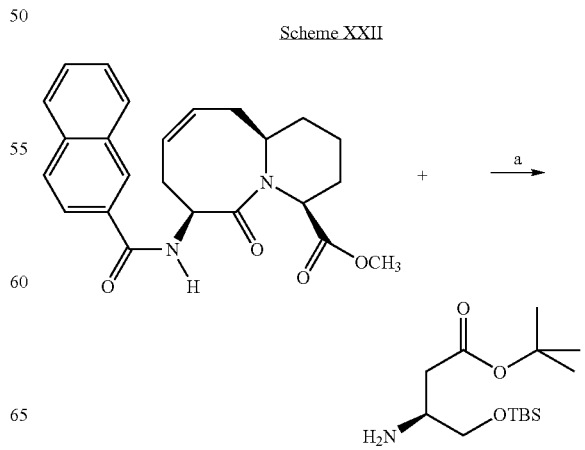

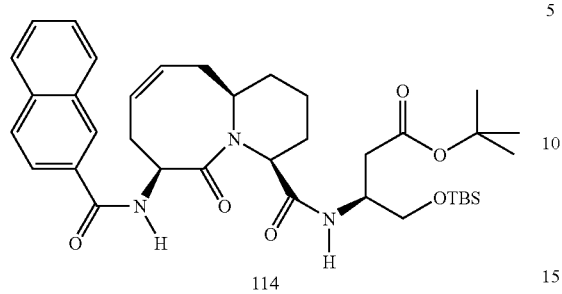
114
Reagents and conditions: a) HOBt, EDC, N-methylmorpholine, THF, RT
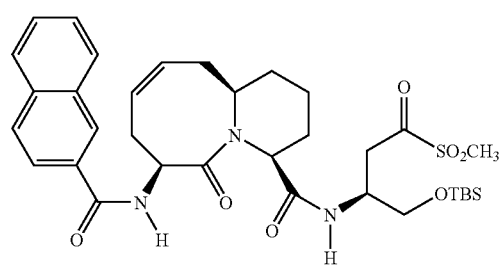
116
Reagents and conditions: c) CDI, THF, RT
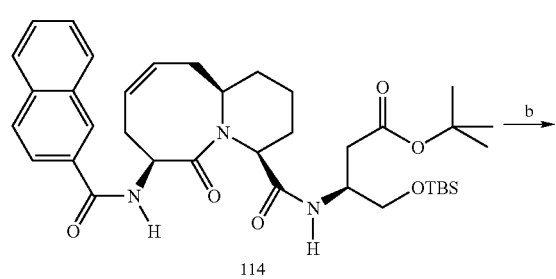
114
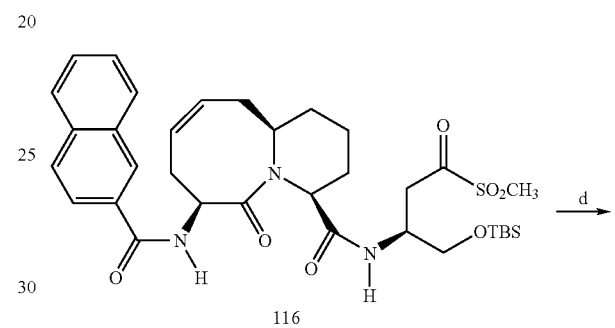
116
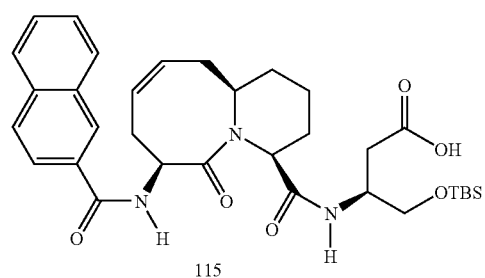
115
Reagents and conditions: b) aq. NaOH, MeOH, RT
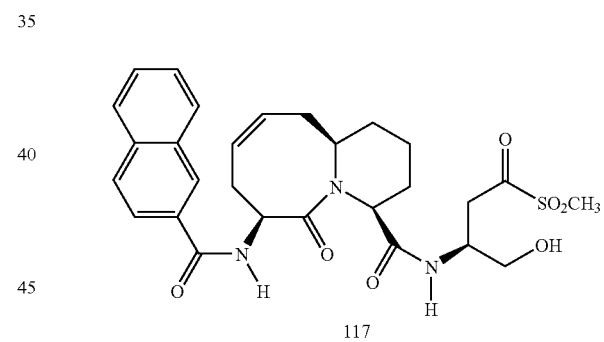
117
Reagents and conditions: d) HF·pyr, 0 deg
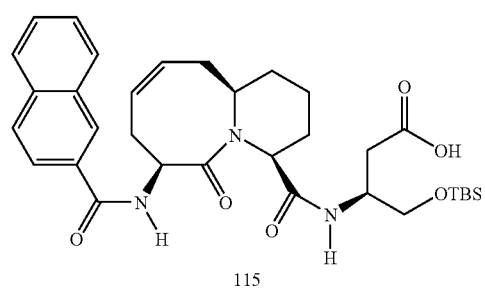
115
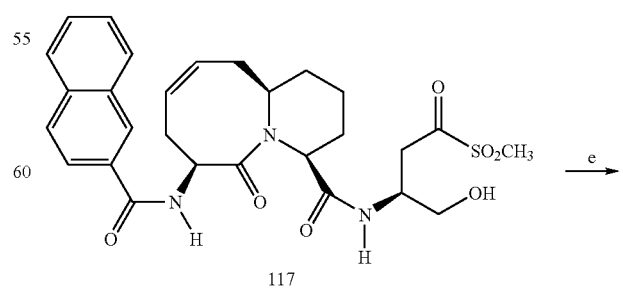
117

-continued

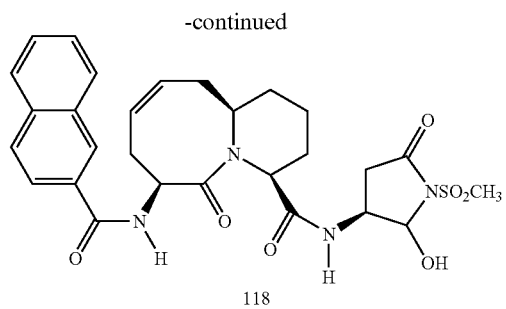

118

Reagents and conditions: e) Dess-Martin periodinane, methylene chloride, 0 deg.

EXAMPLE 15

7-[(Naphthalene-2-carbonyl)-amino]-6-oxo-1,3,4,6,7,8,11,11a-octahydro-2H-pyrido[1,2-a]azocine-4-carboxylic acid (2-hydroxy-1-methanesulfonyl-5-oxo-pyrrolidin-3-yl)-amide (118)

Preparation of 4-(tert-Butyl-dimethyl-silanyloxy)-3-({7-[(naphthalene-2-carbonyl)-amino]-6-oxo-1,3,4,6,7,8,11,11a-octahydro-2H-pyrido[1,2-a]azocine-4-carbonyl}-amino)-butyric acid benzyl ester (114): 7-[(Naphthalene-2-carbonyl)-amino]-6-oxo-1,3,4,6,7,8,11,11a-octahydro-2H-pyrido[1,2-a]azocine-4-carboxylic acid (0.44 gm) is dissolved in 15 mL THF to which 0.24 gm of 1-(3-dimethylaminopropyl)-3-ethyl-carbodiimide hydrochloride (EDC), 0.15 mL of N-methylmorpholine, and 0.17 gm of 1-hydroxybenzotriazole (HOBt) is added. The reaction mixture is stirred for 20 min then added to a solution of 3-amino-4-(tert-butyl-dimethyl-silanyloxy)-butyric acid benzyl ester (0.52 gm, prepared by methods described in Chem. Pharm. Bull. 1999, 47, 11–21) in 5 mL THF. The resulting mixture is striired at RT for ~18 h, then poured into water, and extracted with ethyl acetate. The organic layer is washed with saturated aqueous sodium bicarbonate and saturated aqueous sodium chloride, then dried over sodium sulfate powder. Filtration and evaporation produces a crude product which is then purified over silica (1:1 ethylacetate:hexanes) to afford the desired product.

Preparation of 4-(tert-butyl-dimethyl-silanyloxy)-3-({7-[(naphthalene-2-carbonyl)-amino]-6-oxo-1,3,4,6,7,8,11,11a-octahydro-2H-pyrido[1,2-a]azocine-4-carbonyl}-amino)-butyric acid (115): 4-(tert-Butyl-dimethyl-silanyloxy)-3-({7-[(naphthalene-2-carbonyl)-amino]-6-oxo-1,3,4,6,7,8,11,11a-octahydro-2H-pyrido[1,2-a]azocine-4-carbonyl}-amino)-butyric acid benzyl ester, 114, (0.52 gm) is dissolved in 10 mL methanol, to which 1.73 mL of 1N aqueous sodium hydroxide is added at RT. The reaction is stirred for 5 h and a second aliquot (0.7 mL) of 1N sodium hydroxide solution is added. The reaction is allowed to proceed for 18 h at RT. Water is added and the mixture is extracted three times with diethyl ether. The aqueous layer is then acidified to pH ~3 with 10% aqueous citric acid, and extracted with ethyl acetate. The organic layer is washed with saturated aqueous sodium chloride, dried over sodium sulfate powder, and concentrated in vauo to afford the desired product.

Preparation of 7-[(naphthalene-2-carbonyl)-amino]-6-oxo-1,3,4,6,7,8,11,11a-octahydro-2H-pyrido[1,2-a]azocine-4-carboxylic acid [1-(tert-butyl-dimethyl-silanyloxymethyl)-3-methanesulfonylamino-3-oxo-propyl]-amide (116): To a solution of 4-(tert-butyl-dimethyl-silanyloxy)-3-({7-[(naphthalene-2-carbonyl)-amino]-6-oxo-1,3,4,6,7,8,11,11a-octahydro-2H-pyrido[1,2-a]azocine-4-carbonyl}-amino)-butyric acid, 115, (0.23 gm) in 6 mL THF is added 0.12 gm carbonyl diimidazole, and the reaction is stirred for 3 h at RT. Then, 0.035 gm methansulfonamide and 0.11 mL 1,8-diazabicyclo[5.4.0]-7-undecene is added, and the reaction conitnues for another 3 h at RT. The mixture is then evaporated in vacuo and the crude residue is purified over silica (5% methanol in methylene chloride) to afford the desired product.

Preparation of 7-[(naphthalene-2-carbonyl)-amino]-6-oxo-1,3,4,6,7,8,11,11a-octahydro-2H-pyrido[1,2-a]azocine-4-carboxylic acid (1-hydroxymethyl-3-methanesulfonylamino-3-oxo-propyl)-amide (117): To an ice-cooled solution of 7-[(naphthalene-2-carbonyl)-amino]-6-oxo-1,3,4,6,7,8,11,11a-octahydro-2H-pyrido[1,2-a]azocine-4-carboxylic acid [1-(tert-butyl-dimethyl-silanyloxymethyl)-3-methanesulfonyl-amino-3-oxo-propyl]-amide, 116, (0.17 gm) in dry THF is added 0.3 mL HF pyridine solution. The mixture is allowed to stir for 30 min at 0 deg, then a 0.2 mL additional HF-pyridine solution is added. After further stirring for 1 h at 0 deg, the reaction mixture is poured into pH 7 phosphate buffer and extracted three times with methylene chloride. The combined organic layers are washed with satruated aqueous sodium chloride, dried over sodium sulfate powder and concentrated in vacuo. The crude product is purified over silica (7% methanol in methylene chloride) to afford the desired product.

Preparation of 7-[(naphthalene-2-carbonyl)-amino]-6-oxo-1,3,4,6,7,8,11,11a-octahydro-2H-pyrido[1,2-a]azocine-4-carboxylic acid (2-hydroxy-1-methanesulfonyl-5-oxo-pyrrolidin-3-yl)-amide (118): 7-[(Naphthalene-2-carbonyl)-amino]-6-oxo-1,3,4,6,7,8,11,11a-octahydro-2H-pyrido[1,2-a]azocine-4-carboxylic acid (1-hydroxymethyl-3-methanesulfonylamino-3-oxo-propyl)-amide, 117, (49 mg) is dissolved in 5 mL methylene chloride and cooled to 0 deg. Dess-Martin periodinane (90 mg) is added, and the reaction is strirred for 2 h at 0 deg. Saturated aqueous sodium bicarbonate solution is added and the mixture is extracted with ethyl acetate. The combined opganic layers are dried over sodium sulfate powder and the product is purified over silica (2% methanol in methylene chloride) to afford the desired product.

Another category of cysteine trap is the dicarbonyl trap wherein $R^{21}$ units comprise a unit having the formula —C(O)N($R^{21}$)$_2$, for example, —C(O)NH$_2$. α-Keto amides can be conveniently prepared from the open confirmation of the bio-active form of the aspartate trap utilizing solid state resin synthesis, for example, as disclosed in U.S. patent application Ser. No. 10/335,782 filed Jan. 2, 2003, included herein by reference.

The following scheme summarizes the synthesis of a α-keto trap from the aspartate bio-active form from the general formula of an intact analog.

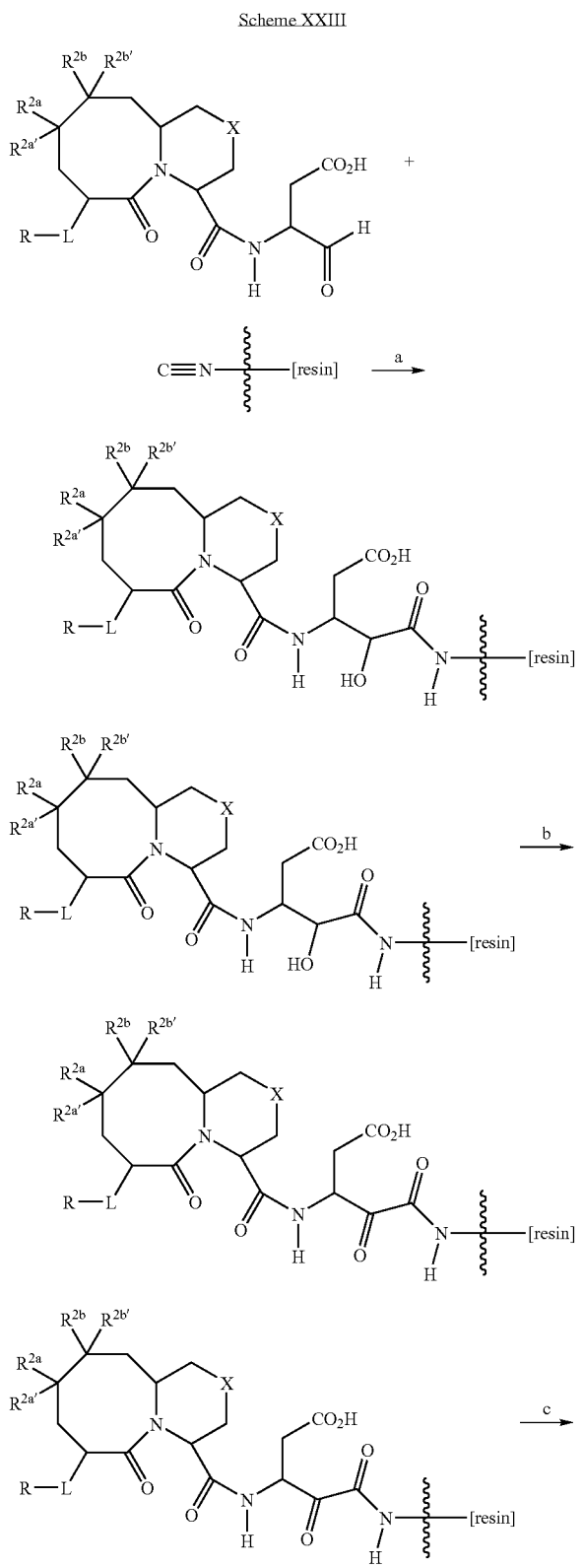

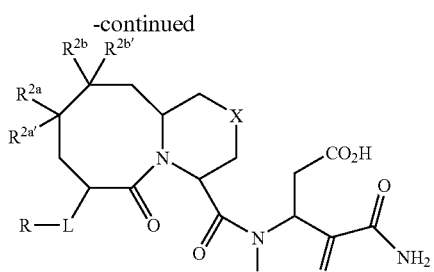

Formulations

The present invention also relates to compositions or formulations which comprise the interleukin-1β converting enzyme inhibitors according to the present invention. In general, the compositions of the present invention comprise:
 a) an effective amount of one or more interleukin-1β converting enzyme inhibitors according to the present invention; and
 b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Method of Use

The present invention also relates to methods for controlling the activity of Caspase enzymes. Caspase enzymes are responsible for mediating the extracellular release of cytokines. Because the control of Caspase enzyme activity directly affects a number of disease states and disease processes in humans and higher mammals, the present invention also comprises a method for controlling a number of diseases found to afflict humans and higher mammals.

The first aspect of the methods of the present invention relate to methods for mediating and controlling the extracellular release of the cytokine interleukin-1β. This cytokine activity is modulated by reversibly or irreversibly inhibiting interleukin-1β converting enzyme (Caspase-1, ICE). The method comprises the step of administering to a human or higher mammal an effective amount of a composition comprising one or more of the interleukin-1β converting enzyme inhibitors according to the present invention.

In a second aspect, as stated herein, Caspase-1 (ICE) is responsible for the cleavage of the inactive precursor of interleukin-1β (IL-1β) to release the active cytokine interleukin-1β. It has been discovered that Caspase-1 is localized to monocyte membranes and therefore inflammatory disorders caused by or otherwise exacerbated by the extracellular presence of the cytokine IL-1β can be treated by the inhibition of Caspase-1.[1,2] These inflammatory disorders include rheumatoid arthritis.

Regulation of the enzyme Caspase-1, (ICE) by way of administering a composition capable of reversibly or irreversibly inhibiting said enzymes, provides a method for controlling, modulating, mediating, or otherwise abating the inflammation of joints and other forms of synovial tissue associated with osteoarthritis and rheumatoid arthritis.

It is now recognized that in addition to degeneration of neurons associated with Huntington's disease, Caspase-3 expression is up-regulated in apoptotic hippocampal neurons from Alzheimer's disease patients.[3]

Regulation of the enzyme Caspase-3 by way of administering a composition capable of reversibly or irreversibly inhibiting said enzymes, provides a method for controlling, modulating, mediating, or otherwise abating the hippocampal neuron damage associated with Alzheimer's disease because of the over expression of one or more Caspase enzymes and the extracellular release of cytokines.

There is a growing preponderance of evidence to indicate that one or more Caspase enzymes are inappropriately activated in neurogenerative disorders and contribute to the death of neurons, in fact, activated Caspase-8 has been identified in degenerating neurons from Huntington's disease patients.[4] Caspase-1 has been implicated as a mediating factor in cell apoptosis. Apoptosis itself is the most common mechanism by which an organism removes unwanted or damaged cells and this ability is critically important during normal tissue development, inter alia, homeostasis, remodeling, immune response, and defense processes. Apoptosis is, therefore, implicated as contributing to several neurological disorders including Huntington's disease.[5]

Regulation of the enzyme Caspase-1, (ICE) and/or the enzyme Caspase-8, individually or collectively, by way of administering a composition capable of reversibly or irreversibly inhibiting said enzymes, provides a method for controlling, modulating, mediating, or otherwise abating the neurogenerative disorders associated with Huntington's disease.

As can be seen from the above, cell apoptosis, as well as up regulation of Caspase enzymes is a cause for not only inflammatory disease (arthritis and the like) but the degeneration of neurons and the cause of associated neurological disorders, inter alia, Parkinson's disease, Huntington's Disease and Alzheimer's disease.

The present invention therefore encompasses a method for treating separately or collectively one or more diseases, said method comprising the step of contacting a human or higher mammal with a composition comprising one or more of the Caspase inhibitors of the present invention.

As it relates to the specifically controlling the extracellular release of IL-1☐ this cytokine has been implicated as a major catabolic cytokine in the degenerative cascade leading to the loss of cartilage in osteoarthritic patients[6] and to joint inflammation and the associated pain.[7] Indeed, interleukin-1β converting enzyme (ICE) is presently the only enzyme known to be responsible for the release of interleukin-1β. This release occurs when the precursor form of interleukin-1β is converted to an active form, which is then released extracellularly. It has been discovered that the presence of joint synovitis and synovial effusion in osteoarthritic patients is the direct response to the local formation of pro-inflammatory cytokines, particularly, interleukin-1β.[8]

Osteoarthritis is a degenerative articular disorder associated with progressive structural changes in cartilage, bone and synovial tissue leading to the total loss of cartilage and joint function. It has been found that interleukin-1β is elevated in chondrocytes derived from osteoarthric joints as compared to normal non-arthritic cartilage and synovium. It has been reported that inhibition of interleukin-1β using an ICE inhibitor significantly reduces cartilage protoglycan loss in the collagen-induced arthritis model.[9]

It has now been surprisingly found that administering one or more of said compounds comprises a method for controlling or modulating the loss of cartilage in osteoarthritic patients. In addition, administering said compounds comprises a method for controlling or modulating the joint inflammation and pain associated with the swelling of tissue associated with extracellular release of cytokines.

The compounds of the present invention can be administered prophylacticly. For example, in cases wherein inflammation and cartilage damage is anticipated because of ageing or other high risk, inter alia, obesity, sports activity or which inflammation and damage is anticipated as a side effect resulting from the treatment of a more severe disease state (e.g. via chemotherapy).

Because the interleukin-1β converting enzyme inhibitors of the present invention can be delivered in a manner wherein more than one site of control can be achieved, more than one disease state can be modulated at the same time. Non-limiting examples of diseases which are affected by control or inhibition of interleukin-1β converting enzyme, thereby modulating the presence of IL-1β (excessive cytokine activity), include osteoarthritis, rheumatoid arthritis, diabetes, human Immunodeficiency virus (HIV) infection.

A method for controlling osteoarthritis in humans or higher mammals, said method comprising the step of administering to a human or higher mammal and effective amount of a composition comprising one or more of the interleukin-1β converting enzyme inhibitors The following citations footnoted herein above are included herein by reference.

1. Schreiber, R. D. et al., In *Samter's Immunologic Diseases*: Frank, M. M. et al. Eds.:Little, Brown and Co,: Boston, Mass. (1994); 279–310.
2. Ghayur T.; et al, *High Throughput Screening for Novel Anti-Inflammatories*. Khan M. (Ed.) Birkhauser Verlag Publishers, Basel, Switzerland (2000) 35–48.
3. Gervais, F. et al., *Cell* (1999), 97, 395–406.
4. Sanchez, I.; et al, *Neuron* (1999), 22, 623–633.
5. Perutz, M. F.; et al., *Trends Biochem. Sci.* (1999), 24(2) 58–63
6. J-P Pelletier et al, "Cytokines and Inflammation in Cartilage Degradation": in *Osteoarthritis, Rheumatic Disease Clinics of North America*, ed. R. W. Moskowith, (Philadelphia: W. B. Sanders, 1993), 545–568.
7. F. Fernandez-Madrid et al., "Magnetic Resonace Features of Osteoarthritis of the Knee," *J. Magn. Reson. Imaging*, 12 (1994): 703–709.
8. S. A. Stimpson et al., "Exacerbation of Arthritis by IL-1 in Rat Joints Previously Injured by Peptidoglycan-Polysaccharide," *J. Immunol.* 140 (1988): 2964–2969.
9. W. B. van den Berg et al., "Amelioration of established Murine Collagen-induced Arthritis with anti-IL-1 Treatment," *Clin. Exp. Immunol.* 95, (1994): 237–243.

Procedures

The compounds of the present invention can be evaluated for efficacy, for example, measurements of ICE inhibition constants, $K_i$, and $IC_{50}$ values can be obtained by any method chosen by the formulator. Conveniently the formulator can measure the release of, inter alia, IL-1β or cleavage of substrates by Caspace-1, Caspace-3, and Caspace-8.

THP-1 cells are human monocyte cells (mononuclear cells) which are utilized to determine in vitro cytokine inhibition. THP-1 cells, like other cell types, respond to extracellular stimulation. These stimuli include cytokines, as well as lipopolysaccharides (LPS), endotoxins, and even ultra violet light. The specific cellular response elicited by these various forms of stimuli are mediated or otherwise regulated by one or more cellular enzymes.

In the case of Caspase-1 enzyme, a signaling cascade, which includes the release of pro-inflammatory cytokines, inter alia, interleukin-1α, interleukin-1β, and TNF-α can be taken advantage of to determine the ability of chemical species to inhibit the enzyme and consequent release of said cytokines. The enzymes are themselves implicated in various disease states and processes, including cartilage degradation associated with arthritis.

One in vitro assay used to establish activity (preliminary screening) of relevant compounds of the present invention includes the following general concepts and procedures. A control sample of THP-1 cells is first stimulated to release a cytokine, in this case IL-1β, exposing the cell to LPS. The THP-1 cells which are utilized to measure suppression of cytokine release, are first incubated with the inhibitors of the present invention prior to stimulation with LPS. The supernatant from each screening sample is analyzed by standard hIL-1β ELISA protocol. The cells which remain after removal of the supernatant are treated with MTS tetrazolium to establish cell viability.

The in vitro results are reported as the $IC_{50}$, defined herein as:

$$IC_{50} = \frac{[I]}{\left[\frac{V_o}{V_i}\right] - 1}$$

wherein $V_i$ is the initial rate of substrate cleaved in the presence of the test compound at concentration [I], and $V_o$ is the rate of substrate cleavage in the control sample.

Non-limiting examples of suitable assays include:
i) UV-visible substrate enzyme assay as described by L. A I Reiter, Int. *J. Peptide Protein Res.*, 43, 87–96 (1994).
ii) Fluorescent substrate enzyme assay as described by Thornberry et al., *Nature*, 356, 768–774 (1992) and Thornberry et al., *Biochemistry*, 33, 393–3940 (1994).
iii) PBMC Cell assay as described in U.S. Pat. No. 6,204,261 B1 Batchelor et al., issued Mar. 20, 2001.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound or its enaraiomeric or diasteriomeric form or a pharmaceutically acceptable salt thereof, said compound having the formula:

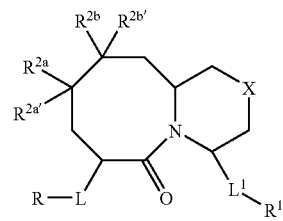

wherein R is a ring chosen from:
  i) substituted or unsubstituted $C_3$–$C_{10}$ non-aromatic carbocyclic;
  ii) substituted or unsubstituted $C_6$–$C_{10}$ aryl;
  iii) substituted or unsubstituted $C_1$–$C_{10}$ heterocyclic; and
  iv) substituted or unsubstituted $C_1$–$C_{10}$ heteroaryl;
$R^1$ is a cysteine trap;
$R^{2a}$, $R^{2a'}$, $R^{2b}$, and $R^{2b'}$ are each independently hydrogen, hydroxyl, —N(R$^6$)$_2$, halogen, $C_1$–$C_4$ alkyl, and $C_1$–$C_4$ alkoxy; or $R^{2a'}$ and $R^{2b'}$ can be taken together to form a double band;
X is —CH$_2$—, —O— or —NR$^9$—;
$R^9$ is hydrogen or a unit having the formula —L$^2$—R$^{10}$;
  $R^{10}$ is hydrogen; substituted or unsubstituted $C_1$–$C_6$ linear; branched, or cyclic hydrocarbyl; substituted or unsubstituted $C_6$–$C_{10}$ aryl; substituted or unsubstituted $C_1$–$C_9$ heterocyclic; and substituted or unsubstituted $C_1$–$C_{10}$ heteroaryl;
L, $L^1$, and $L^2$ are linking units each independently having the formula:

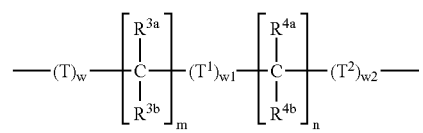

T, $T^1$, and $T^2$ are each independently selected from the group consisting of:
  i) —NR$^6$—;
  ii) —O—;
  iii) —S(O)$_2$—;
  iv) —NR$^6$S(O)$_2$—; and
  v) —S(O)$_2$NR$^6$—;
$R^6$ is hydrogen, substituted or unsubstituted $C_1$–$C_{10}$ linear, branched, or cyclic alkyl, $C_6$–$C_{10}$ aryl, and $C_7$–$C_{12}$ alkylenearyl; the indices w, w$^1$, and w$^2$ are each independently 0 or 1;
$R^{3a}$, $R^{3b}$, $R^{4a}$ and $R^{4b}$ each independently:
  i) hydrogen;
  ii) $C_1$–$C_4$ linear, branched, and cyclic alkyl;
  iii) $R^{3a}$ and $R^{3b}$ or $R^{4a}$ and $R^{4b}$ can be taken together to form a carbonyl unit; and
  iv) two $R^{3a}$ or two $R^{3b}$ units from adjacent carbon atoms or two $R^{4a}$ or two $R^{4b}$ units from adjacent carbon atoms can be taken together to form a double bond;
the index m is from 0 to 5; the index n is from 0 to 5.

2. A compound according to claim 1 comprising a scaffold having the formula:

i)
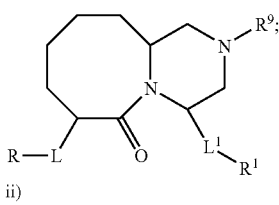

ii)
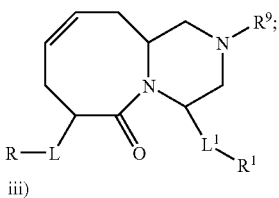

iii)
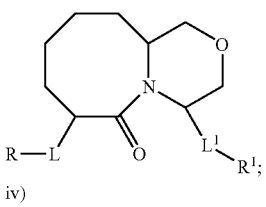

iv)
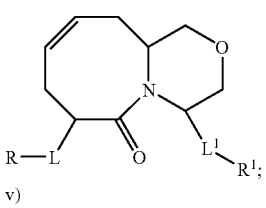

v)
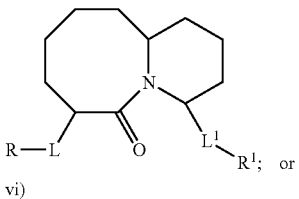

or vi)
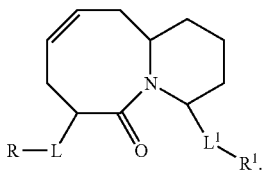

3. A compound according to claim 1 wherein $R^1$ is a reversible cysteine trap having the formula:

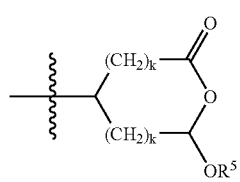

wherein $R^5$ is hydrogen; $C_1$–$C_4$ alkyl; substituted or unsubstituted $C_6$–$C_{10}$ aryl; and substituted or unsubstituted $C_7$–$C_{20}$ alkylenearyl; each index k is independently 0, 1, or 2.

4. A compound according to claim 3 wherein $R^1$ is a reversible cysteine trap having the formula:

a)
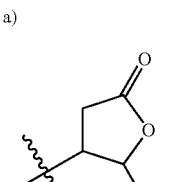

b)
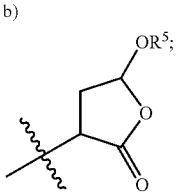

c)
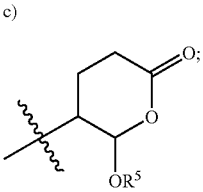

d)
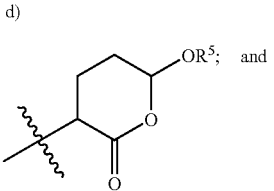

and e)
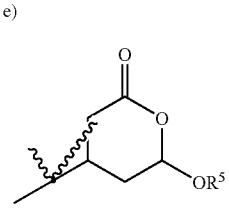

wherein $R^5$ is hydrogen, $C_1$–$C_4$ alkyl, or benzyl.

5. A compound according to claim 1 wherein $R^1$ is a reversible cysteine trap having the formula:

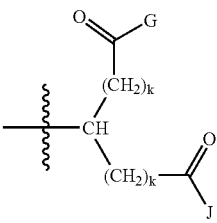

wherein G is —OH or a labile unit and J is a unit selected from the group:
i) hydrogen;
ii) substituted or unsubstituted $C_6$–$C_{10}$ aryl;
iii) substituted or unsubstituted $C_7$–$C_{20}$ alkylenearyl;

iv) substituted or unsubstituted $C_1$–$C_{10}$ heteroaryl;
v) —$CH_2N(R^{21})_2$;
vi) —$C(O)R^{21}$;
vii) —$C(O)N(R^{21})_2$; and
viii) —$C(O)OR^{21}$;

$R^{21}$ is hydrogen, substituted or unsubstituted $C_6$–$C_{10}$ aryl, substituted or unsubstituted $C_7$–$C_{20}$ alkylenearyl, and substituted or unsubstituted $C_1$–$C_{10}$ heteroaryl; each index k is independently 0, 1, or 2.

6. A compound according to claim 5 wherein $R^1$ has the formula:

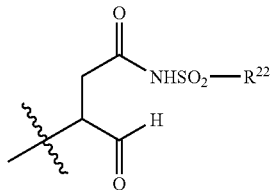

wherein $R^{22}$ is $C_1$–$C_4$ alkyl.

7. A compound according to claim 5 wherein $R^1$ has the formula:

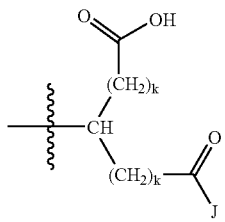

wherein J is —$(CH_2)_u R^{23}$; $R^{23}$ is a substituted or unsubstituted $C_6$–$C_{10}$ aryl; the index u is from 0 to 10.

8. A compound according to claim 7 wherein J is selected from the group consisting of benzyl, 2-phenylethyl, 3-phenylpropyl, 4-phenylbutyl, and 5-phenylpentyl.

9. A compound according to claim 5 wherein J is —$(CH_2)N(R^{21})_2$ and one $R^{21}$ is hydrogen and the other is an $C_7$–$C_{20}$ alkylenearyl unit selected from the group consisting of benzyl, 2-phenylethyl, 3-phenylpropyl, 4-phenylbutyl, and 5-phenylpentyl.

10. A compound according to claim 5 wherein J is an $C_7$–$C_{20}$ alkylenearyl unit selected from the group consisting of benzyl, 2-phenylethyl, 3-phenylpropyl, 4-phenylbutyl, and 5-phenylpentyl.

11. A compound according to claim 1 wherein $R^1$ is an α,α-difluoro ketone reversible cysteine trap having the formula:

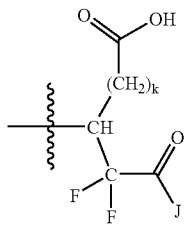

wherein J is a unit selected from the group:
i) hydrogen;
ii) substituted or unsubstituted $C_6$–$C_{10}$ aryl;
iii) substituted or unsubstituted $C_7$–$C_{20}$ alkylenearyl;
iv) substituted or unsubstituted $C_1$–$C_{10}$ heteroaryl:
v) —$CH_2N(R^{21})_2$;
vi) —$C(O)R^{21}$;
vii) —$C(O)N(R^{21})_2$; and
viii) —$C(O)OR^{21}$;

$R^{21}$ is hydrogen, substituted or unsubstituted $C_6$–$C_{10}$ aryl, substituted or unsubstituted $C_7$–$C_{20}$ alkylenearyl, and substituted or unsubstituted $C_1$–$C_{10}$ heteroaryl; each index k is independently 0, 1, or 2.

12. A compound according to claim 1 wherein $R^1$ is an irreversible cysteine trap having the formula:

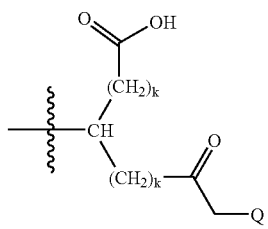

wherein Q is a leaving group selected from:
i) substituted or unsubstituted $C_2$–$C_{10}$ heterocyclic or $C_1$–$C_{10}$ heteroaryl;
ii) —$OC(O)R^{11}$;
iii) —$NHSO_2R^{12}$;
iv) —$ONR^{13}C(O)R^{13}$;
v) halogen;
vi) —$NHC(O)OR^{14}$;
vii) —$NHC(O)NHR^{15}$;
ix) —$OR^{16}$;
x) —$SR^{17}$;
xi) —$SSR^{18}$;
xii) —$SSO_3R^{19}$; and
xiii) —$OP(O)(R^{20})_2$;

wherein $R^{11}$ is $C_6$–$C_{10}$ aryl, $C_7$–$C_{20}$ alkylenearyl, —$NHR^{24}$; $R^{24}$ is $C_1$–$C_4$ alkyl; $R^{12}$ is $C_1$–$C_{12}$ linear, branched, or cyclic alkyl; $R^{13}$ is hydrogen, $C_1$–$C_4$ alkyl, substituted or unsubstituted $C_6$–$C_{10}$ aryl, substituted or unsubstituted $C_7$–$C_{20}$ alkylenearyl, or two $R^{13}$ units can be taken together to form a fused or no-fused ring having from 3 to 12 atoms; $R^{14}$ is substituted or unsubstituted $C_6$–$C_{10}$ aryl or substituted or unsubstituted $C_7$–$C_{20}$ alkylenearyl; $R^{15}$ is $C_1$–$C_4$ alkyl, substituted or unsubstituted $C_6$–$C_{10}$ aryl, and substituted or unsubstituted $C_7$–$C_{20}$ alkylenearyl; $R^{16}$ is $C_1$–$C_4$ alkyl; $R^{17}$ and $R^{18}$ are substituted or unsubstituted $C_6$–$C_{10}$ aryl, and substituted or unsubstituted $C_7$–$C_{20}$ alkylenearyl; $R^{19}$ is hydrogen, $C_1$–$C_4$ alkyl, substituted or unsubstituted $C_6$–$C_{10}$ aryl, and sublituted or unsubstituted $C_7$–$C_{20}$ alkylenearyl; $R^{20}$ is substituted or unsubstituted $C_6$–$C_{10}$ aryl, and substituted or unsubstituted $C_7$–$C_{20}$ alkylenearyl; each index k is indcpendently 0, 1, or 2.

13. A compound according to claim 12 wherein $R^1$ is a cysteine trap having the formula:

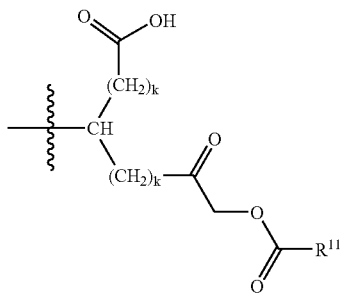

wherein $R^{11}$ is a substituted $C_6$–$C_{10}$ aryl unit.

14. A compound according to claim 13 wherein $R^{11}$ is 2,6-dimethylphenyl or 2,6-dichlorophenyl.

15. A compound according to claim 1 wherein L, $L^1$, and $L^2$ are each independently selected from the group consisting of:
 i) —C(O)NH—;
 ii) —NHC(O)—;
 iii) —NHC(O)NH—;
 iv) —C(O)C(O)—;
 v) —C(O)—;
 vi) —C(O)O—;
 vii) —OC(O)—;
 viii) —NH—;
 ix) —NHS(O)$_2$—;
 xi) —S(O)$_2$—;
 xii) and mixtures thereof.

16. A compound according to claim 1 wherein R is a substituted or unsubstituted $C_6$–$C_{10}$ aryl ring selected from the group consisting of phenyl, 2-fluorophenyl, 3-fluorophenyl, 4-fluorophenyl, 3-fluoro-4-methylphenyl, 3-fluoro-4-methoxyphenyl, 3-chloro-2-methylphenyl, 3-chloro-6-methylphenyl, 3-chloro-4-methoxyphenyl, 3-chloro-4-hydroxyphenyl, 3,5-difluorophenyl, 2,6-dichlorophenyl, 2-chlorophenyl, 3-chlorophenyl, 4-chlorophenyl, 3,4-dichlorophenyl, 3,5-dichlorophenyl, 3-chloro-4-fluorophenyl, 2-bromophenyl, 3-brornophenyl, and 4-bromophenyl.

17. A compound according to claim 1 wherein R is a substituted or unsubstituted $C_6$–$C_{10}$ aryl ring selected from the group consisting of 2-methylphenyl, 3-methylphenyl, 4-methylphenyl, 3,5-dimethylphenyl, 2-ethylphenyl, 3-ethylphenyl, 4-ethylphenyl, 3-ethyl-4-methylphenyl 3-propylphenyl, and 3-butylphenyl.

18. A compound according to claim 1 wherein R is a substituted or unsubstituted $C_6$–$C_{10}$ aryl ring selected from the group consisting of 2-methoxyphenyl, 3-methoxyphenyl, 4-methoxyphenyl, 2-ethoxyphenyl, 3-ethoxyphenyl, 4-ethoxyphenyl, 4-propoxyphenyl, 4-butoxyphenyl, and 3,4,5-trimethoxy-phenyl.

19. A compound according to claim 1 wherein R is a substituted or unsubstituted $C_6$–$C_{10}$ aryl ring selected from the group consisting of 3-aminonaphth-2-yl, 4-dimethylaminonaphth-1-yl, 2-aminophenyl, 3-aminophenyl, 4-aminophenyl, 3,4-dimethylaminophenyl, 4-amino-3-chlorophenyl, 4-amino-3,5-dichlorophenyl, 4-dimethylaminophenyl, 2-acetylaminophenyl, 3-acetylaminophenyl, 4-acetylaminophenyl, 4-isobutyrylaminophenyl, 4-propionylaminophenyl, 4-butrylaminophenyl, 4-phenylacetylaminophenyl, 3,4-diacetylaminophenyl, 4-(N-acetyl-N-methylamino)-phenyl, and 4-benzoylaminophenyl.

20. A compound according to claim 1 wherein R is a substituted or unsubstituted $C_6$–$C_{10}$ aryl ring selected from the group consisting of 2-trifluoromethylphenyl, 3-trifluoromethylphenyl, 4-trifluoromethylphenyl, 4-hydroxymethyl-phenyl, naphth-1-yl, naphth-2-yl, 4-biphenyl, 4-phenoxyphenyl, 4-(3-methyl-ureido)-phenyl, 4-sulfamoylphenyl, 3-acetylphenyl, 4-acetylphenyl, 3-hydroxyphenyl, 4-hydroxyphenyl, 4-benzyloxyphenyl, and 4-methanesulfonyl-phenyl.

21. A compound according to claim 1 wherein R is a substituted or unsubstituted $C_3$–$C_{10}$ non-aromatic carbocyclic ring selected from the group consisting of cyclopropyl, cyclobutyl, cyclohoxyl, cyclopentyl, cyclohexenyl, and cyclopentanyl.

22. A compound according to claim 1 wherein R is a substituted or unsubstituted $C_1$–$C_{10}$ heteroaryl unit selected from the group consisting of pyridin-2-yl, pyridin-3-yl, pyridin-4-yl, 3-chloropyridin-2-yl, 4-chloropyridin-2-yl, 5-chloropyridin-2-yl, 6-chloropyridin-2-yl, 3-methylpyridin-3-yl, 4-methylpyridin-3-yl, 5-methylpyridin-3-yl, vinyl pyridin-4-yl, and vinyl pyridin-3-yl.

23. A compound according to claim 1 wherein R is a substituted or unsubstituted $C_1$–$C_{10}$ heteroaryl unit selected from the group consisting of thiophen-3-yl, thiophen-2-yl, pyrimidin-2-yl, pyrimidin-4-yl, pyrimidin-5-yl, 2-isobutoxy-pyrimidin-4-yl, 2-isobutylaminopyriniidin-4-yl, 2-phenoxypyrimidin-4-yl, 2-ethyl-5-methyl-2H-pyrazol-3-yl, 2,4-dimethyl-thiazol-5-yl, 5-methyl-isoxazol-3-yl, 1H-imidazol-2-yl, [1,2,3]thiadiazol-5-yl, furan-2-yl, furan-3-yl, 4,5-dimethyl-2-furanyl, 5-bromo-2-furanyl, and 2-(phenylamino)pyrimidin-4-yl.

24. A compound according to claim 1 wherein R is a substituted or unsubstituted $C_1$–$C_{10}$ heteroaryl ring selected from the group consisting of quinolin-2-yl, quinolin-3-yl, quinolin-4-yl, quinolin-5-yl, quinolin-8-yl, quinolin-1-yl, isoquinolin-3-yl, 1,2,3,4-tetrahydro-quinolin-2-yl, 1,2,3,4-tetrahydro-isoquinolin-3-yl, benzofuran-2-yl, benzofuran-3-yl, benzofuran-5-yl, 1H-indol-5-yl, benzo[b]thiophen-5-yl, benzo[b]thiophen-3-yl, benzo[b]thiophen-2-yl, 3H-benzotriazol-5-yl, 1-methyl-1H-indol-2-yl, 3H-benzimidazol-5-yl, 4-methoxy-quinolin-2-yl, and thieno[2,3-b]thiophen-2-yl.

25. A compound according to claim 1 wherein R is a substituted or unsubstituted $C_1$–$C_{10}$ heterocyclic ring selected from the group consisting of pyrrolidin-1-yl, piperidin-1-yl, piperidin-4-yl, and piperazin-1-yl.

26. A compound according to claim 1 wherein X is —$NR^9$—; and $R^9$ is hydrogen or $C_1$–$C_4$ linear, branched, or cyclic alkyl.

27. A compound according to claim 1 wherein X is —N($L^2$—$R^{10}$)—; $L^2$ in a unit selected from the group consisting of:
 i) —C(O)O—;
 ii) —C(O)—; and
 iii) —S(O)$_2$—;
 $R^{10}$ is hydrogen, methyl, ethyl, isopropyl, phenyl, benzyl, and phenylamino.

28. A compound according to claim 1 wherein X is —O—.

29. A compound according to claim 1 wherein X is $CH_2$—.

30. A compound according to claim 1 having the formula:

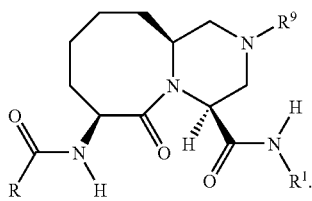

31. A compound according to claim 30 wherein $R^1$ has the formula:

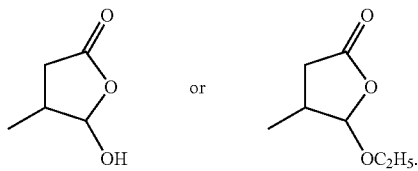

32. A compound according to claim 30 wherein R is a substituted or unsubstituted $C_6$–$C_{10}$ aryl ring selected from the group consisting of phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 2-methoxyphenyl, 3-methoxy-phenyl, 4-methoxyphenyl, 2-trifluoro-methylphenyl, 3-trifluoromethylphenyl, 4-trifluoromethylphenyl, 3,4,5-trimethoxy-phenyl, naphth-1-yl, and naphth-2-yl.

33. A compound according to claim 30 wherein R is a substituted or unsubstiruted $C_1$–$C_{10}$ heteroaryl ring selected from the group consisting of pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, quinolin-2-yl, quinolin-3-yl, quinolin-4-yl, isoquinolin-1-yl, isoquinolin-3-yl, 1,2,3,4-tetrahydro-quinolin-2-yl, 1,2,3,4-tetrahydroquinolin-3-yl, pyridin-2-yl, pyridin-3-yl, pyridin4-yl, and benzo[b]thiophen-2-yl.

34. A compound according to claim 30 wherein $R^9$—$L^2$—$R^{10}$, said $L^2$—$R^{10}$ is selected from the group consisting of hydrogen, —$CH_3$, —$CH_2CH_3$, —$C(O)CH_3$, —$SO_2CH_3$, —$SO_2CH_3CH_3$, —$SO_3CH_3(CH_3)_2$, —$SO_2C_6H_5$, —$C(O)C_6H_5$, —$C(O)NHC_6H_5$, and —$C(O)OCH_2C_6H_5$.

35. A compound selected from the group consisting of;
(4S,6S,10aS)-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-acetyl-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-2-acetyl-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-methyl-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-2-methyl-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-ethyl-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-2-ethyl-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-methanesulfonyl-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-2-methanesulfonyl-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-ethanesulfonyl-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-2-ethanesulfonyl-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-propanesulfonyl-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-2-propanesulfonyl-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-benzenesulfonyl-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-2-benzenesulfonyl-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-benzoyl-6-benzoylamino-5-oxo-decahydro-2,4a-diaza-benzocyclooctene-4-carboxylic acid (2-hydroxy-5-oxo-tetrahydrofuran-3-yl)amide;
(4S,6S,10aS)-2-benzoyl-6-benzoylamino-5-oxo-decahydro-2,4a-diaza-benzocyclooctene-4-carboxylic acid (2-ethoxy-5-oxo-tetrahydrofuran-3-yl)amide;
(4S,6S,10aS)-2-carbobenzoxy-6-benzoylamino-5-oxo-decahydro-2,4a-diaza-benzocyclooctene-4-carboxylic acid (2-hydroxy-5-oxo-tetrahydrofuran-3-yl)amide; and
(4S,6S,10aS)-2-carbobenzoxy-6-benzoylamino-5-oxo-decahydro-2,4a-diaza-benzocyclooctene-4-carboxylic acid (2-ethoxy-5-oxo-tetrahydrofuran-3-yl)amide.

36. A compound selected from the group consisting of;
(4S,6S,10aS)-6-(naphthalene-1-carbonyl)amino5-oxo-decahydro-2,4a-diaza-benzocyclooctene-4-carboxylic acid (2-hydroxy-5-oxo-tetrahydrofuran-3-yl)amide;
(4S,6S,10aS)-6-(naphthalene-1-carbonyl)amino5-oxo-decahydro-2,4a-diaza-benzocyclooctene-4-carboxylic acid (2-ethoxy-5-oxo-tetrahydrofuran-3-yl)amide;
(4S,6S,10aS)-2-acetyl-6-(naphthalene-1-carbonyl)amino5-oxo-decahydro-2,4a-diaza-benzocyclooctene-4-carboxylic acid (2-hydroxy-5-oxo-tetrahydrofuran-3-yl)amide;
(4S,6S,10aS)-2-acetyl-6-(naphthalene-1-carbonyl)amino5-oxo-decahydro-2,4a-diaza-benzocyclooctene-4-carboxylic acid (2-ethoxy-5-oxo-tetrahydrofuran-3-yl)amide;
(4S,6S,10aS)-2-methyl-6-(naphthalene-1-carbonyl)amino5-oxo-decahydro-2,4a-diaza-benzocyclooctene-4-carboxylic acid (2-hydroxy-5-oxo-tetrahydrofuran-3-yl)amide;
(4S,6S,10aS)-2-methyl-6-(naphthalene-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-ethyl-6-(naphthalene-1-carbonyl) amino5-oxo-decahydro-2,4a-diaza-benzocyclooctene-4-carboxylic acid (2-hydroxy-5-oxo-tetrahydrofuran-3-yl)amide;

(4S,6S,10aS)-2-ethyl-6-(naphthalene-1-carbonyl) amino5-oxo-decahydro-2,4a-diaza-benzocyclooctene-4-carboxylic acid (2-ethoxy-5-oxo-tetrahydrofuran-3-yl)amide;

(4S,6S,10aS)-2-methanesulfonyl-6-(naphthalene-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-2-methanesulfonyl-6-(naphthalene-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-ethanesulfonyl-6-(naphthalene-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-2-ethanesulfonyl-6-(naphthalene-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-propanesulfonyl-6-(naphthalene-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-2-propanesulfonyl-6-(naphthalene-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-benzenesulfonyl-6-(naphthalene-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-2-benzenesulfonyl-6-(naphthalene-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-benzoyl-6-(naphthalene-1-carbonyl) amino5-oxo-decahydro-2,4a-diaza-benzocyclooctene-4-carboxylic acid (2-hydroxy-5-oxo-tetrahydrofuran-3-yl)amide;

(4S,6S,10aS)-2-benzoyl-6-(naphthalene-1-carbonyl) amino5-oxo-decahydro-2,4a-diaza-benzocyclooctene-4-carboxylic acid (2-ethoxy-5-oxo-tetrahydrofuran-3-yl)amide;

(4S,6S,10aS)-2-carbobenzoxy-6-(naphthalene-1-carbonyl)amino5-oxo-decahydro-2,4a-diaza-benzocyclooctene-4-carboxylic acid (2-hydroxy-5-oxo-tetrahydrofuran-3-yl)amide; and (4S,6S,10aS)-2-carbobenzoxy-6-(naphthalene-1-carbonyl)amino5-oxo-decahydro-2,4a-diaza-benzocyclooctene-4-carboxylic acid (2-ethoxy-5-oxo-tetrahydrofuran-3-yl)amide.

37. A compound selected from the group consisting of;

(4S,6S,10aS)-6-(isoquinoline-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-6-(isoquinoline-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-acetyl-6-(isoquinoline-1-carbonyl) amino5-oxo-decahydro-2,4a-diaza-benzocyclooctene-4-carboxylic acid (2-hydroxy-5-oxo-tetrahydrofuran-3-yl)amide;

(4S,6S,10aS)-2-acetyl-6-(isoquinoline-1-carbonyl) amino5-oxo-decahydro-2,4a-diaza-benzocyclooctene-4-carboxylic acid (2-ethoxy-5-oxo-tetrahydrofuran-3-yl)amide;

(4S,6S,10aS)-2-methyl-6-(isoquinoline-1-carbonyl) amino5-oxo-decahydro-2,4a-diaza-benzocyclooctene-4-carboxylic acid (2-hydroxy-5-oxo-tetrahydrofuran-3-yl)amide;

(4S,6S,10aS)-2-methyl-6-(isoquinoline-1-carbonyl) amino5-oxo-decahydro-2,4a-diaza-benzocyclooctene-4-carboxylic acid (2-ethoxy-5-oxo-tetrahydrofuran-3-yl)amide;

(4S,6S,10aS)-2-ethyl-6-(isoquinoline-1-carbonyl) amino5-oxo-decahydro-2,4a-diaza-benzocyclooctene-4-carboxylic acid (2-hydroxy-5-oxo-tetrahydrofuran-3-yl)amide;

(4S,6S,10aS)-2-ethyl-6-(isoquinoline-1-carbonyl) amino5-oxo-decahydro-2,4a-diaza-benzocyclooctene-4-carboxylic acid (2-ethoxy-5-oxo-tetrahydrofuran-3-yl)amide;

(4S,6S,10aS)-2-methanesulfonyl-6-(isoquinoline-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-2-methanesulfonyl-6-(isoquinoline-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-ethanesulfonyl-6-(isoquinoline-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-2-ethanesulfonyl-6-(isoquinoline-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-propanesulfonyl-6-(isoquinoline-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-2-propanesulfonyl-6-(isoquinoline-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-benzenesulfonyl-6-(isoquinoline-1-carbonyl)amino5-oxo-decahydro-2,4a-diaza-benzocyclooctene-4-carboxylic acid (2-hydroxy-5-oxo-tetrahydrofuran-3-yl)amide;

(4S,6S,10aS)-2-benzenesulfonyl-6-(isoquinoline-1-carbonyl)amino5-oxo-decahydro-2,4a-diaza-benzocyclooctene-4-carboxylic acid (2-ethoxy-5-oxo-tetrahydrofuran-3-yl)amide;

(4S,6S,10aS)-2-benzoyl-6-(isoquinoline-1-carbonyl) amino5-oxo-decahydro-2,4a-diaza-benzocyclooctene-4-carboxylic acid (2-hydroxy-5-oxo-tetrahydrofuran-3-yl)amide;

(4S,6S,10aS)-2-benzoyl-6-(isoquinoline-1-carbonyl) amino5-oxo-decahydro-2,4a-diaza-benzocyclooctene-4-carboxylic acid (2-ethoxy-5-oxo-tetrahydrofuran-3-yl)amide;

(4S,6S,10aS)-2-carbobenzoxy-6-(isoquinoline-1-carbonyl)amino5-oxo-decahydro-2,4a-diaza-benzocyclooctene-4-carboxylic acid (2-hydroxy-5-oxo-tetrahydrofuran-3-yl)amide; and (4S,6S,10aS)-2-carbobenzoxy-6-(isoquinoline-1-carbonyl)amino5-oxo-decahydro-2,4a-diaza-benzocyclooctene-4-carboxylic acid (2-ethoxy-5-oxo-tetrahydrofuran-3-yl)amide.

38. A compound according to claim 1 having the formula:

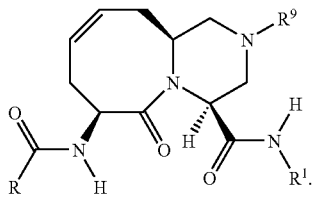

39. A compound according to claim 38 wherein $R^1$ has the formula:

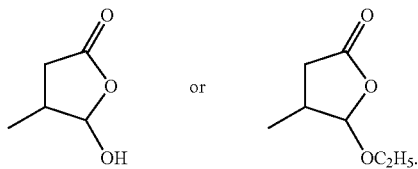

40. A compound according to claim 38 wherein R is a substituted or unsubstituted $C_6$–$C_{10}$ aryl ring selected from the group consisting of phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 2-methoxyphenyl, 3-methoxy-phenyl, 4-methoxyphenyl, 2-trifluoro-methylphenyl, 3-trifluoroniethylphenyl, 4-trifluoromethylphenyl, 3,4,5-trimethoxy-phenyl, naphth-1-yl, and naphth-2-yl.

41. A compound according to claim 38 wherein R is a substituted or unsubstituted $C_1$–$C_{10}$ heteroaryl ring selected from the group consisting of pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, quinolin-2-yl, quinolin-3-yl, quinolin-4-yl, isoquinolin-1-yl, isoquinolin-3-yl, 1,2,3,4-tetrahydro-quinolin-2-yl, 1,2,3,4-tetrahydroquinolin-3-yl, pyridin-2-yl, pyridin-3-yl, pyridin-4-yl, and benzo[b]thiophen-2-yl.

42. A compound according to claim 38 wherein $R^9$ is —$L^2$—$R^2$, said $L^2$—$R^2$ is selected from the group consisting of hydrogen, —$CH_3$, —$CH_2CH_3$, —$C(O)CH_3$, —$SO_2CH_3$, —$SO_2CH_2CH_3$, —$SO_2CH(CH_3)_2$, —$SO_2C_6H_5$, —$C(O)C_6H_5$, —$C(O)NHCC_6H_5$, and —$C(O)OCH_2C_6H_5$.

43. A compound selected from the group consisting of;

(4S,6S,10aS)-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-acetyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-acetyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-methyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-methyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-ethyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-ethyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-methanesulfonyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-methanesulfonyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-ethanesulfonyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-ethanesulfonyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-propanesulfonyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-propanesulfonyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-benzenesulfonyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-benzenesulfonyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-benzoyl-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-benzoyl-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-carbobenzoxy-6-benzoylamino-5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide; and (4S,6S,10aS)-2-carbobenzoxy-6-benzoylamino-5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide.

44. A compound selected from the group consisting of;
(4S,6S,10aS)-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-acetyl-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-acetyl-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-methyl-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-methyl-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-ethyl-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-ethyl-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-methanesulfonyl-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-methanesulfonyl-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-ethanesulfonyl-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-ethanesulfonyl-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-propanesulfonyl-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-propanesulfonyl-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-benzenesulfonyl-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-benzenesulfonyl-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-benzoyl-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-benzoyl-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-carbobenzoxy-6-(naphthalene-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide; and
(4S,6S,10aS)-2-carbobenzoxy-6-(naphthalene-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide.

45. A compound selected from the group consisting of;
(4S,6S,10aS)-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-acetyl-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-acetyl-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-methyl-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-methyl-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-ethyl-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-ethyl-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-methanesulfonyl-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-methanesulfonyl-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;
(4S,6S,10aS)-2-ethanesulfonyl-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;
(4S,6S,10aS)-2-ethanesulfonyl-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-propanesulfonyl-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-propanesulfonyl-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-benzenesulfonyl-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-benzenesulfonyl-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-benzoyl-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide;

(4S,6S,10aS)-2-benzoyl-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide;

(4S,6S,10aS)-2-carbobenzoxy-6-(isoquinoline-1-carbonyl)amino5-oxo-1,3,4,5,6,7,10,10a-octahydro-2H-2,4a-diaza-benzocyclooctene-4-carboxylic acid (2-hydroxy-5-oxo-tetrahydrofuran-3-yl)amide; and (4S,6S,10aS)-2-carbobenzoxy-6-(isoquinoline-1-carbonyl)amino5-oxo-1,3,4,5,6,7,10,10a-octahydro-2H-2,4a-diaza-benzocyclooctene-4-carboxylic acid (2-ethoxy-5-oxo-tetrahydrofuran-3-yl)amide.

46. A compound according to claim 1 having the formula:

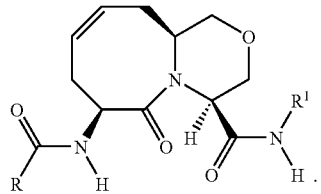

47. A compound according to claim 46 wherein $R^1$ has the formula:

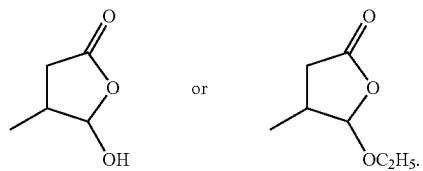

48. A compound according to claim 46 wherein R is a substituted or unsubstituted $C_6$–$C_{10}$ aryl ring selected from the group consisting of phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 2-methoxyphenyl, 3-methoxy-phenyl, 4-methoxyphenyl, 2-trifluoro-methylphenyl, 3-trifhioromethylphenyl, 4-trifluoromethylphenyl, 3,4,5-trimethoxy-phenyl, naphth-1-yl, and naphth-2-yl.

49. A compound according to claim 46 wherein R is a substituted or unsubstituted $C_1$–$C_{10}$ heteroaryl ring selected from the group consisting of pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, quinolin-2-yl, quinolin-3-yl, quinolin-4-yl, isoquinolin-1-yl, isoquinolin-3-yl, 1,2,3,4-tetrahydro-quinolin-2-yl, 1,2,3,4-tetrahydroquinolin-3-yl, pyridin-2-yl, pyridin-3-yl, pyridin-4-yl, and benzo[b]thiophen-2-yl.

50. A compound selected from the group consisting of:

(4S,6S,10aS)-6-Isoquinoline-1-carbonyl)amino]-5-oxo-1,3,4,5,6,7,10,10a-octahydro-2-oxo-[4a]-azabenzocyclooctene-4-carboxylic acid (2-ethoxy-5-oxo-tetrahydrofuran-3-yl)amide;

(4S,6S,10aS)-6-Isoquinoline-1-carbonyl)amino]-5-oxo-1,3,4,5,6,7,10,10a-octahydro-2-oxo-[4a]-azabenzocyclooctene-4-carboxylic acid (2-ethoxy-5-oxo-tetrahydrofuran-3-yl)amide;

(4S,6S,10aS)-6-[(2-chlorophenyl)amino]-5-oxo-1,3,4,5,6,7,10,10a-octahydro-2-oxo-[4a]-aza-benzocyclooctene-4-carboxylic acid (2-hydroxy-5-oxo-tetrahydro-furan-3-yl)-amide;

(4S,6S,10aS)-6-[(3-chlorophenyl)amino]-5-oxo-1,3,4,5,6,7,10,10a-octahydro-2-oxo-[4a]-aza-benzocyclooctene-4-carboxylic acid (2-hydroxy-5-oxo-tetrahydro-furan-3-yl)-amide;

(4S,6S,10aS)-6-[(4-chlorophenyl)amino]-5-oxo-1,3,4,5,6,7,10,10a-octahydro-2-oxo-[4a]-aza-benzocyclooctene-4-carboxylic acid (2-hydroxy-5-oxo-tetrahydro-furan-3-yl)-amide;

(4S,6S,10aS)-6-[(2-trifluoromethylphenyl)amino]-5-oxo-1,3,4,5,6,7,10,10a-octahydro-2-oxo-[4a]-aza-benzocyclooctene-4-carboxylic acid (2-hydroxy-5-oxo-tetrahydro-furan-3-yl)-amide;

(4S,6S,10aS)-6-[(3-trifluoromethylphenyl)amino]-5-oxo-1,3,4,5,6,7,10,10a-octahydro-2-oxo-[4a]-aza-benzocyclooctene-4-carboxylic acid (2-hydroxy-5-oxo-tetrahydro-furan-3-yl)-amide;

(4S,6S,10aS)-6-[(4-trifluoromethylphenyl)amino]-5-oxo-1,3,4,5,6,7,10,10a-octahydro-2-oxo-[4a]-aza-benzocyclooctene-4-carboxylic acid (2-hydroxy-5-oxo-tetrahydro-furan-3-yl)-amide;

(4S,6S,10aS)-6-[(Naphthalene-2-carbonyl)-amino]-5-oxo-1,3,4,5,6,7,10,10a-octahydro-2-oxo-4a-aza-benzocyclooctene-4-carboxylic acid (2-hydroxy-5-oxo-tetrahydro-furan-3-yl)-amide;

(4S,6S,10aS)-6-[(Benzo[b]thiophene-2-carbonyl)-amino]-5-oxo-1,3,4,5,6,7,10,10a-octahydro-2-oxo-4a-aza-benzocyclooctene-4-carboxylic acid (2-hydroxy-5-oxo-tetrahydro-furan-3-yl)-amide;

(4S,6S,10aS)-6-{[3-(4-Chlorophenyl)-5-methyl-ioxazole-4-carbonyl]-amino}-5-oxo-1,3,4,5,6,7,10,10a-octahydro-2-oxo-4a-aza-benzocyclooctene-4-carboxylic acid (2-hydroxy-5-oxo-tetrahydro-furan-3-yl)-amide;

(4S,6S,10aS)-6-(3-Fluorobenzoylamino)-5-oxo-1,3,4,5,6,7,10,10a-octahydro-2-oxa-4a-aza-benzocyclooctene-4-carboxylic acid (2-hydroxy-5-oxo-tetrahydro-fuan-3-yl)-amide;

(4S,6S,10aS)-6-(4-Fluorobenzoylamino)-5-oxo-1,3,4,5,6,7,10,10a-octahydro-2-oxa-4a-aza-benzocyclooctene-4-carboxylic acid (2-hydroxy-5-oxo-tetrahydro-fuan-3-yl)-amide;

(4S,6S,10aS)-5-Oxo-6-[(quinoxaline-2-carbonyl)-amino]-1,3,4,5,6,7,10,10a-octahydro-2-oxa-4a-aza-benzocyclooctene-4-carboxylic acid (2-hydroxy-5-oxo-tetrahydro-furan-3-yl-amide; and (4S,6S,10aS)-6-Benzoylamino-5-oxo-1,3,4,5,6,7,10,10a-octahydro-2-oxa-4a-aza-benzocyclooctene-4-carboxylic acid (2-hydroxy-5-oxo-tetrahydro-furan-3-yl)-amide.

51. A compound according to claim 1 having the formula:

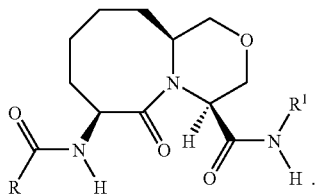

52. A compound according to claim 51 wherein R¹ has the formula:

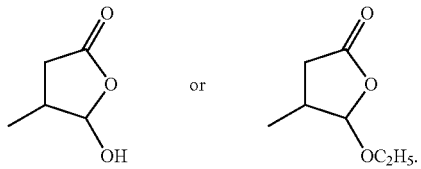

53. A compound according to claim 51 wherein R is a substituted or unsubstituted $C_6$–$C_{10}$ aryl ring selected from the group consisting of phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 2-methoxy-phenyl, 3-methoxy-phenyl, 4-methoxyphenyl, 2-trifluoro-methylphenyl, 3-trifluoromethylphenyl, 4-trifluoromethylphenyl, 3,4,5-trimethoxy-phenyl, naphth-1-yl, and naphth-2-yl.

54. A compound according to claim 51 wherein R is a substituted or unsubstituted $C_1$–$C_{10}$ heteroaryl ring selected from the group consisting of pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, quinolin-2-yl, quinolin-3-yl, quinolin-4-yl, isoquinolin-1-yl, isoquinolin-3-yl, 1,2,3,4-tetrahydro-quinolin-2-yl, 1,2,3,4-tetrahydro-quinolin-3-yl, pyridin-2-yl, pyridin-3-yl, pyridin-4-yl, and benzo[b]thiophen-2-yl.

55. A compound selected from the group consisting of:
(4S,6S,10aS)-6-Isoquinoline-1-carbonyl)amino]-5-oxo-decahydro-2-oxo-[4a]-azabenzocyclooctene-4-carboxylic acid (2-ethoxy-5-oxo-tetrahydrofuran-3-yl) amide;
(4S,6S,10aS)-6-Isoquinoline-1-carbonyl)amino]-5-oxo-decahydro-2-oxo-[4a]-azabenzocyclooctene-4-carboxylic acid (2-ethoxy-5-oxo-tetrahydrofuran-3-yl) amide;
(4S,6S,10aS)-6-[(2-chlorophenyl)amino]-5-oxo-decahydro-2-oxa-[4a]-aza-benzocyclooctene-4-carboxylic acid (2-hydroxy-5-oxo-tetrahydro-furan-3-yl)-amide;
(4S,6S,10aS)-6-[(3-chlorophenyl)amino]-5-oxo-decahydro-2-oxa-[4a]-aza-benzocyclooctene-4-carboxylic acid (2-hydroxy-5-oxo-tetrahydro-furan-3-yl)-amide;
(4S,6S,10aS)-6-[(4-chlorophenyl)amino]-5-oxo-decahydro-2-oxa-[4a]-aza-benzocyclooctene-4-carboxylic acid (2-hydroxy-5-oxo-tetrahydro-furan-3-yl)-amide;
(4S,6S,10aS)-6-[(2-trifluoromethylphenyl)amino]-5-oxo-decahydro-2-oxa-[4a]-aza-benzocyclooctene-4-carboxylic acid (2-hydroxy-5-oxo-tetrahydro-furan-3-yl)-amide;
(4S,6S,10aS)-6-[(3-trifluoromethylphenyl)amino]-5-oxo-decahydro-2-oxa-[4a]-aza-benzocyclooctene-4-carboxylic acid (2-hydroxy-5-oxo-tetrahydro-furan-3-yl)-amide;
(4S,6S,10aS)-6-[(4-trifluoromethylphenyl)amino]-5-oxo-decahydro-2-oxa-[4a]-aza-benzocyclooctene-4-carboxylic acid (2-hydroxy-5-oxo-tetrahydro-furan-3-yl)-amide;
(4S,6S,10aS)-6-[(Naphthalene-2-carbonyl)-amino]-5-oxo-decahydro-2-oxa-4a-aza-benzocyclooctene-4-carboxylic acid (2-hydroxy-5-oxo-tetrahydro-furan-3-yl)-amide;
(4S,6S,10aS)-6-[(Benzo[b]thiophene-2-carbonyl)-amino]-5-oxo-decahydro-2-oxa-4a-aza-benzocyclooctene-4-carboxylic acid (2-hydroxy-5-oxo-tetrahydro-furan-3-yl)-amide;
(4S,6S,10aS)-6-{[3-(4-Chlorophenyl)-5-methyl-ioxazole-4-carbonyl]-amino}-5-oxo-decahydro-2-oxa-4a-aza-benzocyclooctene-4-carboxylic acid (2-hydroxy-5-oxo-tetrahydro-furan-3-yl)-amide;
(4S,6S,10aS)-6-(3-Fluorobenzoylamino)-5-oxo-decahydro-2-oxa-4a-aza-benzocyclooctene-4-carboxylic acid (2-hydroxy-5-oxo-tetrahydro-fuan-3-yl)-amide;
(4S,6S,10aS)-6-(4-Fluorobenzoylamino)-5-oxo-decahydro-2-oxa-4a-aza-benzocyclooctene-4-carboxylic acid (2-hydroxy-5-oxo-tetrahydro-fuan-3-yl)-amide;
(4S,6S,10aS)-5-Oxo-6-[(quinoxaline-2-carbonyl)-amino]-decahydro-2-oxa-4a-aza-benzocyclooctene-4-carboxylic acid (2-hydroxy-5-oxo-tetrahydro-furan-3-yl-amide; and
(4S,6S,10aS)-6-Benzoylamino-5-oxo-decahydro-2-oxa-4a-aza-benzocyclooctene-4-carboxylic acid (2-hydroxy-5-oxo-tetrahydro-furan-3-yl)-amide.

56. A compound according to claim 1 having the formula:

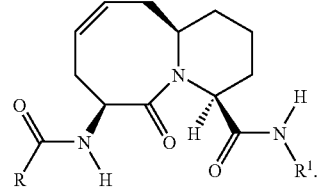

57. A compound according to claim 56 wherein R¹ has the formula:

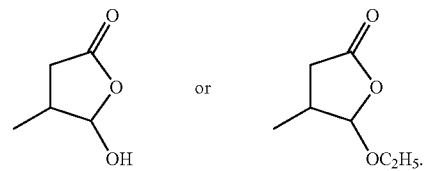

58. A compound according to claim 56 wherein R is a substituted or unsubstituted $C_6$–$C_{10}$ aryl ring selected from the group consisting of phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 2-methoxy-phenyl, 3-methoxy-phenyl, 4-methoxyphenyl, 2-trifluoro-methylphenyl, 3-trifluoromethylphenyl, 4-trifluoromethylphenyl, 3,4,5-trimethoxy-phenyl, naphth-1-yl, and naphth-2-yl.

59. A compound according to claim 56 wherein R is a substituted or unsubstituted $C_1$–$C_{10}$ heteroaryl ring selected from the group consisting of pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, quinolin-2-yl, quinolin-3-yl, quinolin-4-yl, isoquinolin-1-yl, isoquinolin-3-yl, 1,2,3,4-tetrahydro-quinolin-2-yl, 1,2,3,4-tetrahydro-quinolin-3-yl, pyridin-2-yl, pyridin-3-yl, pyridin-4-yl, and benzo[b]thiophen-2-yl.

60. A compound selected from the group consisting of:
(4S,7S,11aR)-7-benzoylamino-6-oxo-1,3,4,6,7,8,11,11a-octahydro-2H-pyrido[1,2-a]azocine-4-carboxylic acid (2-ethoxy-5-oxo-tetrahydro-furan-3-yl)-amide;
(4S,7S,11aR)-7-Benzoylamino-6-oxo-1,3,4,6,7,8,11,11a-octahydro-2H-pyrido[1,2-a]azocine-4-carboxylic acid (2-hydroxy-5-oxo-tetrahydrofuran-3-yl)-amide;
(4S,7S,11aR)-7-[(Isoquinoline-1-carbonyl)-amino]-6-oxo-1,3,4,6,7,8,11,11a-octahydro-2H-pyrido[1,2-a]azocine-4-carboxylic acid (2-hydroxy-5-oxo-tetrahydrofuran-3-yl)-amide;
(4S,7S,11aR)-6-Oxo-7-(3-phenyl-ureido)-1,3,4,6,7,8,11,11a-octahydro-2H-pyrido[1,2-a]azocine-4-carboxylic acid (2-hydroxy-5-oxo-tetrahydro-furan-3-yl)-amide;
(4S,7S,11aR)-7-(3-Chloro-benzoylamino)-6-oxo-1,3,4,6,7,8,11,11a-octahydro-2H-pyrido[1,2-a]azocine-4-carboxylic acid (2-hydroxy-5-oxo-tetrahydro-furan-3-yl)-amide;
(4S,7S,11aR)-6-Oxo-7-(3-trifluoromethyl-benzoylamino)-1,3,4,6,7,8,11,11a-octahydro-2H-pyrido[1,2-a]azocine-4-carboxylic acid (2-hydroxy-5-oxo-tetrahydro-furan-3-yl)-amide;
(4S,7S,11aR)-7-[(Benzo[b]thiophene-2-carbonyl)-amino]-6-oxo-1,3,4,6,7,8,11,11a-octahydro-2H-pyrido[1,2-a]azocine-4-carboxylic acid (2-hydroxy-5-oxo-tetrahydro-furan-3-yl)-amide;
(4S,7S,11aR)-7-[(Naphthalene-2-carbonyl)-amino]-6-oxo-1,3,4,6,7,8,11,11a-octahydro-2H-pyrido[1,2-a]azocine-4-carboxylic acid (2-hydroxy-5-oxo-tetrahydro-furan-3-yl)-amide;
(4S,7S,11aR)-7-[(Isoquinoline-1-carbonyl)-amino]-6-oxo-1,3,4,6,7,8,11,11a-octahydro-2H-pyrido[1,2-a]azocine-4-carboxylic acid (2-ethoxy-5-oxo-tetrahydrofuran-3-yl)-amide;
(4S,7S,11aR)-6-Oxo-7-(3-phenyl-ureido)-1,3,4,6,7,8,11,11a-1,3,4,6,7,8,11,11a-octahydro-2H-pyrido[1,2-a]azocine-4-carboxylic acid (2-ethoxy-5-oxo-tetrahydro-furan-3-yl)-amide;
(4S,7S,11aR)-7-(3-Chloro-benzoylamino)-6-oxo-1,3,4,6,7,8,11,11a-octahydro-2H-pyrido[1,2-a]azocine-4-carboxylic acid (2-ethoxy-5-oxo-tetrahydro-furan-3-yl)-amide;
(4S,7S,11aR)-6-Oxo-7-(3-trifluoromethyl-benzoylamino)-1,3,4,6,7,8,11,11a-octahydro-2H-pyrido[1,2-a]azocine-4-carboxylic acid (2-ethoxy-5-oxo-tetrahydro-furan-3-yl)-amide;
(4S,7S,11aR)-7-[(Benzo[b]thiophene-2-carbonyl)-amino]-6-oxo-1,3,4,6,7,8,11,11a-octahydro-2H-pyrido[1,2-a]azocine-4-carboxylic acid (2-ethoxy-5-oxo-tetrahydro-furan-3-yl)-amide; and
(4S,7S,11aR)-7-[(Naphthalene-2-carbonyl)-amino]-6-oxo-1,3,4,6,7,8,11,11a-octahydro-2H-pyrido[1,2-a]azocine-4-carboxylic acid (2-ethoxy-5-oxo-tetrahydro-furan-3-yl)-amide.

61. A compound according to claim 1 having the formula:

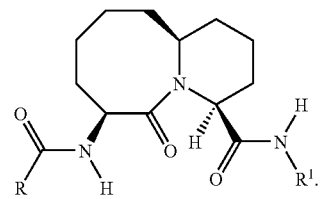

62. A compound according to claim 61 wherein $R^1$ has the formula:

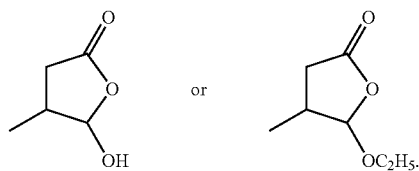

63. A compound according to claim 61 wherein R is a substituted or unsubstituted $C_6$–$C_{10}$ aryl ring selected from the group consisting of phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 2-methoxy-phenyl, 3-methoxy-phenyl, 4-methoxyphenyl, 2-trifluoro-methylphenyl, 3-trifluoromethylphenyl, 4-trifluoromethylphenyl, 3,4,5-trimethoxy-phenyl, naphth-1-yl, and naphth-2-yl.

64. A compound according to claim 61 wherein R is a substituted or unsubstituted $C_1$–$C_{10}$ heteroaryl ring selected from the group consisting of pyrimidin-2-yl, pyrimidin-4-yl, pyrimidin-5-yl, 2-isobutoxy-pyrimidin-4-yl, 2-isobutylaminopyrimidin-4-yl, 2-phenoxypyrimidin-4-yl, quinolin-2-yl, quinolin-3-yl, quinolin-4-yl, isoquinolin-1-yl, isoquinolin-3-yl, 1,2,3,4-tetrahydro-quinolin-2-yl, 1,2,3,4-tetrahydro-quinolin-3-yl, pyridin-2-yl, pyridin-3-yl, pyridin-4-yl, and benzo[b]thiophen-2-yl.

65. A compound selected from the group consisting of:
(4S,7S,11aS)-7-Benzoylamino-6-oxo-decahydro-2H-pyrido[1,2-a]azocine-4-carboxylic acid (2-ethoxy-5-oxo-tetrahydro-furan-3-yl)-amide;
(4S,7S,11aS)-7-Benzoylamino-6-oxo-decahydro-2H-pyrido[1,2-a]azocine-4-carboxylic acid (2-hydroxy-5-oxo-tetrahydrofuran-3-yl)-amide;
(4S,7S,11aS)-7-[(Isoquinoline-1-carbonyl)-amino]-6-oxo-decahydro-2H-pyrido[1,2-a]azocine-4-carboxylic acid (2-hydroxy-5-oxo-tetrahydrofuran-3-yl)-amide;
(4S,7S,11aS)-6-Oxo-7-(3-phenyl-ureido)-decahydro-2H-pyrido[1,2-a]azocine-4-carboxylic acid (2-hydroxy-5-oxo-tetrahydro-furan-3-yl)-amide;
(4S,7S,11aS)-7-(3-Chloro-benzoylamino)-6-oxo-decahydro-2H-pyrido[1,2-a]azocine-4-carboxylic acid (2-hydroxy-5-oxo-tetrahydro-furan-3-yl)-amide;
(4S,7S,11aS)-6-Oxo-7-(3-trifluoromethyl-benzoylamino)-decahydro-2H-pyrido[1,2-a]azocine-4-carboxylic acid (2-hydroxy-5-oxo-tetrahydro-furan-3-yl)-amide;
(4S,7S,11aS)-7-[(Benzo[b]thiophene-2-carbonyl)-amino]-6-oxo-decahydro-2H-pyrido[1,2-a]azocine-4-carboxylic acid (2-hydroxy-5-oxo-tetrahydro-furan-3-yl)-amide;

(4S,7S,11aS)-7-[(Naphthalene-2-carbonyl)-amino]-6-oxo-decahydro-2H-pyrido[1,2-a]azocine-4-carboxylic acid (2-hydroxy-5-oxo-tetrahydro-furan-3-yl)-amide;

(4S,7S,11aS)-7-Benzoylamino-6-oxo-decahydro-2H-pyrido[1,2-a]azocine-4-carboxylic acid (2-ethoxy-5-oxo-tetrahydrofuran-3-yl)-amide;

(4S,7S,11aS)-7-[(Isoquinoline-1-carbonyl)-amino]-6-oxo-decahydro-2H-pyrido[1,2-a]azocine-4-carboxylic acid (2-ethoxy-5-oxo-tetrahydro-furan-3-yl)-amide;

(4S,7S,11aS)-6-Oxo-7-(3-phenyl-ureido)-decahydro-2H-pyrido[1,2-a]azocine-4-carboxylic acid (2-ethoxy-5-oxo-tetrahydro-furan-3-yl)-amide;

(4S,7S,11aS)-7-(3-Chloro-benzoylamino)-6-oxo-decahydro-2H-pyrido[1,2-a]azocine-4-carboxylic acid (2-ethoxy-5-oxo-tetrahydro-furan-3-yl)-amide;

(4S,7S,11aS)-6-Oxo-7-(3-trifluoromethyl-benzoylamino)-decahydro-2H-pyrido[1,2-a]azocine-4-carboxylic acid (2-ethoxy-5-oxo-tetrahydro-furan-3-yl)-amide;

(4S,7S,11aS)-7-[(Benzo[b]thiophene-2-carbonyl)-amino]-6-oxo-decahydro-2H-pyrido[1,2-a]azocine-4-carboxylic acid (2-ethoxy-5-oxo-tetrahydro-furan-3-yl)-amide; and (4S,7S,11aS)-7-[(Naphthalene-2-carbonyl)-amino]-6-oxo-decahydro-2H-pyrido[1,2-a]azocine-4-carboxylic acid (2-ethoxy-5-oxo-tetrahydro-furan-3-yl)-amide.

66. A compound selected from:

(4S,7S,11aR)-9-Methyl-5-oxo-6-(3-trifluoromethyl-benzoylamino)-1,3,4,5,6,7,10,10a,-octahydro-2-oxa-4a-aza-benzocyclooctene-4-carboxylic acid-(2-hydroxy-5-oxotetrahydrofuran-3-yl)-amide; and (4S,7S,11aR)-9-Methyl-6-[(naphthalene-2-carbonyl)-amino]-5-oxo-1,3,4,5,6,7,10,10a,-octahydro-2-oxa-4a-aza-benzocyclooctene-4-carboxylic acid-(2-hydroxy-5-oxotetrahydrofuran-3-yl)-amide.

67. A pharmaceutical composition comprising:

A) an effective amount of one or more compounds according to claim 1; and

B) the balance one or more pharmaccutically acceptable exeipients.

68. A method for controlling one or more interleukin-1β converting enzyme inhibitor mediated or interleukin-1β converting enzyme inhibitor modulated mammalian diseases or conditions, selected from the group consisting of osteoarthritis, rheumatoid arthritis, Huntington's disease, Parkinson's disease, Alzheimer's, diabetes, and human Immunodeficiency virus (HIV), said method comprising the step of administering to a human or higher mammal and effective amount of a composition comprising one or more compounds according to claim 1.

69. A method for treating osteoarthritis in humans or higher mammals, said method comprising the step of administering to a human or higher mammal and effective amount of a composition comprising one or more compounds according to claim 1.

* * * * *